(12) United States Patent
Laing et al.

(10) Patent No.: US 11,073,509 B2
(45) Date of Patent: *Jul. 27, 2021

(54) ASSAYS AND METHODS FOR DETERMINING THE RESPONSIVENESS OF AN INDIVIDUAL SUBJECT TO A THERAPEUTIC AGENT

(71) Applicant: Celcuity Inc., Minneapolis, MN (US)

(72) Inventors: Lance Gavin Laing, Orono, MN (US); Brian Francis Sullivan, Medina, MN (US)

(73) Assignee: Celcuity Inc., Minneapolis, MN (US)

( * ) Notice: Subject to any disclaimer, the term of this patent is extended or adjusted under 35 U.S.C. 154(b) by 420 days.

This patent is subject to a terminal disclaimer.

(21) Appl. No.: 15/179,119

(22) Filed: Jun. 10, 2016

(65) Prior Publication Data

US 2017/0067875 A1    Mar. 9, 2017

Related U.S. Application Data

(63) Continuation of application No. PCT/US2014/069980, filed on Dec. 12, 2014.

(60) Provisional application No. 61/915,240, filed on Dec. 12, 2013.

(51) Int. Cl.
| | |
|---|---|
| *G01N 33/50* | (2006.01) |
| *A61K 31/337* | (2006.01) |
| *A61K 31/4709* | (2006.01) |
| *A61K 31/4745* | (2006.01) |
| *A61K 31/506* | (2006.01) |
| *A61K 31/513* | (2006.01) |
| *A61K 31/517* | (2006.01) |
| *A61K 31/519* | (2006.01) |
| *A61K 31/5377* | (2006.01) |
| *A61K 31/555* | (2006.01) |
| *A61K 31/7068* | (2006.01) |
| *A61K 33/24* | (2019.01) |
| *A61K 39/395* | (2006.01) |
| *C07K 16/28* | (2006.01) |
| *C07K 16/32* | (2006.01) |
| *A61K 39/00* | (2006.01) |
| *C12Q 1/6886* | (2018.01) |

(52) U.S. Cl.
CPC ........ *G01N 33/5011* (2013.01); *A61K 31/337* (2013.01); *A61K 31/4709* (2013.01); *A61K 31/4745* (2013.01); *A61K 31/506* (2013.01); *A61K 31/513* (2013.01); *A61K 31/517* (2013.01); *A61K 31/519* (2013.01); *A61K 31/5377* (2013.01); *A61K 31/555* (2013.01); *A61K 31/7068* (2013.01); *A61K 33/24* (2013.01); *A61K 39/39558* (2013.01); *C07K 16/2863* (2013.01); *C07K 16/32* (2013.01); *C12Q 1/6886* (2013.01); *G01N 33/5008* (2013.01); *A61K 2039/505* (2013.01); *C07K 2317/24* (2013.01); *C12Q 2600/106* (2013.01); *G01N 2800/52* (2013.01)

(58) Field of Classification Search
CPC .......... G01N 33/5008; G01N 2800/52; G01N 33/5041

See application file for complete search history.

(56) References Cited

U.S. PATENT DOCUMENTS

| | | | |
|---|---|---|---|
| 4,816,567 A | 3/1989 | Cabilly et al. | |
| 6,041,642 A | 3/2000 | Duncan | |
| 6,077,684 A | 6/2000 | Kravtsov | |
| 6,258,553 B1 | 7/2001 | Kravtsov | |
| 6,331,392 B1 | 12/2001 | Laing et al. | |
| 6,372,772 B1 | 4/2002 | Kirkpatrick et al. | |
| 6,399,078 B1* | 6/2002 | Devico ................ | A61K 38/195 424/278.1 |
| 6,569,628 B2 | 5/2003 | Laing et al. | |
| 6,673,596 B1 | 1/2004 | Sayler et al. | |
| 6,974,706 B1 | 12/2005 | Melker et al. | |
| 7,192,752 B2 | 3/2007 | Xu et al. | |
| 7,429,492 B2 | 9/2008 | Lin et al. | |
| 7,459,303 B2 | 12/2008 | Wang et al. | |
| 7,468,255 B2 | 12/2008 | Xu et al. | |

(Continued)

FOREIGN PATENT DOCUMENTS

| | | | |
|---|---|---|---|
| JP | 2011514522 A | 5/2011 | |
| JP | 2012526992 A | 11/2012 | |

(Continued)

OTHER PUBLICATIONS

Solly et al (Assay and Drug Development Technologies, 2004, vol. 2, pp. 363-371) (Year: 2004).*

(Continued)

*Primary Examiner* — Karen A. Canella

(74) *Attorney, Agent, or Firm* — Nelson Mullins Riley & Scarborough LLP; Jane E. Remillard, Esq.

(57) ABSTRACT

Provided herein are methods for determining the functional status of a cellular pathway in a diseased cell sample obtained from an individual subject. These methods involve contacting a diseased cell sample obtained from the subject with a perturbing agent (e.g., an activating agent) known to perturb a specific cellular pathway when the pathway is functioning normally. A change in one or more physiological response parameters in the presence of the perturbing agent indicates that the cellular pathway targeted by the perturbing agent is functional in the individual subject. Methods of selecting a targeted therapeutic agent for an individual subject are also provided.

7 Claims, 12 Drawing Sheets

(56) References Cited

U.S. PATENT DOCUMENTS

| | | |
|---|---|---|
| 7,470,533 B2 | 12/2008 | Xu et al. |
| 7,560,269 B2 | 7/2009 | Wang et al. |
| 7,592,188 B2 | 9/2009 | Hahn et al. |
| 7,628,085 B2 | 12/2009 | Laing et al. |
| 7,790,406 B2 | 9/2010 | Cunningham et al. |
| 7,832,291 B2 | 11/2010 | Laing et al. |
| 7,863,052 B2 | 1/2011 | Schulz et al. |
| 7,927,822 B2 | 4/2011 | Genick et al. |
| 7,960,170 B2 | 6/2011 | Schulz et al. |
| 8,061,220 B2 | 11/2011 | Laing et al. |
| 8,168,568 B1 | 5/2012 | Mehta et al. |
| 8,202,735 B2 | 6/2012 | Genick et al. |
| 8,257,936 B2 | 9/2012 | Laing et al. |
| 8,298,780 B2 | 10/2012 | Wagner et al. |
| 9,404,915 B2 | 8/2016 | Laing et al. |
| 10,041,934 B2 | 8/2018 | Laing et al. |
| 2002/0031778 A1 | 3/2002 | Laing et al. |
| 2003/0004140 A1 | 1/2003 | Dalton et al. |
| 2003/0096275 A1 | 5/2003 | Laing |
| 2003/0152992 A1 | 8/2003 | Laing et al. |
| 2004/0084307 A1 | 5/2004 | Kim et al. |
| 2004/0115713 A1 | 6/2004 | Laing |
| 2004/0115786 A1 | 6/2004 | Laing |
| 2005/0130321 A1 | 6/2005 | Nicholson et al. |
| 2006/0003372 A1 | 1/2006 | Li et al. |
| 2006/0120204 A1 | 6/2006 | Abassi et al. |
| 2006/0141508 A1 | 6/2006 | Palmer |
| 2006/0160109 A1 | 7/2006 | MacDonald et al. |
| 2006/0177476 A1* | 8/2006 | Saffran ................ A61L 31/005 424/423 |
| 2006/0275825 A1 | 12/2006 | Baird et al. |
| 2006/0292581 A1 | 12/2006 | Laing |
| 2007/0065415 A1 | 3/2007 | Kleinsek et al. |
| 2007/0172894 A1 | 7/2007 | Genick et al. |
| 2008/0020480 A1 | 1/2008 | Lin et al. |
| 2008/0115567 A1 | 5/2008 | Laing et al. |
| 2008/0240543 A1 | 10/2008 | Budach et al. |
| 2008/0299673 A1 | 12/2008 | Wagner et al. |
| 2009/0017488 A1 | 1/2009 | Binder et al. |
| 2009/0060970 A1 | 3/2009 | Toner et al. |
| 2009/0102981 A1 | 4/2009 | Mody |
| 2009/0130703 A1 | 5/2009 | Wagner et al. |
| 2009/0137422 A1 | 5/2009 | Laing et al. |
| 2009/0142790 A1 | 6/2009 | Fang et al. |
| 2009/0192049 A1 | 7/2009 | Baird et al. |
| 2009/0226950 A1 | 9/2009 | Cunningham et al. |
| 2009/0282931 A1 | 11/2009 | Laing et al. |
| 2009/0298162 A1 | 12/2009 | Bouvier et al. |
| 2009/0305304 A1 | 12/2009 | Laing et al. |
| 2010/0003743 A1 | 1/2010 | Schulz et al. |
| 2010/0015721 A1 | 1/2010 | Laing |
| 2010/0043571 A1 | 2/2010 | Laing et al. |
| 2010/0140087 A1 | 6/2010 | Ueno et al. |
| 2010/0143959 A1 | 6/2010 | Cunningham et al. |
| 2010/0196925 A1 | 8/2010 | Genick et al. |
| 2010/0202923 A1 | 8/2010 | Cunningham et al. |
| 2010/0227769 A1 | 9/2010 | Schulz et al. |
| 2010/0291575 A1 | 11/2010 | Shamah et al. |
| 2010/0329933 A1 | 12/2010 | Schulz et al. |
| 2011/0117542 A1 | 5/2011 | Abassi et al. |
| 2011/0130302 A1 | 6/2011 | Shen et al. |
| 2011/0195047 A1* | 8/2011 | Aldabe Arregui ..... A61K 38/21 424/85.2 |
| 2011/0231103 A1 | 9/2011 | Fang |
| 2012/0040866 A1 | 2/2012 | Laing et al. |
| 2012/0101230 A1 | 4/2012 | Wang et al. |
| 2012/0107840 A1 | 5/2012 | Wagner et al. |
| 2012/0237502 A1 | 9/2012 | Darnowski |
| 2013/0045880 A1 | 2/2013 | Singh et al. |
| 2013/0210057 A1 | 8/2013 | Deng et al. |
| 2013/0330761 A1 | 12/2013 | Laing et al. |
| 2015/0125894 A1 | 5/2015 | Laing et al. |
| 2016/0305932 A1 | 10/2016 | Laing et al. |
| 2017/0067875 A1 | 3/2017 | Laing et al. |
| 2017/0343554 A1 | 11/2017 | Sullivan et al. |
| 2018/0321222 A1 | 11/2018 | Laing et al. |
| 2019/0025287 A1 | 1/2019 | Laing et al. |

FOREIGN PATENT DOCUMENTS

| | | |
|---|---|---|
| JP | 2013-543006 A | 11/2013 |
| WO | 03/008530 A2 | 1/2003 |
| WO | 2006/113747 A2 | 10/2006 |
| WO | 2006108183 A2 | 10/2006 |
| WO | 2007/081779 A2 | 7/2007 |
| WO | 2009108637 A1 | 9/2009 |
| WO | 2010/052225 A1 | 5/2010 |
| WO | 2010/085845 A1 | 8/2010 |
| WO | 2010/098166 A1 | 9/2010 |
| WO | 2010132723 A1 | 11/2010 |
| WO | 2012068435 A1 | 5/2012 |
| WO | 2012/157647 A1 | 11/2012 |
| WO | 2013033623 A1 | 3/2013 |
| WO | 2013086301 A1 | 6/2013 |
| WO | 2013/188500 A1 | 12/2013 |
| WO | 2015/089380 A2 | 6/2015 |
| WO | 2016/094904 A1 | 6/2016 |

OTHER PUBLICATIONS

Xia etal (Oncogene, 2002, vol. 21, pp. 6255-6263) (Year: 2002).*
Yang et al (PLoS One Feb. 2013, vol. 8, e56627, 10 pages) (Year: 2013).*
Ressleretal , Proceedings of the IEEE EMBS, 2004, p. 2074-2077 (Year: 2004).*
Muise-Helmericks et al (Journal of Biological Chemistry, 1998, vol. 273, p. 29864-29872) (Year: 1998).*
Niepel et al (Science Signaling, 2013, vol. 6, No. 294, ra84, 12 pages) (Year: 2013).*
Wallasch et al (EMBO Journal, 1995, vol. 14, pp. 4267-4275) (Year: 1995).*
Davis et al, Nature Biotechnology, 2011, vol. 29, pp. 1046-1051 (Year: 2011).*
Sun and Bernard, Trends in Biochemical Sciences, 2014, vol. 39, pp. 465-474 (Year: 2014).*
Gharwan and Groninger, Nature Reviews Clinical Oncology, 2016, vol. 13, pp. 209-227 (Year: 2016).*
Cragg etal, Nature Reviews Cancer, 2009, vol. 9, pp. 321-326 (Year: 2009).*
U.S. Appl. No. 15/192,280, filed Jun. 24, 2016, Lance Gavin Laing.
U.S. Appl. No. 14/590,731, filed Jan. 6, 2015, Lance Gavin Laing.
U.S. Appl. No. 13/494,618, filed Jun. 12, 2012, Lance Gavin Laing.
Abassi, Y., "Label-Free and Dynamic Monitoring of cell-Based Assays", Cell Analysis, Biochemica, No. 2, 8-11 (2008).
Ablin, R. J. et al., "Prostate Transglutaminase (TGase-4) Antagonizes the Anti-tumour Action of MDA-7/IL-24 in Prostate Cancer," Journal of Translational Medicine, vol. 9 (49): 1-9 (2009).
Bohunicky, B. et al., "Biosensors: the new wave in cancer diagnosis," Nanotechnology, Science and Applications, vol. 4:1-10 (2011).
Bosanquet, D. et al.,"Expression of IL-24 and IL-24 Receptors in Human Wound Tissues and the Biological Implications of IL-24 on Keratinocytes," Wound Repair and Regeneration, vol. 20: 896-903 (2012).
Brower, S. et al., "The ChemoFx® Assay: An Ex Vivo Chemosensitivity and Resistance Assay for Predicting Patient Response to Cancer Chemotherapy," Methods in Molecular Biology, vol. 414: Apoptosis and Cancer, 57-78 (2007).
Chan, C-M et al., "Inhibitory Effects of Resveratrol on PDGF-BB-Induced Retinal Pigment Epithelial Cell Migration via PDGFR beta, PI3K/Akt and MAPK Pathways," PLOS, vol. 8, Issue 2, 1-13 (2013).
Chan, L. et al., "A label-free photonic crystal biosensor imaging method for detection of cancer cell cytotoxicity and proliferation," Apoptosis, vol. 12:1061-1068 (2007).
Chigaev, A. et al., "Galphas-coupled receptor signaling actively down-regulates alpha4beta1-integrin affinity: A possible mechanism for cell de-adhesion," BMC Immunology, vol. 9(26):1-16 (2008).

(56) References Cited

OTHER PUBLICATIONS

De Alava, E. et al., "Neuregulin expression modulates clinical response to trastuzumab in patients with metastatic breast cancer," Journal of Clinical Oncology,vol. 25(19):2656-2663 (2007).
European Examination Report, EP Application No. 13731594.1, dated Jun. 28, 2016, 11 pages.
Fang, Ye, "Label-Free and Non-invasive Biosensor Cellular Assays for Cell Adhesion," Journal of Adhesion Science and Technology, vol. 24:1011-1021 (2010).
Gianni, L. et al., "Open-Label, Phase II, Multicenter, Randomized Study of the Efficacy and Safety of Two Dose Levels of Pertuzumab, a Human Epidermal Growth Factor Receptor 2 Dimerization Inhibitor, in Patients with Human Epidermal Growth Factor Receptor 2-Negative Metastatic Breast Cancer," Journal of Clinical Oncology, vol. 28 (7)1131-1137 (2010).
Gil-Ad, I. et al., "Insulin-like-growth-factor-I (IGF-I) antagonizes apoptosis induced by serum deficiency and doxorubicin in neuronal cell culture," Growth Hormone & IGF Research, vol. 9: 458-464 (1999).
Guerra, Y., et al., "Lack of efficacy of adjuvant lapatinib in HER2-negative breast cancer (HER2-ve BC): Analysis of patients in the TEACH trial," 2013 ASCO Annual Meeting: Abstracts: Meeting Library, J. Clin. Oncol, vol. 31(Abstract 628), 2 pages,(2013). Retrieved from the Internet: URL:http://meetinglibrary.asco.org/content/115932-132[retrieved on Feb. 23, 2016].
Hassan, S. et al., "Model for Time Dependency of Cytotoxic Effect of CHS 828 in Vitro Suggests Two Different Mechanisms of Action," The Journal of Pharmacology and Experimental Therapeutics, vol. 299(3):1140-1147 (2001).
Holt, R.U. et al., "Human myeloma cells adhere to fibronectin in response to hepatocyte growth factor," Haematologica/The Hematology Journal, vol. 90(4):479-488. (2005).
Hynes, R., "Integrins: Bidirectional, Allosteric Signaling Machines," Cell, vol. 110:673-687 (2002).
International Preliminary Report on Patentability, PCTUS2014/069980, dated Jun. 14, 2016, 10 pages.
International Search Report and Written Opinion, PCT/US2013/045338, dated Aug. 5, 2013, 12 pages.
International Search Report and Written Opinion, PCT/US2015/065584, dated Mar. 7, 2016, 13 pages.
International Search Report and Written Opinion, PCTUS2014/069980, dated Jun. 26, 2015, 18 pages.
Jonker, DJ et al., "Cetuximab for the treatment of colorectal cancer," New England J of Med., vol. 357 (20):2040-2048 (2007).
Kepp, O. et al., "Cell death assays for drug discovery," Nature Reviews, vol. 10: 221-237 (2011).
Kleinhans, R. et al., "Sensor-based cell and tissue screening for personalized cancer chemotherapy," Med Biol Eng Comput, vol. 50(2):117-126 (2012).
Konya, V. et al., "Endothelial E-type Prostanoid 4 Receptors Promote Barrier Function and Inhibit Neutrophil Trafficking," J. Allergy Clin. Immunol., vol. 131(2), No. 2:532-540 (2013).
Laing, L, "The Pulse of Label Free Indicates the Technology is Alive and Beating," Drug Discovery, vol. 5: 24-30 :Oct./Nov. 2010).
Levasseur, L. et al., "Modeling of the Time-Dependency of in Vitro Drug Cytotoxicity and Resistance," Cancer Research, vol. 58(24):5749-5761 (1998).
Liu Q. et al., "Impedance studies of bio-behavior and chemosensitivity of cancer cells by micro-electrode arrays," . Biosensors and Bioelectronics, Elsevier BV, NL, vol. 24 (5):1305-1310 (2009).
Loum, E. et al., "Oncogramme, a new individualized tumor response testing method: application to colon cancer," Cytotechnology, vol. 62:381-388 (2010).
Matsuo, T. et al., "Analysis of the anti-tumor effect of cetuximab using protein kinetics and mouse xenograft models," BMC Research Notes, vol. 4(140):1-8.(2011).
Mestres, P. et al., "The Bionas technology for anticancer drug screening," Expert Opinion Drug Discovery, vol. 4 (7):785-797 (2009).
Morrison, S. et al., "Chimeric human antibody molecules: Mouse antigen-binding domains with human constant region domains," Proc. Natl. Acad. Sci. USA, vol. 81:6851-6855 (1984).
Ochs, R. et al., "The ChemoFx.® Assay an Ex Vivo Cell Culture Assay for Predicting Anticancer Drug Responses," Methods in Molecular Medicine, vol. 110: Chemosensitivity: vol. 1: In Vitro Assays:155-172 (2005).
Otto, A. et al., "Microphysiological testing for chemosensitivity of living tumor cells with multiparametric microsensor chips," Cancer Detection and Prevention, vol. 27:291-296 (2003).
Otto, A. et al., "Multiparametric Sensor Chips for Chemosensitivity Testing of Sensitive and Resistant Tumor Cells," Recent Results in Cancer Research, vol. 161:39-47 (2003).
Park, J. et al., "Rationale for Biomarkers and Surrogate End Points in Mechanism-Driven Oncology Drug Development," Clinical Cancer Research, vol. 10:3885-3896 (2004).
Peters, M. et al., "Comparing Label-Free Biosensors for Pharmacological Screening with Cell-Based Functional Assays," Assay and Drug Development Technologies, vol. 8(2):219-227 (2010).
Schuler, M. et al., "A phase II trial to assess efficacy and safety of afatinib in extensively pretreated patients with HER2-negative metastatic breast cancer," Breast Cancer Research and Treatment, vol. 134 (3):1149-1159 (2012).
Scott, C. et al., "Label-free whole-cell assays: expanding the scope of GPCR screening," Drug Discovery Today, vol. 15,(17/18): 704-716(2010).
Sprague, L. et al., "Multiparametric Sensor-Chip Based Technology for Monitoring Metabolic Activity: A Proof-of-Principle Study with Live Tissue," Clin. Lab., vol. 52:375-384 (2006).
Struber, M. et al., "Low-potassium Dextran Solution Ameliorates reperfusion injury of the lung and protects surfactant function," The Journal of Thoracic and Cardiovascular Surgery, vol. 120(3):566-572 (2000).
Tyson, J. et al., "Dynamic modeling of estrogen signalling and cell fate in breast cancer cells," Nature Reviews cancer, vol. 11(7):523-530 (2012).
Xi, B. et al., "The application of cell-based label-free technology in drug discovery," Biotechnology Journal, vol. 3 (4):484-495 (2008).
Buck, E. et al., "Loss of homotypic cell adhesion by epithelial-mesenchymal transition or mutation limits sensitivity to epidermal growth factor receptor inhibition," Mol Cancer Ther vol. 6(2):532-541(2007).
Endo, H. et al., "Spheroid Culture of Primary Lung Cancer Cells with Neuregulin 1 /HER3 Pathway Activation," Journal of Thoracic Oncology, vol. 8(2):131-139 (2013).
Kanakry, C., et al., "Neuregulin-1 regulates cell adhesion via an ErbB2/phosphoinositide-3 kinase/Akt-dependent pathway: potential implications for schizophrenia and cancer," PLoS One, vol. 12:e1369: pp. 1-12 (2007).
U.S. Appl. No. 16/027,073, filed Jul. 3, 2018, Lance Gavin Laing.
U.S. Appl. No. 15/533,897, filed Jun. 7, 2017, Brian Francis Sullivan.
U.S. Appl. No. 16/116,392, filed Aug. 29, 2018, Lance Gavin Laing.
Aroui, S. et al., "Naringin suppresses cell metastasis and the expression of matrix metalloproteinases (MMP-2 and MMP-9) via the inhibition of ERK-P38-JNK signaling pathway in human glioblastoma," Chemico-Biological Interactions, vol. 244:195-203 (2015).
Atienza, J. et al., "Label-free and real-time cell-based kinase assay for screening selective and potent receptor tyrosine kinase inhibitors using microelectronic sensor array," Journal of Biomolecular Screening, vol. 11(6): 634-643 (2006)
Capuzzo, F., "The Human Epidermal growth factor Receptor (HER) family:structure and function," Guide to Targeted Therapies: EGFR mutations in NSCLC, Chapter Two, Springer International Publishing Switzerland, 12 pages (2014) DOI 10.1007/978-3-319-03059-3_2.
Extended European Search Report, European Application No. 18157442.7 dated Apr. 3, 2018, 10 pages.
Fountzilas, G. et al., "Evaluation of the prognostic role of centromere 17 gain and HER2/topoisomerase II alpha gene status and protein expression in patients with breast cancer treated with anthracycline-containing adjuvant chemotherapy: pooled analysis of two Hellenic

(56) References Cited

OTHER PUBLICATIONS

Cooperative Oncology Group (HeCOG) phase III trials," BMC Cancer, vol. 13:163, 16 pages (2013)

Hermanto U. et al., "ErbB2-overexpressing human mammary carcinoma cells display an increased requirement for the phosphatidylinositol 3-kinase signaling pathway in anchorage-independent growth", Oncogene, vol. 20 (51):7551-7562 (2001).

Huang, Y et al., "A functional signal profiling test for identifying a subset of HER2-negative breast cancers with abnormally amplified HER2 signaling activity," OncoTarget, vol. 7(48):78577-78590 (2016) XP055474584, DOI: 10.18632/oncotarget.12480.

Huang, Y., et al., "Development of a test that measures real-time HER2 signaling function in live breast cancer cell lines and primary cells," BMC Cancer, vol. 17 (199):18 pages (2017), XP055474590, DOI: 10.1186/s12885-017-3181-0.

International Preliminary Report on Patentability, PCT/US2013/045338, dated Dec. 16, 2014, 8 pages.

International Preliminary Report on Patentability, PCT/US2015/065584, dated Jun. 13, 2017, 10 pages.

International Search Report and Written Opinion, PCT/US2018/022936, dated Jul. 19, 2018, 25 pages.

Invitation to Pay Additional Fees and, Where Applicable, Protest Fee, PCT/US2018/022936, dated May 24, 2018, 16 pages.

Laing, L. et al., "Dynamic real-time signaling profiles of live primary cells to characterize the response of PI3K and MAPK pathways in HER2+ breast cancer cells to attenuation with lapatinib: Tests of reproducibility of method," Journal of Clinical Oncology, vol. 32:15_suppl, e11597-e11597, 2014 American Society of Clinical Oncology (ASCO) (2014).

Laing, L. et al., "Profiling of signaling pathways in live tumor cells to assess drug mechanism of action: A method to predict drug efficacy in a patient [e11583]," American Society of Clinical Oncologists 2014, Journal of Clinical Oncology, vol. 32:15_suppl, e11583-e11588, (2014) American Society of Clinical Oncology (ASCO) Poster Presentation.

McGuinness, R., "Impedance-based cellular assay technologies: recent advances, future promise," Current Opinion in Pharmacology, vol. 7(5):535-540 (2007).

Moasser, M. "The oncogene HER2; Its signaling and transforming functions and its role in human cancer pathogenesis," Oncogene, vol. 26(45):6469-6487 (2007).

Arteaga, C. et al., "ERBB Receptors: From Oncogene Discovery to Basic Science to Mechanism-Based Cancer Therapeutics," Cancer Cell, vol. 25(3):282-303 (2014).

Extended European Search Report, European Application No. 19180662.9, dated Dec. 9, 2019, 10 pages.

International Preliminary Report on Patentability, PCT/US2018/022936, dated Sep. 24, 2019, 14 pages.

Menendez, J.A., et al., "Trastuzumab in Combination With Heregulin-Activated Her-2 (erbB-2) Triggers a Receptor-Enhanced Chemosensitivity Effect in the Absence of Her-2 Overexpression," Journal of Clinical Oncology, vol. 24:3735-3746 (2006).

Montero, J. et al., "P-Rex1 participates in Neuregulin-ErbB signal transduction and its expression correlates with patient outcome in breast cancer," Oncogene, vol. 30(9):1059-1071 (2011).

Singer F. C. et al., "Predicting the efficacy of trastuzumab-based therapy in breast cancer: Current standards and future strategies," Biochimica et Biophysica Acta Reviews on Cancer, vol. 1786:105-113 (2008).

Tan, M. et al., "Heregulin beta1-activated phosphatidylinositol 3-kinase enhances aggregation of MCF-7 breast cancer ells independent of extracellular signal-regulated kinase," Cancer Res., vol. 59(7):1620-1625 (1999).

Unger F. et al., "Prediction of Individual Response to Anticancer Therapy: Historical and Future Perspectives," Cell Mol. Life Science, vol. 72:729-757 (2015).

Yuste, L. et al., "Activation of ErbB2 by Overexpression or by Transmembrane Neuregulin Results in Differential Signaling and Sensitivity to Herceptin," Cancer Res., vol. 65 (15): 6801-6810 (2005).

Zhao, W. et al, "Neuregulin 1 enhances cell adhesion molecule l1 expression in human glioma cells and promotes their migration as a function of malignancy," J Neuropathol Exp Neurol., vol. 72(3):244-255 (2013).

U.S. Appl. No. 16/027,073, filed Jul. 3, 2018, Lance Gavin Laing, US 2018-0321222.

U.S. Appl. No. 15/192,280, filed Jun. 24, 2016, Lance Gavin Laing, U.S. Pat. No. 10,041,934.

U.S. Appl. No. 14/590,731, filed Jan. 6, 2015, Lance Gavin Laing, U.S. Pat. No. 9,404,915.

U.S. Appl. No. 13/494,618, filed Jun. 12, 2012, Lance Gavin Laing, US 2013-0330761.

U.S. Appl. No. 15/533,897, filed Jun. 7, 2017, Brian Francis Sullivan, US 2017-0343554.

U.S. Appl. No. 16/116,392, filed Aug. 29, 2018, Lance Gavin Laing, US 2019-0025287.

U.S. Appl. No. 15/192,280, Jun. 27, 2018.
U.S. Appl. No. 15/192,280, Apr. 4, 2018.
U.S. Appl. No. 14/590,731, Apr. 6, 2016.
U.S. Appl. No. 14/590,731, Nov. 6, 2015.
U.S. Appl. No. 14/590,731, Jun. 2, 2015.
U.S. Appl. No. 14/590,731, Mar. 12, 2015.
U.S. Appl. No. 13/494,618, Jul. 10, 2014.
U.S. Appl. No. 13/494,618, Jan. 15, 2014.
U.S. Appl. No. 13/494,618, Jun. 7, 2013.
U.S. Appl. No. 13/494,618, Nov. 28, 2012.
U.S. Appl. No. 13/494,618, Aug. 20, 2012.
U.S. Appl. No. 15/533,897, Oct. 17, 2019.
U.S. Appl. No. 15/533,897, Dec. 20, 2018.
U.S. Appl. No. 15/533,897, Jul. 26, 2018.
U.S. Appl. No. 15/533,897, Jun. 1, 2018.

Choi, B-K., et al., "ERBB3 (HER3) is a key sensor in the regulation of ERBB-mediated signaling in both low and high ERBB2 (HER2) expressing cancer cells," Cancer Medicine, vol. 1:28-38(2013).

Cunningham, B. et al., "Label-free assays on the BIND system," Journal of Biomolecular Screening, vol. 9 (6):481-490 (2004).

Lee, CY et al., "Neuregulin autocrine signaling promotes self-renewal of breast tumor-initiating cells by triggering HER2/HER3 activation," Cancer Res., vol. 74(1):341-52 (2014).

Ona, T. et al., "Advanced dynamic monitoring of cellular status using label-free and non-invasive cell-based sensing echnology for the prediction of anticancer drug efficacy," Anal. Bioannal. Chem., vol. 398:2505-2533 (2010).

* cited by examiner

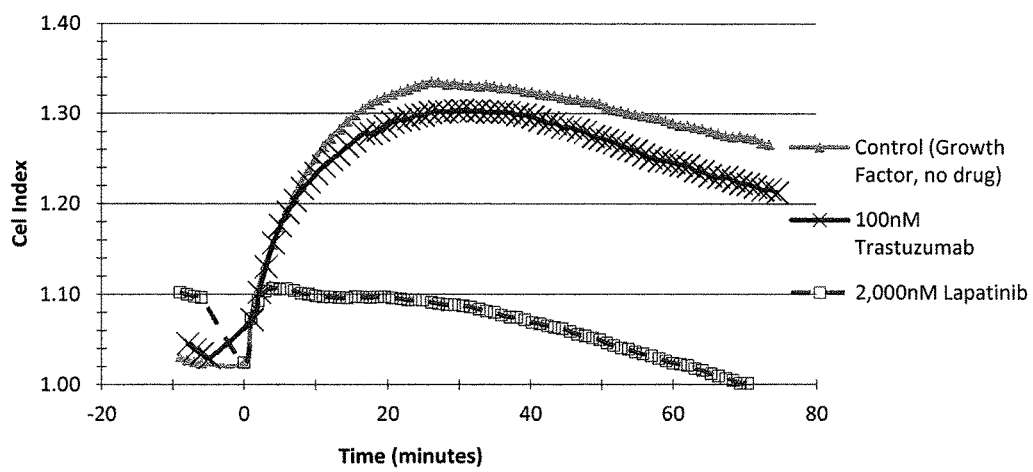
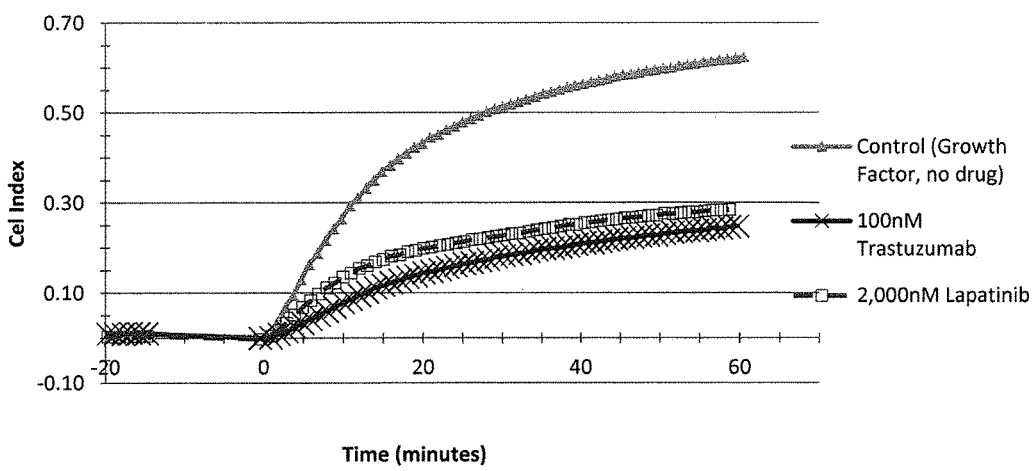

| Reference Standard | Celcuity Test | | Total |
|---|---|---|---|
| (clinical response) | Response | Non-Response | |
| Non-response | 0 | 1 | 1 |
| Response | 3 | 0 | 3 |
| Total | 3 | 1 | 4 |

Figure 1C. Third Party Measured Clinical Response vs. Celcuity Test Prediction - B1 and B4 cells with Trastuzumab or Lapatinib

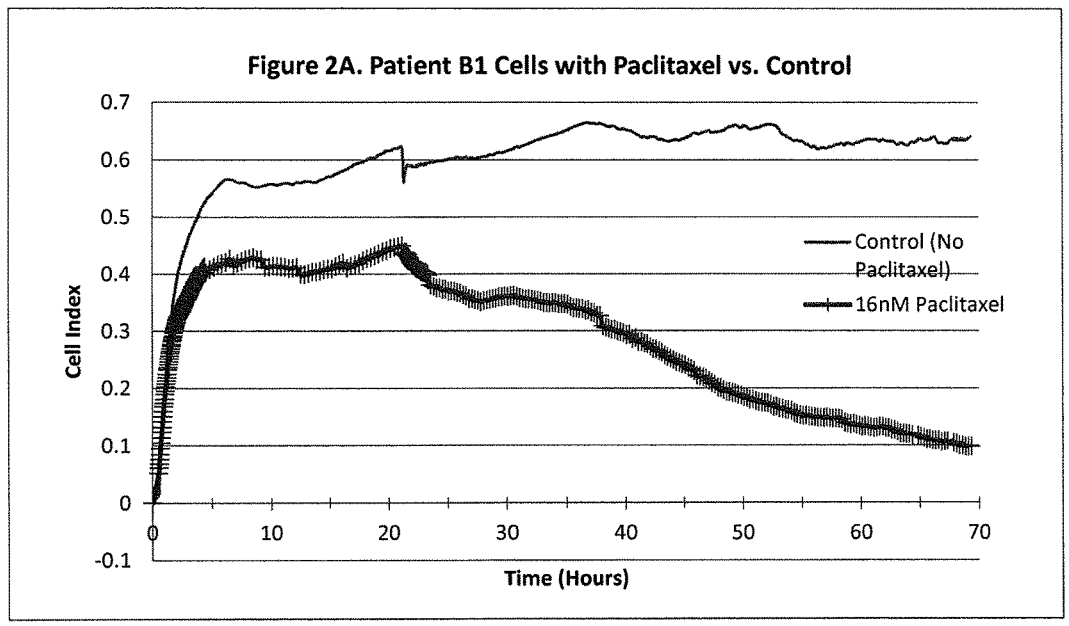
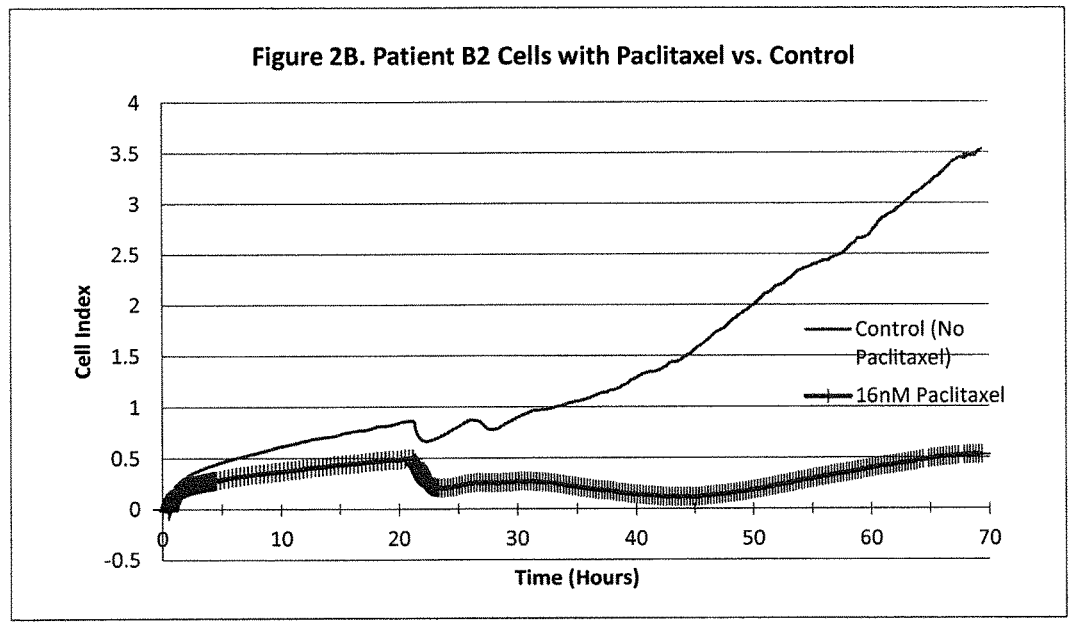

| Figure 2C. Third Party Measured Clinical Response vs. Celcuity Test Prediction - B1 and B2 cells with Paclitaxel | | | |
|---|---|---|---|
| Reference Standard (clinical response) | Celcuity Test | | Total |
| | Response | Non-Response | |
| Non-response | 0 | 0 | 0 |
| Response | 2 | 0 | 2 |
| Total | 2 | 0 | 2 |

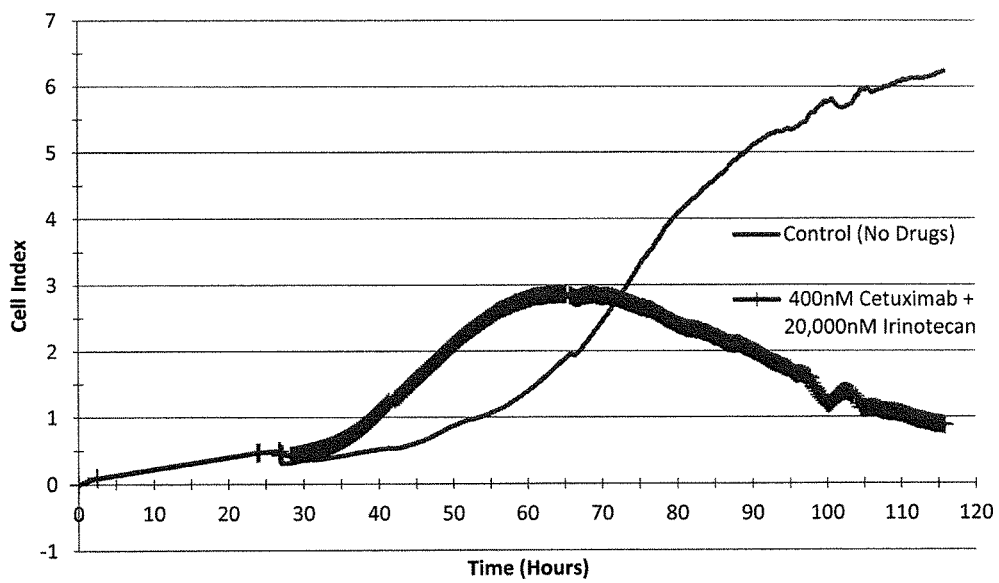
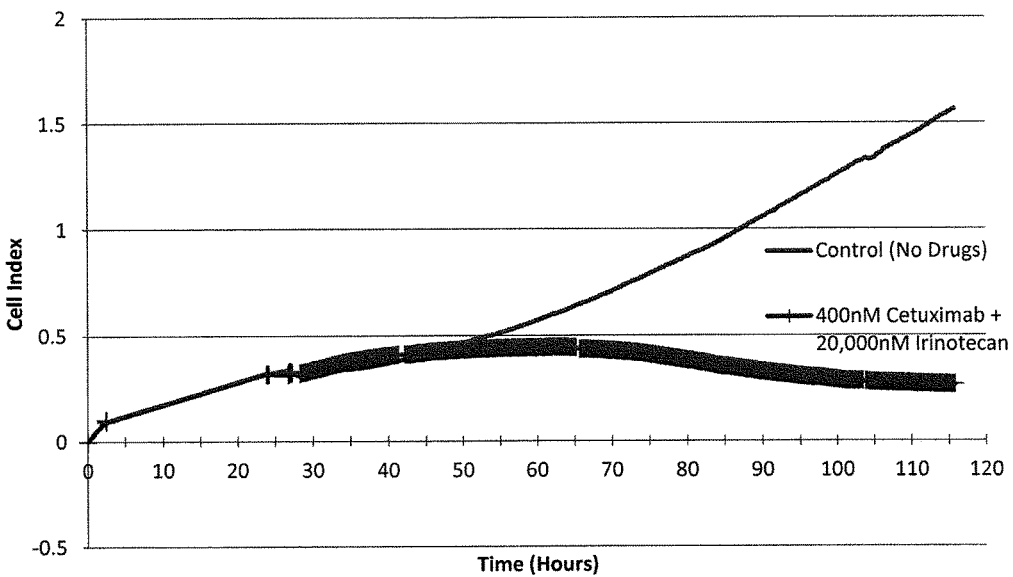

| Figure 3C. Third Party Measured Clinical Response vs. Celcuity Test Prediction - C1 and C2 cells tested in Combination with Cetuximab and Irinotecan ||||
|---|---|---|---|
| Reference Standard | Celcuity Test || Total |
| (clinical response) | Response | Non-Response | |
| Non-response | 0 | 0 | 0 |
| Response | 2 | 0 | 2 |
| Total | 2 | 0 | 2 |

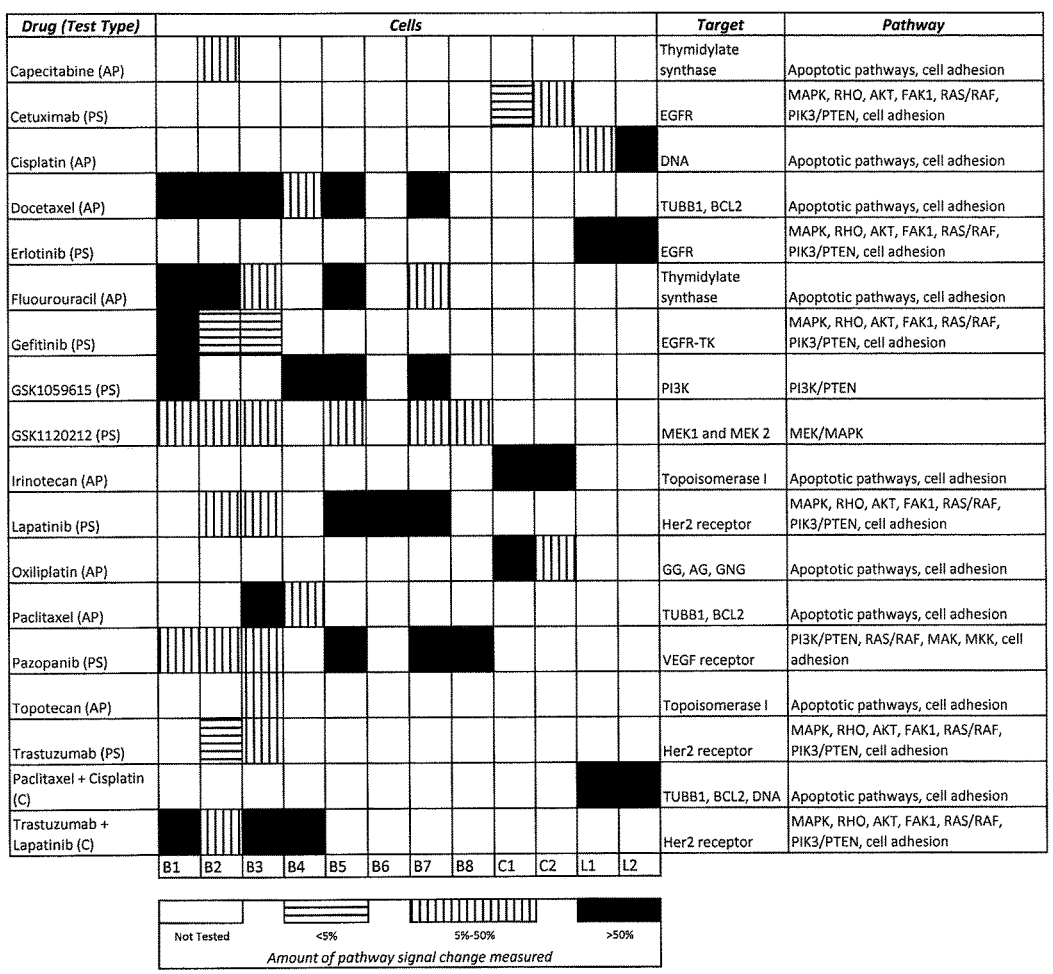
Figure 4. Summary Results of 57 CELx Tests Described in Example 4 on some of the cell and drug combinations possible from a selection of 12 Different Patients, 15 Different Drugs, 11 Pathways Figure 5. Concordance between Optical Biosensor and Impedance Biosensor Measurement
*Pathway Signal Change vs. Control after Cetuximab is added to Cells B1-B4 as measured on an Optical Biosensor and Impendance Biosensor*
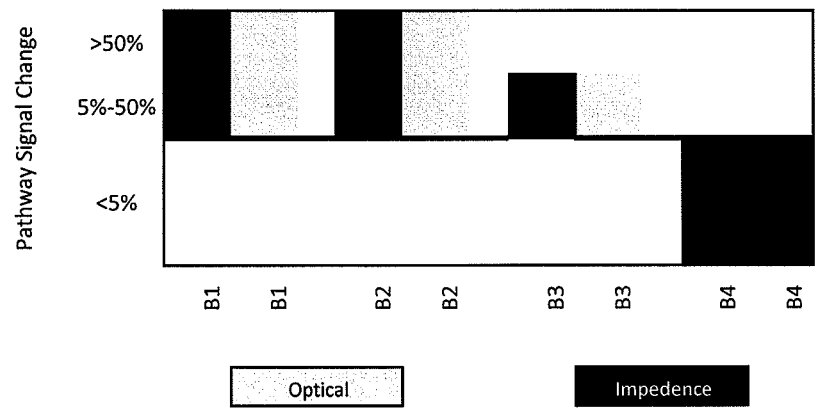

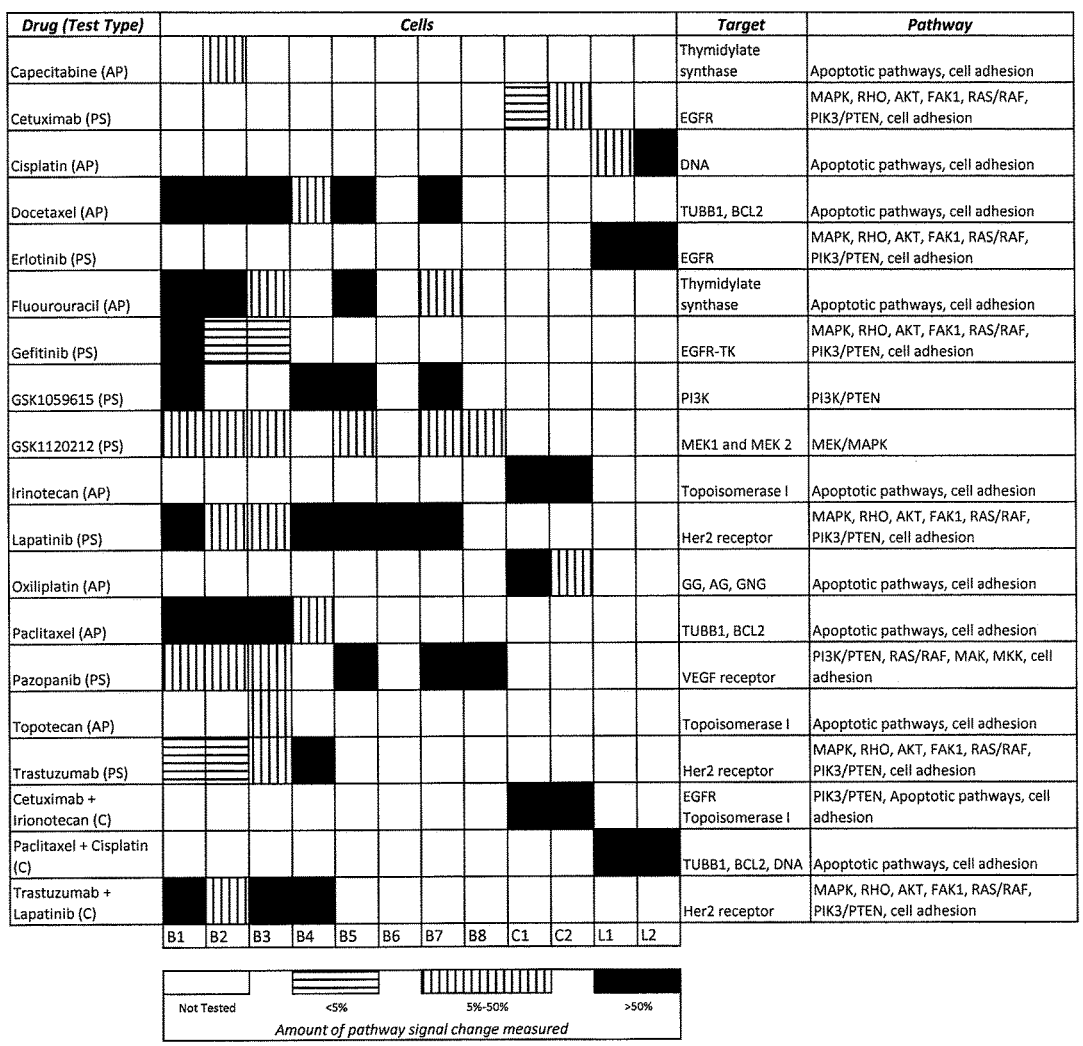
Figure 6. Summary of All 65 CELx Test Results and Predictions Described in Examples 1-4

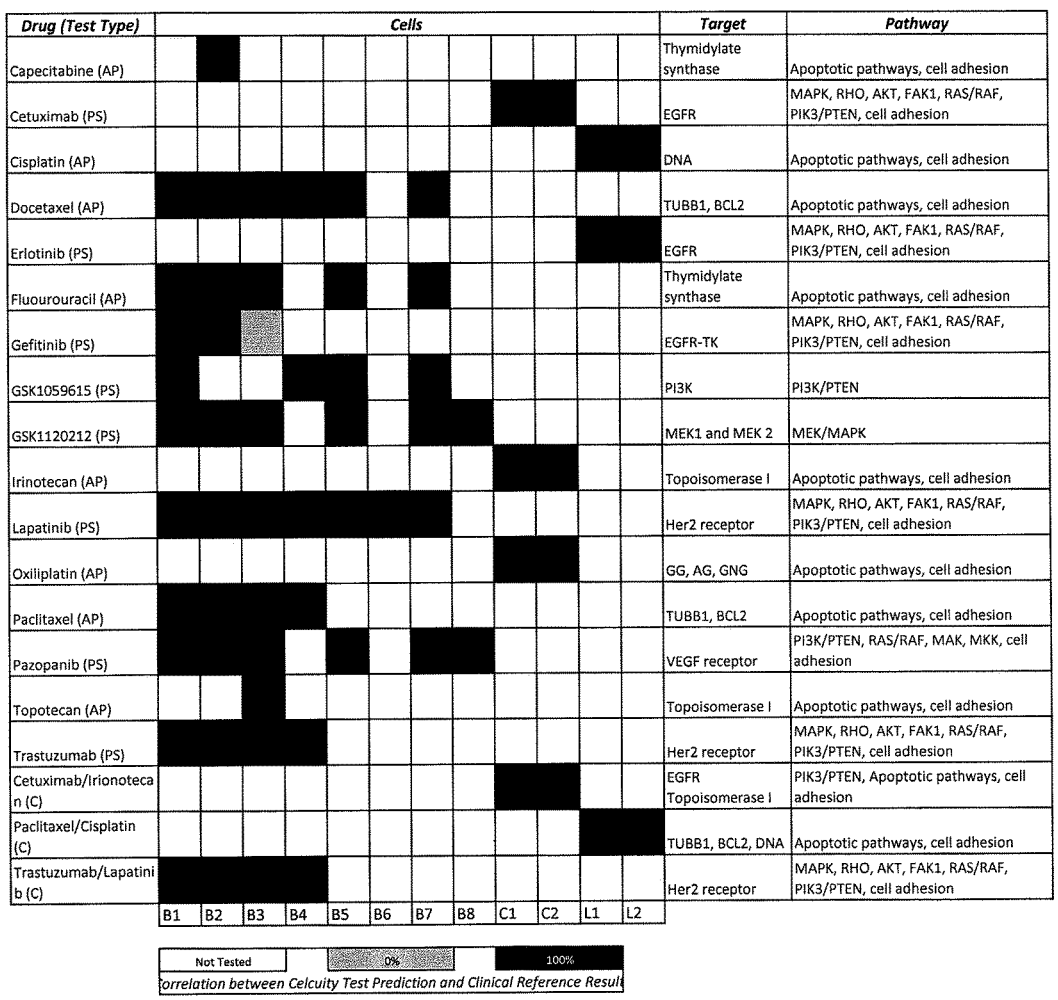
Figure 7. Correlation of All 65 CELx Test Predictions Described in Examples 1-4 with Third Party Clinical Reference Results

Figure 8A. Third Party Measured Clinical Response vs. Celcuity Test Prediction - All Patients Cells from Examples 1-4

| Reference Standard (clinical response) | Celcuity Test Response | Celcuity Test Non-Response | Total |
|---|---|---|---|
| Non-response | 0 | 4 | 4 |
| Response | 60 | 1 | 61 |
| Total | 60 | 5 | 65 |

Figure 8B. Third Party Measured Clinical response vs. Celcuity Test Prediction - Breast Cancer Cells Tested in Examples 1-4

*Breast Cancer Cells tested with capecitabine, cetuximab, docetaxel, fluorouracil, gefitinib, GSK1059615, GSK1120212, lapatinib, paclitaxel, pazopanib, trastuzumab, topotecan, and trastuzumab/lapatinib*

| Reference Standard (clinical response) | Celcuity Test Response | Celcuity Test Non-Response | Total |
|---|---|---|---|
| Non-response | 0 | 3 | 3 |
| Response | 47 | 1 | 48 |
| Total | 47 | 4 | 51 |

Figure 8C. Third Party Measured Clinical response vs. Celcuity Test Prediction - Colon Cancer Cells Tested in Examples 1-4

*Colon Cancer Cells tested with cetuximab, irinotecan, oxiliplatin, and cetuximab/irinotecan*

| Reference Standard (clinical response) | Celcuity Test Response | Celcuity Test Non-Response | Total |
|---|---|---|---|
| Non-response | 0 | 1 | 1 |
| Response | 7 | 0 | 7 |
| Total | 7 | 1 | 8 |

Figure 8D. Third Party Measured Clinical response vs. Celcuity Test Prediction - Lung Cancer Cells Tested in Examples 1-4

*Lung Cancer Cells tested with cisplatin, erlotinib, paclitaxel/cisplatin*

| Reference Standard (clinical response) | Celcuity Test Response | Celcuity Test Non-Response | Total |
|---|---|---|---|
| Non-response | 0 | 0 | 0 |
| Response | 6 | 0 | 6 |
| Total | 6 | 0 | 6 |

Figure 9. Test Sensitivity and Specificity for all 65 CELx Test Results described in Examples 1-4

|  | Sensitivity | Specificity | No. |
|---|---|---|---|
| Total | 98% | 100% | 65 |
| Disease | | | |
| Breast | 98% | 100% | 51 |
| Lung | 100% | 100% | 6 |
| Colon | 100% | 100% | 8 |
| Drug Type | | | |
| Pathway | 97% | 100% | 34 |
| Anti-proliferative | 100% | 100% | 23 |
| Combination | 100% | 100% | 8 |
| Drug | | | |
| Capecitabine | 100% | 100% | 1 |
| Cetuximab | 100% | 100% | 2 |
| Cisplatin | 100% | 100% | 2 |
| Docetaxel | 100% | 100% | 6 |
| Erlotinib | 100% | 100% | 2 |
| Fluourouracil | 100% | 100% | 5 |
| Gefitinib | 50% | 100% | 3 |
| GSK1059615 | 100% | 100% | 4 |
| GSK1120212 | 100% | 100% | 6 |
| Irinotecan | 100% | 100% | 2 |
| Lapatinib | 100% | 100% | 7 |
| Oxiliplatin | 100% | 100% | 2 |
| Paclitaxel | 100% | 100% | 4 |
| Pazopanib | 100% | 100% | 6 |
| Topotecan | 100% | 100% | 1 |
| Trastuzumab | 100% | 100% | 4 |
| Cetuximab/Irionotecan | 100% | 100% | 2 |
| Paclitaxel/Cisplatin | 100% | 100% | 2 |
| Trastuzumab/Lapatinib | 100% | 100% | 4 |
| Pathway | | | |
| AKT | 95% | 100% | 20 |
| Apoptotic pathways | 100% | 100% | 23 |
| Cell Adhesion | 97% | 100% | 65 |
| FAK1 | 95% | 100% | 20 |
| MAK | 100% | 100% | 6 |
| MAPK | 95% | 100% | 20 |
| MEK/MAPK | 100% | 100% | 6 |
| MKK | 100% | 100% | 6 |
| PI3K/PTEN | 96% | 100% | 26 |
| RAS/RAF | 96% | 100% | 26 |
| RHO | 95% | 100% | 20 |

ASSAYS AND METHODS FOR DETERMINING THE RESPONSIVENESS OF AN INDIVIDUAL SUBJECT TO A THERAPEUTIC AGENT

RELATED APPLICATIONS

This application is a continuation of International Application No. PCT/US2014/069980, filed Dec. 12, 2014, which claims priority to and the benefit of U.S. Provisional patent Application Ser. No. 61/915,240, filed on Dec. 12, 2013. The contents of the aforementioned applications are hereby incorporated herein by reference in their entirety.

BACKGROUND

Treatment of diseased individuals has made significant progress since the discovery that chemicals and exogenous proteins can be effective human therapeutic agents against specific cellular targets. However, there is still significant room for improvement in the treatment of many common diseases such as cancer. One of the main drivers of the Human Genome Project was to discover the genetic causes of diseases, in order to advance the development and prescription of therapeutic intervention. If reports are to be believed, all human genes have been identified through the Human Genome Project. Many of these genes have been statistically linked to disease in human populations. Yet knowledge of the genetic links of a disease or detection of genetic biomarkers does not always effectively predict disease course or therapeutic outcome. So too have the genetic links and even the quantification of protein expression levels from those genes been very limited in determining appropriate therapeutic courses.

Petabyte amounts of genetic information have been collected. A great deal of statistical and analytical modeling computing power has been applied to the genetic data collected to analyze many different types of diseases. At least two important facts have emerged from this process. First, a "disease" like breast cancer is heterogeneous in part because breast cancer in one individual can be completely different from the same cancer in another individual in genetic makeup, protein expression levels, and response to therapeutic intervention. Second, detection of current genetic biomarkers has poor predictive value in the majority of cases.

Contemporary targeted drugs are discovered and developed along a process with specific limited number of human cell models in mind. Many of these cell lines are engineered to provide for optimized screening environments of large libraries of potential drugs to select those with desired activity against a particular cellular target. Employment of this process can be misleading as to the efficacy of potential drugs in light of clinical information indicating that each patient's disease is different from other patients with the same disease. The drug discovery and development process to date is not very effective at identifying responsive humans prior to clinical trials and continues to suffer a high failure rate throughout the clinical development process. Many of the drugs that are approved through the regulatory clinical development process that focuses on reducing harm to patients suffer from poor efficacy rates in actual disease patient populations.

Not all disease condition presentations to the clinical physician arise from the same cause. In a simple example, inflammation of bone joints can arise from several sources, some internal, some external, some "genetically linked," and some with yet unknown causes. The medical sciences are fairly effective in triaging patients for infectious diseases when the external pathogen can be identified properly. Physicians have fewer tools at hand for predicting which of the therapies that are currently available will lead to reduction of inflammation from internal causes. Physicians lack the knowledge of how a specific patient's cells are functioning, or more appropriately malfunctioning, and how they will respond to one of the many therapeutics that are available for treating the disease that presents clinically as "inflammation." They may know that an aberrant gene is present but do not know how that affects the disease course in a specific patient. They may know specifically how a drug is supposed to act but not why a particular patient may be unresponsive or resistant to that drug activity.

Patients need better identification of their particular disease cause and better informed decision-making for an effective therapeutic course. Human genome sequencing and other genetic quantification tools have informed doctors that each patient's disease is somewhat unique to that patient. This information has spawned a whole business around personalized medicine, where each patient could potentially receive a customized therapeutic regimen customized for their disease. Drugs are being developed for specific gene-related disease indications. This ideal approach has yet to be validated due primarily to significant shortcomings of the current prognostic toolset. The genes may be present but their function in the context of a particular individual is not correlated.

One response to the realization that each patient is different and that many times therapies fail to effect a positive response, has been the development of companion diagnostics. This type of diagnostic test is designed using contemporary biomarker detection tools to try to identify those patients that are more likely to respond to a particular drug. The test involves looking for increased gene number, gene mutation, or altered expression level of a particular gene. Success rates for most of these tests at predicting significant therapeutic response are often much less than 50%.

Thus there remains a need to provide better prognostic indicators for the effectiveness of therapeutics for an individual.

SUMMARY OF THE INVENTION

Some drugs are being targeted for specific gene-related disease indications. This approach has not yet been broadly utilized due primarily to significant shortcomings of the current prognostic toolset. The kits and methods as described herein provide for a method of selecting a therapeutic agent that shows efficacy against an individual's disease. In certain embodiments, the therapeutic agent is contacted to label free live whole cells from diseased tissue in a CReMS and a change or lack thereof in a physiologic parameter of the cells is detected in the presence of the therapeutic agent. The therapeutic agent is selected to treat the subject that results in a change in a physiological parameter of the disease cell as compared to a baseline measurement.

Accordingly, in one aspect, the invention provides a method of selecting one or more therapeutic agents either at the initial diagnosis or throughout treatment. In certain embodiments, the therapeutic agent is commercially approved for use to treat a disease or disorder in an individual. The method comprises administering one or more therapeutic agents to at least one isolated disease cell sample from the subject in a cellular response measurement system;

determining whether a change occurs in cellular response parameter of the disease cell sample in response to the therapeutic agent or agents as compared to a baseline measurement of the cellular response parameter before administration of the therapeutic agent or agents, wherein the change in cellular response parameter indicates that the agent or agents has therapeutic efficacy for the disease in the individual subject. In certain embodiments, the isolated disease cell sample comprises label free whole cells. In certain embodiments, the change of the cellular response parameter in the isolated disease cell is monitored continuously for a defined period of time. In other embodiments, the method further comprises selecting the therapeutic agent or combination of therapeutic agents that results in the change of at least one cellular response or physiologic parameter and communicating the selected agent to a health care provider. In other embodiments, the method further comprises administering the therapeutic agent or combination of therapeutic agents that results in the change of at least one cellular response or physiologic parameter to the subject.

In other embodiments, the method for selecting a treatment for an individual subject comprises determining therapeutic efficacy of an agent for a disease in the individual subject comprising administering the agent to at least one isolated label free disease cell sample from the individual subject in a cellular response measurement system (CReMS), wherein the disease cell sample is selected from the group consisting of a cancer cell sample, a cell sample from a subject with an autoimmune disease, a cell sample from a tissue infected with a foreign agent and combinations thereof; continuously measuring a change in at least one physiological response parameter of the cell sample for a defined period of time in the presence of the therapeutic agent; and determining whether a change in a physiological response parameter of the cell sample to the agent occurs as compared to a baseline measurement, wherein the change in physiological response indicates that the agent has therapeutic efficacy for the disease in the individual subject.

In other embodiments, the method for selecting a treatment for an individual subject having cancer comprises determining therapeutic efficacy of an agent for cancer in the individual subject comprising: administering the agent to at least one isolated label free cancer cell sample from the individual subject in a biosensor; continuously measuring a change in at least one physiological response parameter of the cell sample for a defined period of time in the presence of the therapeutic agent; and selecting the therapeutic agent for treatment of the subject that exhibits a change in a physiological response parameter of the cell sample as compared to a baseline measurement.

In another aspect, the invention provides a method of determining the functional status of a cellular pathway in diseased cells obtained from an individual subject, by contacting a diseased cell sample obtained from the subject with a perturbing agent known to agonize or antagonize a cellular pathway when the pathway is functioning normally. One or more physiological response parameters can be continuously measured in viable cells in the sample. Analysis of the continuous measurements can be used to determine whether a change in one or more physiological response parameters occurs in the diseased cell sample in the presence of the perturbing agent, relative to a suitable control. A change in one or more physiological response parameters in the presence of the perturbing agent, relative to a suitable baseline or control, indicates that the cellular pathway targeted by the perturbing agent is functional in the individual subject.

In another aspect, the invention provides a method of selecting a targeted therapeutic agent for an individual subject, by contacting a diseased cell sample obtained from the subject with a perturbing agent known to agonize or antagonize a cellular pathway when the pathway is functioning normally, continuously measuring one or more physiological response parameters in viable cells in the sample, and determining by analysis of the continuous measurements whether a change in one or more physiological response parameters occurs in the diseased cell sample in the presence of the perturbing agent, relative to a suitable baseline or control, wherein a change in one or more physiological response parameters in the presence of the perturbing agent, relative to a suitable baseline or control, indicates that the subject will be responsive to a targeted therapeutic agent that targets the cellular pathway.

In one embodiment, the foregoing methods can also involve administering the targeted therapeutic agent to the subject.

In certain embodiments, the physiological response parameter can be cell adhesion, cell attachment, cell morphology, cell proliferation, cell signaling, cell density, cell size, cell shape, cell polarity, pH, $O_2$, $CO_2$, glucose, and combinations thereof. For example, the physiological response parameter can be cell adhesion or attachment.

In one embodiment, the perturbing agent targets one or more cellular pathways including MAPK-PK, RAS/RAF, RHO, FAK1, MEK/MAPK, MAK, MKK, AKT, EGF receptor, Her2 receptor, Her 3 receptor, Her 4 receptor, PIK3/PTEN, VEGF receptor pathway inhibitors, cell adhesion, TGFbeta/SMAD, WNT, Hedgehog/GLI, HIF1 alpha, JAK/STAT, Notch, control of G1/S transition, DNA damage control, and apoptosis. The perturbing agent can be, for example, a protein, a peptide, a nucleic acid, a metabolite, a ligand, an organic molecule, a signaling factor, a biochemical, or a combination thereof. In one embodiment, the perturbing agent is targeted to a cell pathway component involved in cell cycle regulation selected from the group consisting of CDK4, CDK6, PD-1, cyclin A, cyclin B, cyclin C, cyclin D, cyclin E, cyclin F, and G1/S cyclins.

Targeted therapeutic agents can include, in certain embodiments, one or more of trastuzumab, pertuzumab, lapatinib, docetaxel, tamoxifen, cisplatin, abraxane, paclitaxel injection, brentuximab vedoton, everolimus, pemetrexed, exemestane, ofatumumab, bevacizumab, alemtuzumab, irinotecan, bicalutamide, oxaliplatin, cetuximab, visomedegib, toremifene citrate, fulvestrant, gemcitabine, imatinib, ixabepilone, topeotecan, axitinib, romidepsin, cabrazitaxel, sorafenib, infliximab, lenalidomide, rituximab, dasatinib, sunitinib, erlotinib, nilotinib, paclitaxel, temozolomide, trioxide, panitumumab, bortezomib, azacitidine, pazopanib, crizotinib, capecitabine, ipilimumab, vemurafenib, goserelin acetate, abiraterone, a BH3 mimetic, navitoclax, anastrozole, letrozole, an aromatase inhibitor, cyclophosphamide, doxorubicin, methotrexate, fluorouracil, ixabepilone, carboplatin, aflibercept, temsirolimus, irbritumomab, abiraterone, custirsen, neratinib, enzalutamide, nivolumab, palbociclib, regorafenib, entinostat, afatinib, ARN-509, ARN-810, BIND-014, dabrafenib, daratumumab, lambrolizumab, LDK378, MM-121, sym004, trastuzumab emtansine, tivozanib, trametinib, axitinib, LY2835219, MPDL320A, obinutuzumab, Sym004, Tositumomab, trametinib, necitumumab, ramucirumab, and combinations thereof.

In one embodiment, the diseased cell sample is a cancer cell sample, e.g., a breast cancer, lung cancer, or colon cancer sample.

The change in one or more physiological response parameters can be assessed, in some embodiments, using non-linear Euclidean analysis. For example, the change in one or more physiological response parameters can be assessed using an analytical method that includes arithmetic summation of the difference at multiple time points, temporal maxima, temporal minima, time to reach maxima or minima, changes in slope, absolute drop in biosensor signal, a total of all measurements, or combinations thereof. In one embodiment, the change in one or more physiological response parameters is measured by a change in temporal maxima or minima.

In another aspect, the invention provides a method of identifying cell pathway components affected by perturbing and/or therapeutic agents in an individual subject. These methods involve contacting an isolated, label-free cellular sample obtained from the subject with a perturbing agent and/or a therapeutic agent, monitoring the effect of the agents by continuously measuring at least one physiological response parameter in viable cells in the sample, determining by analysis of the continuous measurements whether a change in the physiological response parameter occurs, thereby characterizing the sensitivity of the sample to the agent(s), and analyzing components of a cell pathway targeted by the agent(s) using a method selected from proteomics, qPCR, genomics, RNA quantification, tandem liquid chromatography-mass spectroscopy, and metabolomics, thereby determining whether components of the cell pathway are altered by the presence of the perturbing agent and/or the therapeutic agent in the cellular sample. In one embodiment, the activity of the perturbing agent on the sample is halted prior to analysis of the cell pathway components.

In another embodiment, the invention provides a method of determining a cut-off value for a test that identifies patients likely or unlikely to respond to a targeted therapeutic agent. This method can involve selecting a group of patients, each of whom has the same disease and is prescribed the same therapeutic; deriving a test value for each subject within a group of patients, wherein the test value results from analysis of continuous measurement of one or more physiological response parameters in a patient cell sample during treatment with a therapeutic agent and/or a perturbing agent; observing the health status of each member of the group of patients tested over a period of time sufficient for a significant percentage of the total patients tested to reach a predefined clinical endpoint; recording the length of time required for each of the patients to reach, if they did, the predefined clinical endpoint; identifying two or more candidate cut-off values that are equidistant in value to the other, wherein each candidate cut-off value represents a value below which a patient is predicted to respond or not respond and above which a patient is predicted to respond in the opposite manner of those whose scores fell below the cut-off value; using a statistical method to analyze the difference between the clinical endpoint periods for patients whose test value was at or below the cut-off and the clinical endpoint periods for those patients whose test value was above the cut-off; and selecting the cut-off value that results in the greatest percentage of patients who are predicted not to respond to the therapy amongst the group of candidate cut-off values that indicates there is a statistically significant difference between the group of patients above and below the cut-off value.

In another aspect, the invention provides a method of predicting the efficacy of a therapeutic on an individual subject, by recording the test result values for a group of individual subjects who have the same disease and were tested with the same therapeutic, and determining the percentile rank of an individual subject's test value, wherein the percentile rank of an individual subject's test value is predictive of the efficacy of the therapeutic agent for the disease in the individual subject. In one embodiment, the method includes compiling the recorded test result values into a list, and ordering the list on the basis of test results values for the individual subjects tested on the basis of each individual subject's absolute numeric test value.

In another aspect, the invention provides a kit comprising: a container for a disease cell sample from an individual subject containing a transport medium; a container for a control cell sample from the individual subject containing a transport medium; a biosensor; and a non-transitory computer readable medium having computer executable instructions for converting data from the biosensor into an output, wherein the output shows a change in a cellular physiological response parameter over a defined period of time, wherein the cellular physiological response parameter is selected from the group consisting of pH, cell adhesion, cell attachment pattern, cell proliferation, cell signaling, cell survival, cell density, cell size, cell shape, cell polarity, $O_2$, $CO_2$, glucose, cell cycle, anabolism, catabolism, small molecule synthesis and generation, turnover, and respiration, ATP, calcium, magnesium, and other charged ions, proteins, specific pathway member molecules, DNA and or RNA in various cellular compartments, genomics, and proteomics, post-translational modifications and mechanisms, levels of secondary messenger, cAMP, mRNA, RNAi, microRNAs and other RNA with physiologic function and combinations thereof; classifying the output as no response, weakly responsive, and responsive; and generating a report with the classification.

In yet another aspect, the invention provides a method of evaluating whether a first agent that is a targeted therapeutic has an effect on a signaling pathway it is intended to address in a sample of viable cancer cells obtained from a subject in order to determine whether the targeted therapeutic is functional in the subject's cancer cells, comprising;

culturing a sample of viable cancer cells obtained from the subject in a media free of agents that stimulate the signaling pathway addressed by the targeted therapeutic to produce a cultured cancer cell sample in which the cells are synchronized with respect to physiological state and pathway stimulation;

contacting the sample with the first agent and with a second agent that is known to selectively affect the signaling pathway the first agent is intended to address, so as to upregulate or downregulate the signaling pathway as measured by an effect on cell adhesion or attachment, to produce a sample contacted with both the first agent and the second agent;

continuously measuring cell adhesion or attachment of viable cells in the sample contacted with both the first agent and the second agent, relative to a sample of viable cancer cells obtained from the subject which sample is contacted with the first agent or the second agent alone; and determining by mathematical analysis of the continuous measurements whether a change in cell adhesion or attachment has occurred in the sample contacted with both the first agent and the second agent, as compared to the sample contacted with the first agent or the second agent alone; and selecting for therapeutic use in the subject a first agent that in combination with the second agent causes a change in cell adhesion or attachment, as compared to the first or second agent alone, indicating a change in the cell signaling pathway and thus that the targeted therapeutic is predicted to be functional in the subject's cancer cells.

In yet another aspect, the invention provides a method of identifying cell pathway components affected by perturbing and/or therapeutic agents in an individual subject, comprising:
- contacting an isolated, label-free cellular sample obtained from the subject with a perturbing agent and/or a therapeutic agent;
- monitoring the effect of the agents by continuously measuring at least one physiological response parameter in viable cells in the sample;
- determining by analysis of the continuous measurements whether a change in the physiological response parameter occurs, thereby characterizing the sensitivity of the sample to the agent(s);
- analyzing components of a cell pathway targeted by the agent(s) using methods selected from proteomics, qPCR, genomics, RNA quantification, tandem liquid chromatography-mass spectroscopy, and metabolomics, thereby determining whether components of the cell pathway are altered by the presence of the perturbing agent and/or the therapeutic agent in the cellular sample.

In one embodiment of this method, the activity of the perturbing agent is halted prior to analyzing the components of the cellular pathway.

In yet another aspect, the invention provides a method of determining the functional status of a cellular pathway in diseased cells obtained from an individual subject for the purpose of defining their disease at a functional level, comprising:
- contacting a diseased cell sample obtained from the subject with a perturbing agent known to agonize or antagonize a cellular pathway when the pathway is functioning normally;
- continuously measuring one or more physiological response parameters in viable cells in the sample; and
- determining by analysis of the continuous measurements whether a change in one or more physiological response parameters occurs in the diseased cell sample in the presence of the perturbing agent, relative to a suitable baseline or control;
- wherein a change in one or more physiological response parameters in the presence of the perturbing agent, relative to a suitable baseline or control, indicates that the cellular pathway targeted by the perturbing agent is functional in the individual subject.

BRIEF DESCRIPTION OF THE FIGURES

FIGS. 1A, 1B, and 1C show the results of a "CELx" test performed with cells from two HER2 overexpressing breast cancer patients (Patient B1 and B4), two targeted pathway drugs (Lapatinib and Trastuzumab) that are indicated for HER2 positive breast cancers, and human epidermal growth factor (EGF). The physiologic change of the B1 and B4 cells during the test was measured with a cellular response measurement system (CReMS) and the output from the CReMS is what is recorded in the figure. One sample each of B1 and B4 cells was pre-treated with Lapatinib and another sample each of B1 and B4 cells was pre-treated with Trastuzumab and the physiologic response of each set of cells to subsequent EGF stimulation is recorded on a continuous basis throughout the test. The CELx Pathway Shutdown test shown in FIG. 1A predicts that Patient B1 will not respond to trastuzumab but will respond to Lapatinib. The results shown in FIG. 1B also predict that Patient B4 would respond to both trastuzumab and lapatinib. The comparison of the CELx test prediction and the result recorded by third party clinical reference is shown in FIG. 1C; it shows that the CELx test accurately predicted the results recorded by the clinical reference standard, where Patient B1 was found unresponsive to trastuzumab and responsive to lapatinib and Patient B4 was found responsive to both.

FIGS. 2A, 2B, and 2C show the results of a CELx test performed with cells from two breast cancer patients (Patients B1 and B2) and the anti-proliferative drug Paclitaxel. The physiologic change of the B1 and B2 cells during the test was measured with a CReMS and the output from the CReMS is what is recorded in the figure. One set each of the B1 and B2 cells were treated with Paclitaxel and another control set of B1 and B2 cells received no drug; the physiological response of each set of cells was recorded continuously over the course of 48 hours. The B2 test cells showed initial responsiveness to Paclitaxel, as reflected in the significant decrease in CReM output compared to the B2 control cells, but after roughly 24 hours, the CReM output reverses, indicating that the test cells begin proliferating and are no longer responsive to the drug. The B1 test cells show immediate and continuous responsiveness to Paclitaxel, as reflected in the decrease in CReM output compared to the B1 control cells throughout the test period. The CELx test results presented in FIGS. 2A and 2B predict that both patients B1 and B2 will respond to paclitaxel. The comparison of the CELx test prediction and the result recorded by third party clinical reference is shown in FIG. 2C; it shows that the CELx test accurately predicted the results recorded by the clinical reference standard, where Patients B1 and B2 were both found responsive to paclitaxel.

FIGS. 3A, 3B, and 3C show the results over the entire time course of the experiment of a CELx test performed with cells from two colon cancer patients (Patients C1 and C2), EGF, and a combination of two drugs indicated for colon cancer, cetuximab and irinotecan. The physiologic change of the C1 and C2 cells during the test was measured with a CReMS and the output from the CReMS is what is recorded in the figure. One set each of C1 and C2 test cells were treated with Cetuximab and Irinotecan and another set of control C1 and C2 cells received no drug; the physiological response of each set of cells was recorded continuously. Both the C1 and C2 test cells showed responsiveness to the drug combination as reflected in the reduced CReMS output for the test cells compared to their respective control cells. These results predict that both patients C1 and C2 will respond to the combination of cetuximab and irinotecan. The comparison of the CELx test prediction and the result recorded by third party clinical reference is shown in FIG. 3C; it shows that the CELx test accurately predicted the results recorded by the clinical reference standard, where Patients C1 and C2 were both found responsive to the cetuximab and irinotecan combination.

FIG. 4 shows the summary results of 57 CELx tests performed using some of the cell and drug combinations possible from a selection of 11 different patient cells (breast cancer cells from Patients B1, B2, B3, B4, B5, B6, B7, colon cancer cells from Patients C1 and C2, and lung cancer cells from Patients L1 and L2) and 15 different drugs (capecitabine, cetuximab, docetaxel, fluorouracil, gefitinib, GSK1059615, GSK1120212, lapatinib, paclitaxel, pazopanib, trastuzumab, topotecan, cisplatin, erlotinib, and oxiliplatin). FIG. 4 also shows the results from two CELx Combination tests performed using the drug combination of paclitaxel and cisplatin on Patient L1 and L2 cells and four CELx tests with the drug combination of trastuzumab and lapatinib on Patient B1, B2, B3, and B4 cells. A total of sixteen different drugs that target 11 different cellular pathways were introduced to cell samples in this set of experiments. For each experiment, the change of the test cells' physiologic response compared to its control cells was calculated. Each box in FIG. 4 classifies the change in physiologic response measured in each experiment as either being greater than 50% (solid box), between 5%-50%, (vertical shaded box), less than 5% (horizontal shaded box), or not tested (open box). The series of experiments represented in this figure illustrate the CELx test's ability to measure the physiologic change that occurs in a variety of cancer cell types after they are exposed to wide range of drugs.

FIG. 5 shows the summary results of eight CELx tests performed separately on cells from four breast cancer patients (B1, B2, B3, and B4) with the drug Cetuximab and EGF. One set of tests on cells B1, B2, B3, and B4 was performed using an "Optical" biosensor CReMS and another set of tests on the same cells was performed using an "Impedance" biosensor CReMS. The results are presented in a summary fashion showing the range of percentage change in output recorded by the CReMS. For each patient cell tested, the amount of physiologic change recorded by each CReMS was identical. These results illustrate that the CELx test method can utilize different types of CReMS' that measure different physiologic changes in cells.

FIG. 6 provides the summary results of the 65 tests described in Examples 1-4. A total of 16 different drugs that target 11 different cellular pathways were introduced in this set of experiments to cell samples from 11 patients with three different types of cancer. For each experiment, the change of the test cells' physiologic response compared to its baseline, or control cells, was calculated. Each box in FIG. 6 classifies the change in physiologic response measured in each experiment as either being greater than 50%, between 5%-50%, or less than 5%. The CELx test predicts a positive patient response to the therapy when the change in physiologic response is between 5%-50% or greater than 50% and it predicts no patient response to the therapy when the change in physiologic response is less than 5%. The responses are shown as follows: greater than 50% (solid box), between 5%-50%, (vertical shaded box), less than 5% (horizontal shaded box), or not tested (open box). The series of experiments represented in this figure illustrate the CELx test's ability to measure the physiologic change that occurs in a variety of cancer cell types after they are exposed to wide range of drugs that affect a wide range of cellular pathways.

FIG. 7 records the correlation (either 0% or 100%) between the CELx test predictions described in FIG. 6 (test cell response to individual drugs) and results from third parties that recorded the patient's responsiveness to the drug. The solid boxes represent 100% concordance between test results on the cell sample for response or nonresponse to the therapeutic agent and the known status of the cell sample, a blank box is not tested, and a gray shaded box represents no concordance with the known cell sample status for response or non response to the therapeutic agent. In tested cases, the CELx test and the third parties generated the same result except in one case, illustrating the power of the CELx test to predict breast, lung, and colon patient response to 16 different drugs that target a wide range of cellular pathways.

FIGS. 8A, 8B, 8C and 8D record the CELx test results for different patient cancer cells and drugs versus results from third parties that recorded the patient's responsiveness to the drug. FIG. 8A records the comparison of results for all 12 cancer patient cells and 16 different drugs that were tested. FIG. 8B records the comparison of results for the eight breast cancer patient cells that were tested singly and in combination with thirteen different drugs. FIG. 8C records the comparison of results for the two different colon cancer patient cells that were tested singly and in combination with three different drugs. FIG. 8D records the comparison of results for the two different lung cancer patient cells that were tested singly and in combination with three different drugs. In each Figure, the CELx tests are shown to predict accurately whether a patient will or will not respond to a particular drug or combination of drugs except in one case.

FIG. 9 records the sensitivity and specificity of the CELx test for all the patient cells and drug tested as well as for the sub-groups of patients, drugs, pathways, and CReMS types tested. Overall and within each of the sub-groups studied, the CELx test generated high sensitivity (98%+) and specificity (99.9%+). These results illustrate the predictive power of the test across different cancer cell types, drug types, CReMS types, and pathways targeted.

DETAILED DESCRIPTION

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference. The following terms, as used herein, are intended to have the following definitions.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5).

The term "activator," "activate," or "perturbant," "perturb," "perturbation'" in conjunction with respect to cells refer to the specific subject or activity of physiologic manipulation of a cell using reagents, approved drugs, experimental compounds and drug like molecules and experimental drugs in development, organic molecules, signaling factors, biochemicals, nucleic acids, or proteins that have an effect on cells well known to those practiced in the art. The effect refers to any modulation of cellular physiologic activity and may include but not be limited to up or down-regulation.

The term "adhesion" can describe any number of molecules responsible for connecting a cell to an ECM or to other cells directly, indirectly, and or indirectly by pathway communication. For example, Integrins are responsible for cytoskeletal organization, cellular motility, regulation of the cell cycle, regulation of cellular of integrin affinity, attachment of cells to viruses, attachment of cells to other cells or ECM. Integrins are also responsible for signal transduction, a process whereby the cell transforms one kind of signal or stimulus into another- intra- and inter-cellularly. Integrins can transduce information from the ECM to the cell and information from the cell to other cells (e.g., via integrins on the other cells) or to the ECM. The combination of the α- and β-subunits determines the ligand specificity of the integrin. Many integrins have binding specificities for the same ligands and it is the combination of the integrin expression/activation pattern and the availability of ligand that specifies the interactions in vivo. Adhesion can change in density within a cell area or area of a population of cells. Adhesion can change in quantity within a cell or population of cells. Adhesion can change in quality by specificity or protein types involved in the adhesion process. Adhesion can change in polarity.

The term "assay" or "assaying" refers to an analysis to determine, for example, the presence, absence, quantity, extent, kinetics, dynamics, or type of a target, such as a cell's optical or bioimpedance response upon stimulation with exogenous stimuli (e.g., therapeutic agent).

The terms "attach," or "attachment," refer to, for example, a surface modifier substance, a cell, a ligand candidate compound, and like entities of the disclosure, connected to a surface, such as by physical absorption, chemical bonding, chemical attraction, and like processes, or combinations thereof. Particularly, "cell attachment," "cell adhesion," or "cell sample attachment" refer to the binding of cells together or interacting to a surface, such as by culturing, or interacting with a cell anchoring material, or the like.

The term "attachment pattern" refers to observable traits or characteristics of a cell or cell sample's connection to a surface. An attachment pattern can be quantitative, e.g., number of attachment sites. An attachment pattern can also be qualitative, e.g., preferred molecular site of attachment to an extracellular matrix.

The term "antibody" is used in the broadest sense and specifically includes monoclonal antibodies (including full length monoclonal antibodies), humanized antibodies, chimeric antibodies, multispecific antibodies (e.g., bispecific antibodies), and antibody fragments that exhibit a desired biological activity or function.

Antibodies can be chimeric, humanized, or human, for example, and can be antigen-binding fragments of these. "Antibody fragments" comprise a portion of a full-length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies such as bispecific antibodies, for example formed from antibody fragments. "Functional fragments" substantially retain binding to an antigen of the full-length antibody, and retain a biological activity. Antibodies can be "armed" or "conjugated" by combining with one or more other drugs through covalent or other attachment to achieve greater potency, specificity, and efficacy than the individual drug molecules could achieve separately.

The term "monoclonal antibody" as used herein refers to an antibody obtained from a population of substantially homogeneous antibodies, i.e., the individual antibodies of the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

The term "immunocapture reagents" refers to any type of antibody and additionally includes aptamers composed of RNA, DNA, and polymers containing synthetic variants of bases, or any synthetic molecule where the aptamer or reagent has been constructed and selected to specifically recognize and bind another molecule and signal its presence, quantity, and or quality.

The term "culturing" refers to preparation of cells to perform the present invention. The preparation can include at different times in the practice of the current invention, various media, media supplements, various conditions of temperature, humidity, CO2%, O2%, seed densities, cell type purity or mixtures and other conditions known to those practiced in the art of cell culture. The preparation may include conditions that allow the cells to proliferate, become quiescent, senesce, and enter, pass or are checked at various stages of cell cycle. The culturing may include any number of media or supplements known to those practiced in the art such as but not limited to vitamins, cytokines, growth factors, serums (Ex. source animal is bovine, fetal bovine, human, horse or other mammal), metabolites, amino acids, trace minerals, ions, pH buffers, and or glucose, that allow and or optimize the ideal practice of the present invention. Culturing the cells may be practiced with serum-free and or perturbant-free media before or following perturbation by the present invention. The culturing may ideally comprise conditions designed to mimic the tumor microenvironment of the patient. The culturing preparation may ideally comprise conditions that are designed to place particular pathways into a basal or heightened level to permit the measurement of agonism or antagonism of the pathway activity.

"Chimeric" antibodies (immunoglobulins) contain a portion of a heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., 1984, *Proc. Natl. Acad. Sci. USA* 81:6851-6855).

The term "humanized antibody", as used herein, are antibodies that contain minimal sequence derived from nonhuman immunoglobulin. For the most part, humanized antibodies are human immunoglobulins (recipient or acceptor antibody) in which variable domain hypervariable region residues of the recipient antibody are replaced by hypervariable region residues from a nonhuman species (donor antibody), such as mouse, rat, rabbit, or nonhuman primate having the desired specificity, affinity, and capacity. The hypervariable regions can be complementarity-determining regions (CDRs) defined by sequence (see, for example Kabat 1991, 1987, 1983), or hypervariable loops (HVLs) defined by structure (see for example, Chothia 1987), or both.

A "biomolecular coating" is a coating on a surface that comprises a molecule that is a naturally occurring biomolecule or biochemical, or a biochemical derived from or based on one or more naturally occurring biomolecules or biochemicals. For example, a biomolecular coating can comprise an extracellular matrix component (e.g., fibronectin, collagens, laminins, other glycoproteins, peptides, glycosaminoglycans, proteoglycans, vitronectin, Intercellular-CAMs, VascularCAMs, MAdCAMs), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occurring biochemicals. Coatings can also include cell surface receptor or cell surface cognate binding proteins or proteins with affinity for said cell surface proteins.

The term "baseline measurement" refers to a physiologic beginning point for a set of cells to be tested and is based on an evaluation of measurements over a period of time before drug is added. This may include a basal cellular metabolism measurement or CReMS reading prior to exogenous perturbation. This may alternatively include but not be limited to include the CReMS measurement of a normal healthy cell metabolic function with or without exogenous perturbation.

The term "basal morphology" refers to the form and structure of a cell or cell sample prior to the introduction of an agent or stimulus.

The term "cell adhesion" refers to the binding of a cell to another cell, to an extracellular matrix component, or to a surface (e.g., microtiter plate).

The term "Cellular Response Measurement System" or "CReMS" refers to a device that can quantitatively determine a change in a physiological or cellular response parameter in a cell, in and between cells, and between cells and the instrumentation device. In embodiments the cell is a whole label free cell. A change in a physiological or cellular response parameter is measured by determining change in an analyte such as glucose, oxygen, carbon dioxide, amine containing materials such as proteins, amino acids, or of the extracellular matrix, or of a cell signaling molecule, or of cell proliferation, cell morphology, or cytoskeletal rearrangement. An example of a CReMS is a biosensor.

The term "CReMS Signal" as used herein is defined as a measure of cellular physiologic change of cells when those cells are analyzed by a chemo-electric CReMS. The CReMS signal and changes in the CReMS signal can have various units as related to the particular chemo-electric transducer measuring the physiologic change. For example, the CReMS signal may have units of but not be limited to cell index, impedance, wavelength units, pH units, voltage, current, or become dimensionless by using ratios of the units. Any of these units may have a time component. The CReMS signal can be mathematically modified for clarity of interpretation as is frequently done by those practiced in the art of biology, biochemistry and biophysics, for example including normalization, baselining, curve subtracting, or any combination of these. The CReMS signal may be measured at a single time point, or, more preferably, over a continuous series of time points representing a complete pattern of cellular physiologic response.

The term CReM "optical signal" is defined as the wavelength value or change in wavelength value measured as light is reflected from the photonic crystal biosensing CReMS upon which the cells rest. The units are typically in picometers or nanometers though could also become dimensionless if ratios of changes are reported. The "optical signal" could be expressed in said units combined with time. The shift in reflected wavelengths of light is proportional to the mass upon the photonic crystal surface. Thus the "optical signal" is a quantitative measure of the number of cells on the CReMS. Furthermore, the "optical signal" is a measure of the cell physiological status as for example changes in cell morphology, cell adhesion, cell viability, structural rearrangements of the cell lead to differences in the amount of mass upon the sensor that are detected as wavelength shifts.

The term "Cell Index" as used herein is defined as a measurement of impedance and can be applied in one instance of the present invention by measuring at a fixed electrical frequency of, for example, 10 kHz and fixed voltage.

And calculated by the equation Cell $Index_i = (R_{tn} - R_{t0})/F$

Where:

i=1, 2, or 3 time point

F=15 ohm in one example when the instrument is operated at 10 kHz frequency $R_{t0}$ is the background resistance measured at time point T0.

$L_{tn}$ is the resistance measured at a time point Tn following cell addition, cell physiologic change, or cell perturbation. Cell index is a dimensionless parameter derived as a relative change in measured electrical impedance to represent cell status. When cells are not present or are not well-adhered on the electrodes, the CI is zero. Under the same physiological conditions, when more cells are attached on the electrodes, the CI values are larger. CI is therefore a quantitative measure of cell number present in a well. Additionally, change in a cell physiological status, for example cell morphology, cell adhesion, or cell viability will lead to a change in CI.

The term "biosensor" refers to a device that measures an analyte or a change in an analyte or physiologic condition of a cell. In embodiments, the biosensor typically contains three parts: a biological component or element that binds or recognizes the analyte (including non-limiting examples such as extracellular matrix, cell signaling molecule, or cell proliferation, tissue, cells, metabolites, catabolites, biomolecules, ions, oxygen, carbon dioxide, carbohydrates, proteins etc.), a detector element (operating in a physicochemical manner such as optical, piezoelectric, electrochemical, thermometric, or magnetic), and a transducer associated with both components.

The term "optical biosensor" refers to a device that measures fluorescence, absorption, transmittance, density, refractive index, and reflection of light. In embodiments, an optical biosensor can comprise an optical transducer for converting a molecular recognition or molecular stimulation event in a living cell, a pathogen, or combinations thereof into a quantifiable signal. Additionally, embodiments could include a photonic crystal device, an optical waveguide device, and a surface plasmon resonance device.

The term "impedance biosensor" refers to a device that measures complex impedance changes (deltaZ, or dZ) of live patient cells where impedance (Z) is related to the ratio of voltage to current as described by Ohm's law (Z=V/I). It is sensitive to the local ionic environment at the electrode interface with the cells and detects these changes as a function of voltage and current fluctuations. Physiologic changes of the cells as a result of normal function or perturbation thereof result in quantifiable changes to the flow of current around the electrodes and influence the magnitude and characteristics of the signal measured. In embodiments, an impedance biosensor can comprise electrodes or an electrical circuit for converting a molecular recognition or molecular stimulation event in a living cell, a pathogen, or combinations thereof into a quantifiable signal. In embodiments, an ISFET biosensor can comprise an ion selective field effect electrical transducer for converting an analyte recognition or cellular stimulation event in a living cell, a pathogen, or combinations thereof into a quantifiable signal. When an analyte concentration in an ISFET biosensor changes, the current in the transistor changes, which creates a quantification signal.

The term "cell signaling" refers to the intracellular or intercellular transfer of information. Cells signaling can be achieved by direct contact between cells or by the release of a substance from one cell that is taken up by another cell. Intercellular signaling can occur via an interaction between two molecules (e.g., a ligand and a receptor). Receptor binding can trigger a cascade of intracellular signaling (e.g., initiation of biochemical changes within the cell or modification of the membrane potential).

The term "cytoskeletal organization" refers to the arrangement of the internal scaffold of a cell. A cell's cytoskeleton comprises filaments that serve to support cytoplasmic or membrane elements and/or intracellular organelles. The cytoskeleton also helps to maintain the shape of a cell.

The term "cell proliferation" refers to an increase in the number of cells as a result of cell growth and cell division.

The term "cell survival" refers to the viability of a cell characterized by the capacity to perform certain functions such as metabolism, growth, movement, reproduction, some form of responsiveness, and adaptability.

The term "efficacy" refers to the extent to which a specific intervention produces a beneficial result. In embodiments, the intervention can be a therapeutic agent, such as a small molecule or an antibody. A beneficial result includes without limitation an inhibition of symptoms, a decrease in cell growth, an in increase in cell killing, a decrease in inflammation, and an increase in immune responsiveness.

An "extracellular matrix component" is a molecule that occurs in the extracellular matrix of an animal. It can be a component of an extracellular matrix from any species and from any tissue type. Non-limiting examples of extracellular matrix components include laminins, collagens, fibronectins, other glycoproteins, peptides, glycosaminoglycans, proteoglycans, etc. Extracellular matrix components can also include growth factors.

The term "global phenotype" refers to a plurality of observable properties of a cell or cell sample as a whole. A global phenotype may include but not be limited to cell size, cell shape, distinctive protuberances, outgrowths, spreading, attachment foci density, cytoskeletal arrangements, cell proliferation patterns, receptor phagocytosis, or attachment foci number, changes in pH, uptake or efflux of metabolites, signaling proteins and growth factors, oxygen, $CO_2$, glucose, ATP, and ions such as magnesium, calcium, potassium.

The term "event specificity" refers to a physical observation of a specific property of a cell. Such specific properties relate to a specific cellular function, exogenous perturbation, or pathway agonsim/antagonism as part of the intended and/or expected physiological response of the cell to a particular activator or therapeutic agent. Activators and therapeutic agents may be known to be targeted to affect a certain aspect of the cell function such as cytoskeletal structure, or a cellular pathway. The physically observable event is called event specificity because the physically observable event in the cell in the presence of the activator or the therapeutic agent is a reflection of the intended and/or expected effect the activator or therapeutic agent on the cell. For example, the addition of vinblastine to most cell samples on an attachment biosensor type of CReMS produces a profound reduction in signal. Vinblastine is a cellular cytoskeletal scaffolding disrupter. The reduction in signal is a physically observable event of the cell linked specifically to loss of cell shape and attachment caused by the drug action at microtubule molecules.

The term "Impedance" as used herein is defined by a physical law relating voltage and current by the equation: Impedance (ohm)=Voltage (volts)/Current (amperes) or $Z=V/I$.

"Mammal" for purposes of treatment or therapy refers to any animal classified as a mammal, including humans, domestic and farm animals, and zoo, sports, or pet animals, such as dogs, horses, cats, cows, and the like. Preferably, the mammal is human.

The term "microcantilever device", "microcantilever array", or microcantilever apparatus" refers to a type of CREMS instrument comprising at least one cantilever, a flexible beam that may be bar-shaped, V-shaped, or have other shapes, depending on its application. One end of the microcantilever is fixed on a supporting base, another end standing freely. Microcantilevers can measure concentrations using electrical methods to detect phase difference signals that can be matched with natural resonant frequencies (examples as described in U.S. Pat. No. 6,041,642, issued Mar. 28, 2000, which is hereby incorporated by reference) Determining a concentration of a target species using a change in resonant properties of a microcantilever on which a known molecule is disposed, for example, a macromolecular biomolecule such as DNA, RNA, or protein. Deflection is measured using optical and piezoelectric methods.

The term "normal functioning" refers to pathways in healthy cells that have a defined system of checks and balances that prevent healthy cells from becoming dysfunctional from unnatural levels of signaling, replication, loss of contact inhibition, and aberrant gene copying and amplification. In many cases, with pathways beginning in some quiescent or steady basal state, addition of small amounts of perturbant at the pathway members' EC50 concentration will have only a small transient effect as the cell system recognizes the perturbant, initiates the pathway activity, and then downregulates the perturbant effect to maintain balance with other cellular function. Diseased function often is recognizable as over-reaction to a perturbant, hyper/hypo activity along the pathway, inappropriate inter-pathway activity to accommodate the perturbant effect, and failure to downregulate the minimal perturbant effect. Additionally, with some diseased states, a basal state for some pathway members cannot be reached for a pathway. These systems are described as constitutively activated.

The terms "abnormal signaling pathway" or "dysfunctional signaling pathway" are used interchangeably and refer to a cell signaling pathway that has been disrupted in such a way as to impair the ability of the cell to perform its normal function. The source of the cell signaling disruption and resulting dysfunction is typically a consequence of damage to the genome that interferes with the signaling pathways' normal function. This damage can be the result of endogenous processes such as errors in replication of DNA, the intrinsic chemical instability of certain DNA bases or from attack by free radicals generated during metabolism. Some inactivating mutations occur in genes responsible for maintaining genomic integrity facilitating the acquisition of additional mutations. Additional mechanisms that affect the genomic level of cellular control involve epigenetic mechanisms whereby the expression of specific genes has been altered by changes to the histone proteins' function. The epigenome function has been demonstrated to be highly adaptive or responsive to many different environmental conditions including conditions that participate in disease etiology and propagation. Various RNA-based mechanisms of pathway dysfunction have been described at the transcriptional, post-transcriptional, translational, and post-translational levels.

Additionally, many actions of pathway dysfunction at the protein level are known to those skilled in the art of cellular molecular biology. Pathway dysfunction can be the result of over or under expression of a pathway member or members or co-factor(s), protein activity present in unnatural cell types or cellular locations, protein interaction with unnatural pathway members also known as pathway cross-reactivity, dysfunctional feedback loops. Pathway dysfunction can additionally be the result of activity of the proteome, proteasome, kinome, metabolome, nuclear proteins and factors, cytoplasmic proteins and factors, and or mitochondrial proteins and factors.

When cells with dysfunctional pathways replicate, they can pass on the abnormality to their progeny, which increases the likelihood that the cells become diseased. By analyzing the activity of a cell signaling pathway in live cells, it is possible to determine whether the signaling pathways of the cells are functioning normally or abnormally.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR.sub.2 ("amidate"), P(O)R', P(O)OR', CO or CH.sub.2 ("formacetal"), in which each R or R' is independently H or substituted or unsubstituted alkyl (1-20 C) optionally containing an ether (—O—) linkage, aryl, alkenyl, cycloalkyl, cycloalkenyl or aralkyl. Not all linkages in a polynucleotide need be identical. The preceding description applies to all polynucleotides referred to herein, including RNA and DNA.

"Polypeptide" refers to a peptide or protein containing two or more amino acids linked by peptide bonds, and includes peptides, oligomers, proteins, and the like. Polypeptides can contain natural, modified, or synthetic amino acids. Polypeptides can also be modified naturally, such as by post-translational processing, or chemically, such as amidation, acylation, cross-linking, and the like.

The term "quartz crystal resonators/microbalance" refers to a type of CREMS device that measures mass by measuring the change in frequency of a piezoelectric quartz crystal when it is disturbed by the addition of a small mass such as a virus or any other tiny object intended to be measured. Frequency measurements are easily made to high precision, hence, it is easy to measure small masses.

As used herein, "sample" refers to anything which may contain a moiety to be isolated, manipulated, measured, quantified, detected or analyzed using apparatuses, microplates or methods in the present disclosure. The sample may be a biological sample, such as a biological fluid or a biological tissue. Examples of biological fluids include suspension of cells in a medium such as cell culture medium, urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbohydrates, chemical molecules binding to biological molecules).

The term "cell sample" refers to cells isolated from a particular subject, where the cells are isolated from a subject's biological fluids, excretions, or tissues. Cells isolated from tissue can include tumor cells. Cells isolated from tissue include homogenized tissue, and cellular extracts, and combinations thereof. Cell samples include isolation from, but are not limited to, blood, blood serum, blood plasma, urine, semen, seminal fluid, seminal plasma, prostatic fluid, pre-ejaculatory fluid (Cowper's fluid), excreta, tears, saliva, sweat, biopsy, ascites, cerebrospinal fluid, lymph, marrow, or hair.

The term "CELx" test refers generally to the various embodiments of the methods described herein.

The term "disease cell sample" refers to a plurality of cells from the site of disease or cells that have the characteristic of disease.

The term "healthy cell sample" refers to a cell sample wherein the cells do not have or are extracted from a tissue that does not have the disease that is being tested. For example, when a particular subject is being tested for the effects of a therapeutic agent against the subject's breast cancer, non-cancerous cells or cells from non-breast tissue are considered "healthy". The term "healthy cell sample" is not a determination or reflection upon the whole health status of the subject.

The term Analytical "Sensitivity" refers to a test or the detection limit, and is defined as the lowest quantity differentiated from Zero. (e.g. 95% confidence intervals or 2 standard deviations (SD) above the mean of the Zero control are commonly used).

The Term Clinical "Sensitivity" refers to the proportion of subjects with the target condition in whom the test is positive or how often the test is positive when the condition of interest is present. Clinical "Sensitivity" of a test is defined as an estimate of accuracy provided by the calculation: 100%×TP/(TP+FN) where TP is the number of True Positive events for an outcome being tested and FN are the number of False Negatives events, incorrectly determined events as negative.

Clinical "Specificity" refers to the proportion of subjects without the target condition in whom the test is negative or how often the test is negative when the condition of interest is absent. Clinical specificity is estimated by the calculation: 100%×TN/(FP+TN) where TN is the number of True Negative events for an outcome being tested and FP is the number of False Positives, incorrectly determined events as positive.

The term "surface plasmon resonance device" refers to an optical biosensor type of CReMS that measures binding events of biomolecules at a metal surface by detecting changes in the local refractive index.

The term "therapeutic agent" refers to any synthetic or naturally occurring biologically active compound or composition of matter which, when administered to an organism (human or nonhuman animal), induces a desired pharmacologic, immunogenic, and/or physiologic effect by local and/or systemic action. The term encompasses those compounds or chemicals traditionally regarded as drugs, vaccines, and biopharmaceuticals including molecules such as proteins, peptides, hormones, nucleic acids, gene constructs and the like. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment. Therapeutic agents include, but are not limited to, anticancer therapeutics, antipsychotics, anti-inflammatory agents, and antibiotics.

The term "targeted pathway drug," "pathway drug," or "targeted drug," refers to any molecule or antibody with therapeutic capacity designed to bind to a specific biomolecule (eg. protein) involved in a disease process, thereby regulating its activity.

The term "anti-proliferative drug," "anti-proliferative agent," or "apoptosis inducing drug," refers to any molecule or antibody with therapeutic capacity that functions to reduce cell division, reduce cell growth, or kill cells. In many cases, the activity of these drugs is directed towards broad classes of biomolecules (eg. DNA intercalation) involved in normal cellular processes and thus the drug may be less discriminant towards cell disease status.

A "variant" of a polypeptide refers to a polypeptide that contains an amino acid sequence that differs from a reference sequence. The reference sequence can be a full-length native polypeptide sequence or any other fragment of a full-length polypeptide sequence. In some embodiments, the reference sequence is a variable domain heavy chain or variable domain light chain consensus sequence. A polypeptide variant generally has at least about 80% amino acid sequence identity with the reference sequence.

B. Methods of Selecting or Monitoring Efficacy of a Therapeutic Agent

A disease like cancer is heterogeneous in part because cancer in one individual can be completely different from the same cancer in another individual in genetic makeup, protein expression levels, and response to therapeutic intervention. Even diseased tissues can vary considerably from one another in gene expression or gene alterations. For example, metastatic tumors may differ from primary tumors. Human genome sequencing and other genetic quantification tools have informed doctors that each patient's disease is somewhat unique to that patient. This information has spawned a whole business around personalized medicine, where each patient could potentially receive a therapeutic regimen customized for their disease.

Some drugs are being targeted for specific gene-related disease indications. This approach has not yet been broadly utilized due primarily to significant shortcomings of the current prognostic toolset. The methods as described herein provide for a method of selecting a therapeutic agent that shows efficacy against an individual's disease. In embodiments, the therapeutic agent is contacted to isolated label free live whole cells from diseased tissue in a CReMS and a change or lack thereof in a physiologic parameter of the cells is detected in the presence of the therapeutic agent. A therapeutic agent is selected to treat the subject that results in a change in a physiological parameter of the disease cell as compared to a baseline measurement.

One aspect of the disclosure includes methods of selecting one or more therapeutic agents, including drugs that are commercially approved for use to treat a disease or disorder, either at the initial diagnosis or throughout treatment of a subject. In embodiments, the method comprises administering one or more therapeutic agents to at least one isolated disease cell sample from the subject in a cellular response measurement system; determining whether a change occurs in cellular response parameter of the disease cell sample in response to the therapeutic agent or agents as compared to a baseline measurement of the cellular response parameter before administration of the therapeutic agent or agents, wherein the change in cellular response parameter indicates that the agent or agents has therapeutic efficacy for the disease in the individual subject. In certain embodiments, the isolated disease cell sample comprises label free whole cells. In other embodiments, the change of the cellular response parameter in the isolated disease cell is monitored continuously for a defined period of time. In other embodiments, the method further comprises selecting the therapeutic agent or combination of therapeutic agents that results in the change of at least one cellular response or physiologic parameter and communicating the selected agent to a health care provider. In other embodiments, the method further comprises administering the therapeutic agent or combination of therapeutic agents that results in the change of at least one cellular response or physiologic parameter.

In another embodiments, the invention provides a method of selecting treatment for an individual subject by determining the therapeutic efficacy of an agent for a disease in the individual subject comprising: administering the agent to at least one isolated label free disease cell sample from the individual subject in a cellular response measurement system (CReMS), wherein the disease cell sample is selected from the group consisting of a cancer cell sample, a cell sample from a subject with an autoimmune disease, a cell sample from a tissue infected with a foreign agent and combinations thereof; continuously measuring a change in at least one physiological response parameter of the cell sample for a defined period of time in the presence and/or absence of the therapeutic agent; and determining whether a change in a physiological response parameter of the cell sample to the agent occurs as compared to a baseline measurement, wherein the change in physiological response indicates that the agent has therapeutic efficacy for the disease in the individual subject. In embodiments, the disease cells are cancer cells.

In yet another aspect, the invention provides a method of evaluating whether a first agent that is a targeted therapeutic has an effect on a signaling pathway it is intended to address in a sample of viable cancer cells obtained from a subject in order to determine whether the targeted therapeutic is functional in the subject's cancer cells, comprising;

culturing a sample of viable cancer cells obtained from the subject in a media free of agents that stimulate the signaling pathway addressed by the targeted therapeutic to produce a cultured cancer cell sample in which the cells are synchronized with respect to physiological state and pathway stimulation;

contacting the sample with the first agent and with a second agent that is known to selectively affect the signaling pathway the first agent is intended to address, so as to upregulate or downregulate the signaling pathway as measured by an effect on cell adhesion or attachment, to produce a sample contacted with both the first agent and the second agent;

continuously measuring cell adhesion or attachment of viable cells in the sample contacted with both the first agent and the second agent, relative to a sample of viable cancer cells obtained from the subject which sample is contacted with the first agent or the second agent alone; and determining by mathematical analysis of the continuous measurements whether a change in cell adhesion or attachment has occurred in the sample contacted with both the first agent and the second agent, as compared to the sample contacted with the first agent or the second agent alone; and selecting for therapeutic use in the subject a first agent that in combination with the second agent causes a change in cell adhesion or attachment, as compared to the first or second agent alone, indicating a change in the cell signaling pathway and thus that the targeted therapeutic is predicted to be functional in the subject's cancer cells.

In the initial culturing step, the cells are cultured in the absence of any agents or factors that would stimulate the signaling pathway to be analyzed (for example, in the absence of serum and/or other growth factors that could stimulate the signaling pathway of interest) such that the cultured cells are synchronized with respect to physiological state and pathway stimulation. The cells are then contacted with both the targeted therapeutic (first agent) and the perturbing agent that selectively affects the signaling pathway (second agent). The cells can be contacted with both agents at the same time (contemporaneously) or, alternatively, the cells can be contacted with the first agent followed by the second agent or the cells can be contacted with the second agent followed by the first agent. Control samples for comparison purposes are contacted with the first agent alone or with the second agent alone. Continuous measurement of cell adhesion or attachment of the viable cells and mathematical analysis of the continuous measurement is performed to determine whether a change in cell adhesion or attachment has occurred in the sample contacted with both the first agent and the second agent, as compared to the first agent or second agent alone. Finally, a targeted therapeutic (first agent) is selected for therapeutic use in the subject in which the targeted therapeutic (first agent) in combination with the perturbing agent (second agent) causes a change in cell adhesion or attachment, as compared to the first agent alone or second agent alone, which thus indicates that the targeted therapeutic causes a change in the signaling pathway and therefore is predicted to be functional in the subject's cancer cells.

In other embodiments, the invention provides a method for comparing efficacy of therapeutic agents for a particular subject comprises administering at least two different therapeutic agents to separate disease cell samples from the same subject in a device that measures at least one physiological parameter of a cell; determining the physiologic response of each cell sample to each of the therapeutic agents compared to a baseline measurement, wherein the physiologic response indicates efficacy of each therapeutic agent. In certain embodiments, the isolated disease cell sample comprises label free whole cells. In other embodiments, the change of the cellular response parameter in the isolated disease cell is monitored continuously for a defined period of time. In embodiments, the method further comprises selecting the therapeutic agent or combination of therapeutic agents that results in better efficacy; and communicating the selection to a health care provider. In other embodiments, the method further comprises administering the therapeutic agent or combination of therapeutic agents that results in the better efficacy to the subject.

Another aspect of the disclosure provides a method to determine the growth rate of tumor cells. By measuring the growth rate of tumors, a treatment can be selected depending on how fast the tumor cells can grow. If the tumor cells are a fast growing tumor, the health care worker would select a more aggressive treatment as compared to that of a treatment for a slower growing tumor. In certain embodiments, the method comprises providing an isolated tumor cell sample in a cellular response measurement system, monitoring the growth rate of the tumor cell sample continuously over a defined period of time, and selecting a more aggressive treatment for those tumor cells that exhibit a fast growth rate and/or communicating the selected treatment to a health care provider. In other embodiments, the isolated disease cell sample comprises label free whole cells. In other embodiments, the method further comprises administering the selected treatment to the subject. In embodiments, a fast growing tumor has a cell doubling rate of less than about 100 hours, preferably less than 20 hours, whereas a slower growing tumor has a cell doubling rate that is 100 hours or more, where the cell doubling rate is the time for one cell to divide into two cells.

In another aspect, the invention provides a method for determining whether a particular pathway is active in a disease cell sample from an individual subject, and/or whether the particular pathway is sensitive to a therapeutic agent to detect the presence of the pathway in the disease cell sample. In such methods, a profile of cellular pathways functioning in the disease cell sample of the individual can be obtained and monitored over time as treatment continues. In certain embodiments, the method involves characterizing a disease cell sample for the presence or absence of pathway function by administering one or more activator agents and/or therapeutic agent to at least one isolated disease cell sample from the subject in a cellular response measurement system; determining whether a change occurs in cellular response parameter of the disease cell sample in response to the activator agent and/or therapeutic agent as compared to a baseline measurement of the cellular response parameter before administration of the activator agent and/or therapeutic agent, wherein the change in cellular response parameter indicates that the cellular pathway activated by the activator agent or inhibited by the therapeutic agent is functioning in the isolated disease cell sample from the individual subject. In certain embodiments, the activator agents include growth factors, protein or other ligands that bind to receptors and cell surface proteins such as heregulin that then activate cellular pathways, cells including transformed cells that have cell surface receptors that activate pathways in a disease cell sample, or small organic molecules (10,000 Daltons or less), peptides, nucleic acids (eg. interfering RNA) that intracellularly perturb cellular physiologic function in a desired manner. In other embodiments, the therapeutic agents include from a non-limiting list those that inhibit growth factor receptors such as EGFR, Her2, PDGFR, TGFR, FGFR, TNFR, or VEGF receptors, topoisomerase activity, kinases, G-protein coupled receptors, receptor tyrosine kinases, microtubule polymerization, cytoskeletal organization, cell function and cell adhesion.

For example, in one embodiment, a method is provided for determining the functional status of a cellular pathway in diseased cells obtained from an individual subject, by contacting a diseased cell sample obtained from the subject with a perturbing agent (e.g., an activator agent) known to agonize or antagonize a cellular pathway when the pathway is functioning normally, measuring continuously or intermittently one or more physiological response parameters in viable cells in the sample, and determining by mathematical analysis of the continuous or intermittent measurements whether a change in one or more physiological response parameters occurs in the diseased cell sample in the presence of the perturbing agent, relative to a suitable control, where a change in one or more physiological response parameters in the presence of the perturbing agent, relative to a suitable control, indicates that the cellular pathway targeted by the perturbing agent is functional in the individual subject.

Knowledge of the status of a cellular pathway in an individual subject can be used, in one embodiment, to predict responsiveness of the subject to therapeutic agents that target the cellular pathway. For example, if diseased cells from a subject are responsive to a perturbing agent (e.g., an activator agent), as determined by analysis of continuous measurements of one or more physiological response parameters in the presence of the perturbing agent, the subject will likely be responsive to therapeutic agents targeted to the same cellular pathway as the perturbing agent. Diseased cells from the subject are responsive to a perturbing agent if a change in one or more physiological response parameters occurs in viable cells of the diseased cell sample in the presence of the perturbing agent, relative to a suitable control.

In another example, if diseased cells from a subject are not responsive to a perturbing agent (e.g., an activator agent), as determined by analysis of continuous measurements of one or more physiological response parameters in the presence of the perturbing agent, the subject will likely fail to respond to therapeutic agents targeted to the same cellular pathway as the perturbing agent. Diseased cells from the subject are not responsive to a perturbing agent if a change in one or more physiological response parameters is not detected in viable cells of the diseased cell sample in the presence of the perturbing agent, relative to a suitable control.

Accordingly, in another aspect, a method is provided for selecting a targeted therapeutic agent for an individual subject, by contacting a diseased cell sample obtained from the subject with a perturbing agent known to agonize or antagonize a cellular pathway when the pathway is functioning normally, continuously measuring one or more physiological response parameters in viable cells in the sample, and determining by mathematical analysis of the continuous measurements whether a change in one or more physiological response parameters occurs in the diseased cell sample in the presence of the perturbing agent, relative to a suitable control, where a change in one or more physiological response parameters in the presence of the perturbing agent, relative to a suitable control, indicates that the subject will be responsive to a targeted therapeutic agent that targets the cellular pathway. In certain embodiments, the method further involves administration of the targeted therapeutic agent to the subject (i.e., if the subject is determined to be responsive to the agent).

In other embodiments, the method comprises administering one or more activator agents to an isolated disease cell sample from the subject in a cellular response measurement system; determining whether a change occurs in cellular response parameter of the disease cell sample in response to the activator agent over a defined period of time as compared to a baseline measurement of the cellular response parameter before administration of the activator agent, administering one or more therapeutic agents to the isolated disease cell sample and determining whether a change occurs in cellular response parameter of the disease cell sample in response to the therapeutic agent over a defined period of time as compared to the cellular response parameter before or after administration of the activator agent, wherein the change in cellular response parameter indicates that the cellular pathway activated by the activator agent and inhibited by the therapeutic agent is functioning in the isolated disease cell sample from the individual subject.

Additional embodiments include a method for selecting a subject for a treatment, a clinical trial, and/or evaluating the responsiveness of patients to a candidate therapeutic agent. In embodiments, the subject is selected prior to the clinical trial of that candidate therapeutic in order to select only those patients who are most likely to respond to the candidate therapeutic; this approach would increase the likelihood that the candidate therapeutic could demonstrate efficacy within the selected patient population sufficient to warrant regulatory approval, particularly with therapeutic agents that can only provide an efficacious result for a portion of the overall population that is diagnosed with that disease. Patients considered for a clinical trial of an unapproved therapeutic under this approach would have their diseased cells evaluated to determine their responsiveness to the drug. Only those that demonstrate responsiveness to the unapproved therapeutic agent would get selected for the trial. In other embodiments, the subject is selected for a treatment when a sample of the subject's cells is identified as a responder by a method comprising administering one or more therapeutic agents to at least one isolated disease cell sample from the subject in a cellular response measurement system; determining whether a change occurs in cellular response parameter of the disease cell sample in response to the therapeutic agent or agents as compared to a baseline measurement of the cellular response parameter before administration of the therapeutic agent or agents, wherein the change in cellular response parameter indicates that the agent or agents has therapeutic efficacy for the disease in the individual subject. In certain embodiments, the method further comprises selecting the subject whose cells exhibit a change in a cellular response parameter in response to the therapeutic agent or agents for treatment or for a clinical trial.

In a further aspect, the invention provides a method to identify biomarkers of a disease sample from a subject that demonstrates responsiveness or non responsiveness to a therapeutic agent. In one embodiment, the method involves contacting an isolated disease cell sample from a subject with a therapeutic agent in a cellular response measurement system; determining whether a change occurs in cellular response parameter of the disease cell sample in response to the therapeutic agent or agents as compared to a baseline measurement of the cellular response parameter before administration of the therapeutic agent or agents, wherein the change in cellular response parameter indicates that the agent or agents has therapeutic efficacy for the disease in the individual subject (responder) and lack of a change indicates that the therapeutic agent does not have efficacy for that subject's disease (nonresponder). In embodiments, the method further comprises further characterizing cells from a subject that are responsive to the therapeutic agent for other biomarkers and/or further characterizing cells from a subject that are not responsive to the therapeutic agent for other biomarkers. Other biomarkers comprise gene mutations, single nucleotide polymorphisms, gene expression levels, proteins, protein mutations, splice variants, cell surface markers, overexpression of a protein or nucleic acid, amplification of a nucleic acid, cell morphology, and combinations thereof.

The efficacy of a targeted therapeutic depends on whether or not it binds to its target and causes a co-incidental cellular change in signaling. The methods described herein measure the effect that a therapeutic agent and/or perturbing agent have on the pathway the agents are intended to effect by measuring a physiologic response to the agent(s) in a cell sample. Genomic and proteomic tools may be used to identify alterations in cell pathway components affected by the therapeutic agents and/or perturbing agents (e.g., activating agents). Accordingly, in one embodiment, a method is provided to identify cell pathway components affected by perturbing and/or therapeutic agents in an individual subject, by contacting an isolated, label-free cellular sample obtained from the subject with a perturbing agent and/or a therapeutic agent, monitoring the effect of the agents by continuously measuring at least one physiological response parameter in viable cells in the sample, determining by mathematical analysis of the continuous measurements whether a change in the physiological response parameter occurs, thereby characterizing the sensitivity of the sample to the agent(s), halting the activity of the perturbing agent on the sample, and analyzing components of a cell pathway targeted by the agent(s) using a method selected from proteomics, qPCR, genomics, RNA quantification, tandem liquid chromatography-mass spectroscopy, and metabolomics, in order to determine whether components of the cell pathway are altered by the agent(s) in the cellular sample. This method can be used to determine, for example, which cell pathway components undergo changes expression or activation (e.g., phosphorylation) upon stimulation of the pathway in patient cells.

These methods may also be used to compare the pathway activity of two cell samples from different tissue from the same individual subject.

In certain embodiments, the perturbing agent can be a drug, a combination of perturbing agents, a combination of perturbing agents that includes an activator and inhibitor of a pathway, a combination of perturbing agents that includes an agonist and antagonist of different members of a pathway, or a combination of perturbing agents that includes a therapeutic.

These methods may also be used to enhance the drug discovery process by evaluating whether small molecules or antibodies that are drug candidates have the effect on the pathways they are targeting.

In yet other embodiments, the invention provides a method for determining an optimal therapeutic regime or combination of drugs for a particular subject by administering a plurality of therapeutic agent combinations to separate disease cell samples from the same subject in in a device that measures at least one physiological parameter of a cell, wherein each therapeutic combination is administered to a separate disease cell sample from the same subject; and determining the physiologic response of each cell sample to each therapeutic combination compared to a baseline measurement, wherein the physiologic response indicates the most efficacious therapeutic combination of potential therapeutic combinations. In certain embodiments, the method further comprises selecting the therapeutic agent or combination of therapeutic agents that results in the change of at least one cellular response or physiologic parameter. In other embodiments, the method further comprises administering the therapeutic agent or combination of therapeutic agents that results in the change of at least one cellular response or physiologic parameter to the subject.

In another aspect, the invention provides a method that comprises treating a patient for a disease by selecting a therapeutic agent for treating the disease comprising administering one or more therapeutic agents to at least one isolated disease cell sample from the subject in a cellular response measurement system; determining whether a change occurs in cellular response parameter of the disease cell sample in response to the therapeutic agent or agents as compared to a baseline measurement of the cellular response parameter before administration of the therapeutic agent or agents, selecting the therapeutic agent that causes a change in cellular response parameter; administering the therapeutic agent that results in the change of at least one cellular response or physiologic parameter to the subject. Therapeutic agents include those that are targeted to a specific biological pathway, those that inhibit cell proliferation, those that enhance cell killing, those that inhibit inflammation, those that kill microorganisms and/or those that enhance an immune response. In certain embodiments, where the therapeutic agent is targeted to a specific biological pathway, it may interact with a cell surface receptor and inhibit the action of the ligand for the receptor. For example, some breast cancer cells are positive for an epidermal growth factor receptor (EGFR) and respond to epidermal growth factor (EGF). The efficacy of a therapeutic agent that inhibits the interaction of EGF for an individual subject's cells can be determined in the presence and absence of the ligand.

In other embodiments, the therapeutic agent inhibits cell proliferation and/or cell killing. In those cases, a rate of change in a cellular response or physiological parameter can be measured on a sample and is indicative of the therapeutic agent's efficacy for causing cell death or inhibiting cell proliferation. In embodiments, the rate of change of a cellular response is determined in the presence and/or absence of the therapeutic agent and a known agent that enhances proliferation and/or inhibits cell killing.

In other aspects of the invention, kits are provided. In one embodiment, a kit comprises: a container for a disease cell sample from an individual subject containing a transport medium; a container for a control cell sample containing a transport medium; a biosensor; and a non transitory computer readable medium having computer executable instructions for converting data from the biosensor into an output, wherein the output shows a change in a cellular physiological response parameter over a defined period of time, wherein the cellular physiological response parameter is selected from the group consisting of pH, cell adhesion, cell attachment pattern, cell proliferation, cell signaling, cell survival, cell density, cell size, cell shape, cell polarity, $O_2$, $CO_2$, glucose, and combinations thereof; classifying the output as no response, weakly responsive, and responsive; and generating a report with the classification.

C. Cell Samples

Embodiments of the invention include systems, kits, and methods to determine the effectiveness of a therapeutic, monitor the effectiveness, or identify a dose of a therapeutic when administered to a subject's diseased cells.

Traditionally, disease has been classified by the tissue or organ that the disease affects. Due to better knowledge of the underlying mechanisms (e.g., genetic, autoimmune response, etc.), it is now understood that diseases which affect the same tissue/organ, or produce the same symptoms, may have different etiologies and may have heterogeneous gene expression profiles. In addition, it has been shown in many diseases that there are responders and non-responders to therapeutic agents. In embodiments, any disease type, for which responders and non-responders are identified, can be employed in the methods herein in order to predict or prognosticate whether a particular therapeutic drug combination of drugs will be effective for a particular individual, e.g. a determination whether the individual is a responder or a non-responder.

One example of a disease type that is known to be heterogeneous in nature and to have responders and many non-responders is cancer. Cancer is typically classified according to tissue type. However, a more accurate description of the heterogeneity of cancer is reflected in the different mutations of the different cancers. An even more accurate description of the heterogeneity of cancer is the actual functional, physiological result of the mutation in a particular patient's cells. For instance, prostate cancer has different types and different mutations that cause cancer of this organ. Outcomes and treatments can be different based on whether the mutation causing the cancer is a gain of function (e.g., proto-oncogene causing increase protein production) or loss of function mutation (e.g., tumor suppressor) and in which gene. Due to the heterogeneity of a particular cancer, it would be expected that there would a heterogeneous response to a particular therapeutic agent. Embodiments of this invention allow the testing of a particular subject's cancer cells to a therapeutic agent or a panel of therapeutic agents to determine the efficacy of a specific therapeutic agent or the most effective therapeutic agent for a particular subject's cancer to select a treatment for the subject.

Embodiments of the invention include disease cell samples of cancer cells from individual subjects. Such cancer cells can be derived from, but not limited to, Acute Lymphoblastic Leukemia (ALL), Acute Myeloid Leukemia (AML), Adrenocortical Carcinoma, Anal Cancer, Appendix Cancer, Astrocytomas, basal cell carcinoma, Extrahepatic Bile Duct Cancer, Bladder Cancer, Bone Cancer, Osteosarcoma, Malignant Fibrous Histiocytoma, Brain Stem Glioma, Central Nervous System Atypical Teratoid/Rhabdoid Tumor, Central Nervous System Embryonal Tumors, Central Nervous System Germ Cell Tumors, Craniopharyngioma, Ependymoblastoma, Ependymoma, Medulloblastoma, Medulloepithelioma, breast cancer, Pineal Parenchymal Tumors of Intermediate Differentiation, Supratentorial Primitive Neuroectodermal Tumors, Pineoblastoma, Bronchial Tumors, Carcinoid Tumor, Cervical Cancer, Chronic Lymphocytic Leukemia (CLL), Chronic Myelogenous Leukemia (CML), Chronic Myeloproliferative Disorders, Colon Cancer, Colorectal Cancer, Cutaneous T-Cell Lymphoma, Ductal Carcinoma In Situ (DCIS), Endometrial Cancer, Esophageal Cancer, Esthesioneuroblastoma, Ewing Sarcoma, Extragonadal Germ Cell Tumor, Intraocular Melanoma, Retinoblastoma, fibrous histiocytoma, Gallbladder Cancer, Gastric Cancer, Gastrointestinal Carcinoid Tumor, Gastrointestinal Stromal Tumors (GIST), Gestational Trophoblastic Tumor, Glioma, Hairy Cell Leukemia, Heart Cancer, Hepatocellular Cancer, Langerhans Cell Histiocytosis, Hodgkin Lymphoma, Hypopharyngeal Cancer, islet cell tumors, Kaposi sarcoma, renal cell cancer, Laryngeal Cancer, Lip Cancer, Liver Cancer, Lobular Carcinoma In Situ (LCIS), Lung Cancer, Merkel cell carcinoma, Melanoma, mesothelioma, mouth cancer, multiple myeloma, Nasal Cavity and Paranasal Sinus Cancer, Nasopharyngeal Cancer, Neuroblastoma, Non-Hodgkin Lymphoma, Non-Small Cell Lung Cancer, Oral Cavity Cancer, Oropharyngeal Cancer, Ovarian Cancer, Pancreatic Cancer, Papillomatosis, Paraganglioma, Parathyroid Cancer, Penile Cancer, Pharyngeal Cancer, Pheochromocytoma, Pineal Parenchymal, Pituitary Tumor, Pleuropulmonary Blastoma, Prostate Cancer, rectal cancer, rhabdomyosarcoma, salivary gland cancer, squamous cell carcinoma, small intestinal cancer, testicular cancer, throat cancer, thyroid cancer, ureter cancer, urethral cancer, uterine cancer, vaginal cancer, vulvar cancer, and Wilm's tumor.

Autoimmune diseases are characterized by increased inflammation due to immune system activation against self antigens. Current therapies target immune system cells such as B cells and inflammatory molecules such as anti TNFα. Therapies can be broadly characterized as immune modulating or immunosuppressant. Drugs may be targeted to particular molecules such as TNF alpha, Integrins, sphingosine receptors, and interleukins. Other drugs act as anti-inflammatory agents such as corticosteroids. In yet other cases, drugs are immunosuppressants such as mercaptopurines and cyclophosphamide. With respect to autoimmune conditions, peripheral blood cells may be examined for the response to a certain therapeutic. In other embodiments, tissue samples of the site of inflammation, for example, synovial tissue in rheumatoid arthritis or colon tissue for ulcerative colitis.

For example, some patients with rheumatoid arthritis are known to be non-responders to anti-TNFα antibodies. In an embodiment, peripheral blood cells can be obtained from a patient suspected as having RA and a decrease in cell signaling ability of the patient's TNF Receptor and associated MAPK pathway can be used to determine whether the patient is likely to be a responder or non-responder to an immunomodulating or immunosuppressant compound. Likewise other therapeutics such as those targeting to IL-6, Interferon alpha, Interferon gamma, and the like may be tested in the same way. In other embodiments, it is known that patients that have multiple sclerosis are nonresponders to interferon beta. Cell samples from subjects can be tested against a panel of drugs to see which if any of the drugs are effective for a particular subject by inducing a change in a cellular physiological parameter. Examples of advantageous outcomes would be a reduction in cellular inflammation parameters, as determined by the American College of Rheumatology (ACR) criteria or an increase in cell adhesion for strengthening the blood-brain barrier function.

In other embodiments, patients may have a disease caused by infection of cells by a microorganism, a foreign body, or a foreign agent. Blood cells or tissue samples infected with a microorganism may be evaluated for responsiveness to various antibiotics, antivirals, or other therapeutic candidates. For example, there are a number of different therapeutic agents for hepatitis C infection that reduce viral function, infected tissue samples can be contacted with one or more therapeutic agents and a change in a cellular physiological parameter is detected. Therapeutic agents are selected that provide a change in a cellular physiological parameter of the infected tissue, and/or a therapeutic agent that provides a change in a cellular physiological parameter at the lowest dose. Outcomes such as increase in cell survival or increase in cell growth would be considered advantageous. In other embodiments where the therapeutic is designed to effect the human cell directly such as by blocking viral entry via a specific receptor type or perturbation of a cellular pathway, the patient cell could be tested for receptor binding or pathway perturbation by said therapeutic as described in other embodiments herein.

In embodiments, the cell samples can be obtained before therapy is initiated, during therapy, after therapy, during remission, and upon relapse. The methods as described herein are useful to predict therapeutic efficacy prior to treatment, during treatment, when a patient develops resistance, and upon relapse. The methods of the disclosure are also useful as to predict responders or non-responders to a therapeutic agent or combination of agents.

In certain embodiments, the cells are not contacted or treated with any kind of fixative, or embedded in paraffin or other material, or any detectable label. In other embodiments, it is preferred that the cells remain whole, viable and/or label free. In some other embodiments, a cell sample is provided for both the diseased tissue and healthy tissue. In some embodiments, the cell sample is provided in both viable and fixed form. A cell sample provided in fixed form can serve as a control for comparison to the viable cells that are analyzed in accord with the methods as described herein particularly for improved identification and correlation of additional biomarkers.

In other embodiments of the invention, cells from an individual subject are used to determine therapeutic effectiveness. Cells can be collected and isolated by well-known methods (i.e., swab, biopsy, etc.). Both diseased and non-diseased cells can be used. Non-diseased cells can be used as a negative control, a baseline measure, a comparison for measures over time, etc. In embodiments, a control sample of tissue cells from the same subject may also be obtained. A control sample may be taken from another healthy tissue in the subject or from healthy tissue from the same organ as the diseased tissue sample. Diseased cells are cells extracted from a tissue with active disease. In an embodiment, diseased cells can be tumor cells, such as breast cancer cells. Cancerous cells do not necessarily have to be extracted from a tumor. For instance, leukemic cells can be collected from the blood of a patient with leukemia. Cells can be collected from different tissue sites such as the sites of metastasis, circulating tumor cells, primary tumor sites, and recurrent tumor sites, and cellular responsiveness compared to one another. In another embodiment, diseased cells can be extracted from a site of autoimmune disease, such as rheumatoid arthritis. In certain embodiments, the number of cells in each tissue sample is preferably at least about 5000 cells. In other embodiments, the cell number in the tissue sample may range from about 5000 to 1 million cells or greater. Cell samples include isolation from, but are not limited to, blood, blood serum, blood plasma, urine, semen, seminal fluid, seminal plasma, prostatic fluid, pre-ejaculatory fluid (Cowper's fluid), excreta, tears, saliva, sweat, biopsy, ascites, cerebrospinal fluid, lymph, marrow, or hair. In some other embodiments, the cell samples can contain or be derived from patient serum, fractions thereof, organoids, fibroblasts, stromal cells, mesenchymal cells, epithelial cells, white blood cells, red blood cells, B cells, T cells, immune cells, stem cells, or combinations thereof.

In one embodiment, the extraction of cells from a subject is at the same location as the CReMS (e.g., laboratory, hospital). As such, the cells can be suspended or preserved in a well-known transfer medium to bridge the time from subject to biosensor. In another embodiment, the extraction of cells from a subject is at a different location from the CReMS. Once obtained the cell samples are maintained in a medium that retains the cell viability. Depending on the length of time for transportation to the site of analysis, different media may employed. In embodiments, when transportation of the tissue sample may require up to 10 hours, the media has an osmolality of less than 400 mosm/L and comprises Na+, K+, Mg+, Cl—, Ca+2, glucose, glutamine, histidine, mannitol, and tryptophan, penicillin, streptomycin, contains essential amino acids and may additionally contain non-essential amino acids, vitamins, other organic compounds, trace minerals and inorganic salts, serum, cell extracts, or growth factors, insulin, transferrin, sodium selenite, hydrocortisone, ethanolamine, phosphophorylethanoloamine, tridothyronine, sodium pyruvate, L-glutamine, to support the proliferation and plating efficiency of human primary cells. Examples of such a media include Celsior media, Roswell Park Memorial Institute medium (RPMI), Hanks Buffered Saline, and McCoy's 5A, Eagle's Essential Minimal Media (EMEM), Dulbecco's modified Eagle's medium (DMEM), Leibovitz L-15, or modifications thereof for the practice of primary cell care. In embodiments, the media and containers are endotoxin free, nonpyrogenic and DNase- and RNase-free.

In other embodiments of the methods described herein, diseased cells obtained from a subject are handled under conditions where the concentration of oxygen in the working environment is less than 20%, less than 15%, less than 10%, less than 3%, less than 2% or less than 1.8%. In such embodiments, it is possible to create culture conditions for the cells that are similar to those found in the tissue from which they were derived in the patient, and thereby present the cells in a state most likely to mirror those in the patient. In other embodiments, it is possible to create conditions that purposefully perturb the cells to create functional activation, for the purpose of testing cellular physiologic responses and assessing dysfunction.

In other embodiments, the diseased cells obtained from a tissue specimen of an individual subject are extracted using steps that include mincing and enzyme digestion of a tissue specimen, separation of extracted cells by cell type, and/or culturing of the extracted cells. The culturing reagent can include various supplements, for example, patient serum or patient derived factors.

A further aspect includes a method of extracting organoids from a tissue specimen, which can subsequently be used to determine the efficacy of a therapeutic agent in an individual subject. Such a method comprises mincing and enzyme digestion steps. A further aspect includes a method of culturing organoids from a tissue specimen, which can subsequently used to determine the efficacy of a therapeutic agent in an individual subject. Such a method comprises mincing, enzyme digestion, separation by cell type, and culturing steps. A further aspect may include the specific recombination of the so separated cells to perform the methods described herein.

D. Cellular Response Measurement System ("CReMS")

Systems and methods of the invention utilize a cellular response measurement system (CReMS). CReMS refers to a device that can quantitatively determine a change in a physiological parameter in a cell, in and between cells, and between cells and the instrumentation device. A change in a physiological parameter is measured by determining change in an analyte (including non-limiting examples such as extracellular matrix, cell signaling molecule, or cell proliferation, tissue, cells, metabolites, catabolites, biomolecules, ions, oxygen, carbon dioxide, carbohydrates, proteins etc.). In embodiments, the biosensor is measuring a change in the physiological parameter in isolated whole label free viable cells. In embodiments, a biosensor is selected that can measure an expected change due to the type of therapeutic and/or activator agent.

An example of a CReMS is a biosensor. Examples of biosensors are electrochemical biosensors, electrical biosensors, optical biosensors, mass sensitive biosensors, thermal biosensors, and ISFET biosensors. Electrochemical biosensors measure potentiometric, amperometric and/or voltammetric properties. Electrical biosensors measure surface conductivity, impedance, resistance or electrolyte conductivity. Optical biosensors measure fluorescence, absorption, transmittance, density, refractive index, and reflection. Mass sensitive biosensors measure resonance frequency of piezocrystals. Thermal biosensors measure heat of reaction and adsorption. ISFET biosensors measure ions, elements, and simple molecules like oxygen, carbon dioxide, glucose, and other metabolites of interest in the life sciences. In embodiments, the biosensor is selected from the group consisting of an impedance device, a photonic crystal device, an optical waveguide device, a surface plasmon resonance device, quartz crystal resonators/microbalances, and a microcantilever device. In embodiments, an optical biosensor can comprise an optical transducer for converting a molecular recognition or molecular stimulation event in a living cell, a pathogen, or combinations thereof. In a specific embodiment, the device is an impedance device.

In an example of a biosensor used to measure protein or other in vitro biomolecular interactions, the capture of a specific protein mass is translated into meaningful biochemical and biophysical values. Applying a simple calculation with the captured mass involving the molecular weight of the specific protein captured, the number of moles are evaluated, leading to equilibrium binding constants and other interaction descriptive values known to those experienced in the art. In an example of a biosensor used for cell assays, specific adhesion molecules on the cell surface modulate their attachment and morphology close to the surface of the sensor and other nearby cells upon application of external chemical or other stimulus via specific cellular pathways.

The biosensor can detect these modulations that can be selected in such a way as to be unique to the stimulus and pathway within the cell employed to respond to stimuli. When designed properly, the biosensor result for said cell assay can be exquisitely quantitative in molecular and functional terms. Said biosensor result can be a temporal pattern of response for further uniqueness. Biomolecular activators or perturbants known to turn on and turn off specific pathways within the cell can be used as controls for determining the specificity of the CReMS biosensor signal. Methods for curve deconvolution of the temporal response of the biosensor result (e.g. non-linear Euclidean comparison with control responses) can be applied to further more finely detail specific cellular responses. Use of titrating external stimuli in a cellular biosensor assay can also provide further biochemical and biophysical parameter description.

One example of a label-free sensor is a high frequency quartz resonator or quartz crystal microbalance (QCM) or resonating cantilever. The resonator includes a quartz crystal with a patterned metal electrode upon its surface. The quartz material has well-characterized resonance properties when a voltage is applied. By applying an alternating voltage to the electrodes at a particular frequency, the crystal will oscillate at a characteristic frequency. The oscillation frequency is modulated in quantitative ways when mass is captured on the sensor surface; additional mass results in lower resonator frequency. Therefore, by measuring small changes in the resonant frequency of the quartz oscillator, very small changes in deposited mass can be measured without attaching a label to the biomolecule or cell under study.

Ion Selective Field Effect Transistor (ISFET) devices are miniaturized, nanoscale, devices that are capable of measuring selected ions, elements, and simple molecules like oxygen, carbon dioxide, glucose, and other metabolites of interest in the life sciences. They have been extensively described at the electromechanical operational level as well as at the bioapplication level. To date they have not been described for the use with a specific patient's cells to discern response or resistance or temporal patterns thereof to proposed therapeutic intervention in disease processes.

Optical biosensors are designed to produce a measurable change in some characteristic of light that is coupled to the sensor surface. The advantage of this approach is that a direct physical connection between the excitation source (the source of illumination of the sensor), the detection transducer (a device that gathers reflected or transmitted light), and the transducer surface itself is not required. In other words, there is no need for electrical connections to an optical biosensor, simplifying methods for interfacing the sensor with fluid required for stabilizing and studying most biological systems. Rather than detecting mass directly, all optical biosensors rely on the dielectric permittivity of detected substances to produce a measurable signal. The changes in dielectric permittivity are related to the difference in ratio of the speed of light in free space to that in the medium. This change essentially represents the refractive index of the medium. The refractive index is formally defined as the square root of the dielectric constant of a medium (see Maxwell's equation for more explicit treatment of this relationship). An optical biosensor relies on the fact that all biological material, such as proteins, cells, and DNA, have a dielectric constant that is higher than that of free space. Therefore, these materials all possess the intrinsic ability to slow down the speed of light that passes through them. The optical biosensors are designed to translate changes in the propagation speed of light through a medium that contains biological material into a quantifiable signal that is proportional to the amount of biological material that is captured on the sensor surface.

Different types of optical biosensors include but are not limited to ellipsometers, surface plasmon resonant (SPR) devices, imaging SPR devices, grating coupled imaging SPR devices, holographic biosensors, interference biosensors, Reflectometric Interference Spectroscopy (RIFS), Colorimetric Interference Biosensors, Difference Interferometers, Hartman Interferometers, Dual Polarization Interferometers (DPI), Waveguide sensor chips, Integrated Input Grating Coupler devices, Chirped Waveguide Grating devices, Photonic crystal devices, Guided Mode Resonant Filter devices based upon Wood's Anomalies, Trianglular Silver Particle Arrays. And further include devices that measure a variety of wavelengths of the electromagnetic spectrum including but not limited to visible, ultraviolet, near infrared, and infrared. The modes of operation include but are not limited to scattering, inelastic scattering, reflection, absorbance, Raman, transmittance, transverse electric wave, and transverse magnetic wave.

The surface plasmon resonance device is an optical biosensor that measures binding events of biomolecules at a metal surface by detecting changes in the local refractive index. In general, a high-throughput SPR instrument consists of an auto-sampling robot, a high resolution CCD (charge-coupled device) camera, and gold or silver-coated glass slide chips each with more than 4 array cells embedded in a plastic support platform. SPR technology exploits surface plasmons (special electromagnetic waves) that can be excited at certain metal interfaces, most notably silver and gold. When incident light is coupled with the metal interface at angles greater than the critical angle, the reflected light exhibits a sharp attenuation (SPR minimum) in reflectivity owing to the resonant transfer of energy from the incident light to a surface plasmon. Binding of biomolecules at the surface changes the local refractive index and results in a shift of the SPR minimum. By monitoring changes in the SPR signal, it is possible to measure binding activities at the surface in real time.

Since SPR measurements are based on refractive index changes, detection of an analyte is label free and direct. The analyte does not require any special characteristics or labels (radioactive or fluorescent) and can be detected directly, without the need for multistep detection protocols. Measurements can be performed in real time, allowing collection of kinetic data and thermodynamic data. Lastly, SPR is capable of detecting a multitude of analytes over a wide range of molecular weights and binding affinities. Thus, SPR technology is quite useful as a cellular response measurement system.

A CReMS for the measurement of complex impedance changes (delta Z, or dZ) of live patient cells is described in this embodiment where impedance (Z) is related to the ratio of voltage to current as described by Ohm's law (Z=V/I). For example a constant voltage is applied to electrodes to which patient cells are attached, producing a current that at differential frequencies flows around, between cells and through cells. This CReMS is sensitive to the local ionic environment at the electrode interface with the cells and detects these changes as a function of voltage and current fluctuations. Physiologic changes of the cells as a result of normal function or perturbation thereof result in quantifiable changes to the flow of current around the electrodes and influence the magnitude and characteristics of the signal measured in such a CReMS.

In certain embodiments, the biosensor detects a change in global phenotype with event specificity. A global phenotype comprises one or more cellular response parameters selected from the group consisting of pH, cell adhesion, cell attachment pattern, cell proliferation, cell signaling, cell survival, cell density, cell size, cell shape, cell polarity, $O_2$, $CO_2$, glucose, cell cycle, anabolism, catabolism, small molecule synthesis and generation, turnover, and respiration, ATP, calcium, magnesium, and other charged ions, proteins, specific pathway member molecules, DNA and or RNA in various cellular compartments, genomics, and proteomics, post-translational modifications and mechanisms, levels of secondary messenger, cAMP, mRNA, RNAi, microRNAs and other RNA with physiologic function, and combinations thereof. With respect to event specificity, a cellular parameter is selected that reflects a change in a cell sample that is an expected change for that type of therapeutic and/or activator agent. For example, if a therapeutic agent is known to target a cytoskeletal element, a cell contacted with such an agent would be expected to show a change in cell adhesion in the presence of the agent.

In other embodiments, the change in attachment pattern is a change in cell adhesion. In some cases, the change in cell adhesion is indicated by a change in a refractive index or a change in impedance. In yet other embodiments, the change in attachment pattern is a change in basal morphology, a change in cell density, or a change in cell size or cell shape. In a specific embodiment, the change in basal morphology is a change in cell polarity. In embodiments, a decrease in cell signaling indicates a change in cytoskeletal organization.

In other embodiments, the methods of the disclosure provide for analysis of cell samples that are label free and that can be measured in real time. In one embodiment, the cell sample analyzed is a label free, viable, and not subject to any treatments to fix the cells. In another embodiment, the therapeutic and/or activator agents used in the methods and kits of the disclosure are also label free. To date label free methods have not been applied to determining therapeutic efficacy in effective ways.

Label free assays can reduce the time and cost of screening campaigns by reducing the time and misleading complications of label assays. Assays that can identify and quantify gene expression, gene mutation, and protein function are performed in formats that enable large-scale parallelism. Tens-of-thousands to millions of protein-protein or DNA-DNA interactions may be performed simultaneously more economically with label-free assays.

In contrast to the large variety of labeled methods, there are relatively few methods that allow detection of molecular interaction and even fewer still for cellular function without labels. Label-free detection removes experimental uncertainty created by the effect of the label on molecular folding of therapeutic and activator agents, blocking of active sites on cells, or the inability to find an appropriate label that functions equivalently for all molecules in an experiment that can be placed effectively within a cell. Label-free detection methods greatly simplify the time and effort required for assay development, while removing experimental artifacts from quenching, shelf life, and background interference.

Although labels are a mainstay of biochemical and cell-based assays, there are disadvantages to their use. Labels comprise the majority of all assay methods and have to overcome several problems, especially in the context of the study of complex activities in human cells. Use of radioactive labels create large quantities of contaminated materials and must be used in specialized facilities with regulatory methods to prevent harm (at the cellular level) to those that use them. The excitation/emission efficiency of fluorophores is degraded by time and exposure to light, reducing the ability of the label to be accurate and precise, and requiring that assays be read once only in an end point manner so that temporal information cannot be obtained. All label-based assays require a significant amount of time to develop a process for attaching the label in a homogenous and uniform manner, determining that the label will be linearly quantitative, and will not interfere or affect the interaction or process being measured. The uniform application of labels in complex mixtures is complicated by the presence of all the molecules that are needed for the process to proceed naturally. Addition of the label only allows for visualization of that molecule function indirectly, not the entire system function directly (i.e. some extended assumptions may be necessary). Cellular activities are even more difficult to measure accurately with labels. Besides figuring out how the label will get onto the right molecule, the right way, in the right location with respect to the cell, it is presently impossible to be certain that the label is not disturbing the normal cellular processes, thereby making the extrapolation to in vivo conditions tenuous.

Label-free detection generally involves the use of a transducer that is capable of directly measuring some physical property of a biological compound or bioentity such as a DNA molecule, peptide, protein, or cell. All biochemical molecules and cells have finite physical values for volume, mass, viscoelasticity, dielectric permittivity, heat capacity and conductivity that can be used to indicate their presence or absence, increase or decrease, and modification using a type of sensor. Additionally living systems utilize molecules to provide energy and carry out their life processes, such as $O_2/CO_2$ consumption/generation, glucose production/consumption, ATP production/consumption that cause measurable changes such as pH in their environ over finite periods of time. The sensor functions as a transducer that can convert one of these physical properties into a quantifiable signal such as a current or voltage that can be measured.

In some cases, in order to use a transducer as a biosensor, the surface of the transducer must have the ability to selectively capture specific material such as a protein or specific cell type, while not allowing undesired material to attach. Selective detection capability is provided by building of a specific coating layer of chemical molecules on the surface of the transducer. The material that is attached to the sensor surface is referred to as the sensor coating while the detected material is called the analyte. Thus, in some cases, a biosensor is the combination of a transducer that can generate a measurable signal from material that attaches to the transducer, and a specific recognition surface coating containing a receptor ligand that can bind a targeted analyte from a test sample.

In certain embodiments, a coating is selected for a biosensor that is associated with a particular cellular component or pathway. For example, in those cases, where the cellular physiological parameter is change in cell adhesion, a coating is selected that provides for adhesion of the cells in the cell sample to the biosensor surface. In embodiments, the coating that enhances adhesion of the cells to the biosensor includes extracellular matrix, fibronectin, integrins and the like. In other embodiments, a coating is selected that binds to a particular cell type based on a cell surface marker. In embodiments, such cell surface markers include, CD20, CD30, EGFR, EGFR-TK, PI3K, MEK1, MEK2, HER2 receptor, Her3 receptor, Her4 receptor, VEGFR, and other cell surface cancer biomarkers.

In other embodiments, the biosensor is coated with a biomolecular coating. CReMS surfaces contacting cells may contain a biomolecular coating prior to addition of cells, during addition of cells, or after addition of cells. The coating material may be synthetic, natural, animal derived, mammalian, or created by cells placed on the sensor. For example, a biomolecular coating can comprise an extracellular matrix component known to engage integrins, adherins, cadherins and other cellular adhesion molecules and cell surface proteins (e.g., fibronectin, laminin, vitronectin, collagens, IntercellularCAMs, VascularCAMs, MAdCAMs), or a derivative thereof, or can comprise a biochemical such as polylysine or polyornithine, which are polymeric molecules based on the naturally occurring biochemicals lysine and ornithine, polymeric molecules based on naturally occurring biochemicals such as amino acids can use isomers or enantiomers of the naturally-occurring biochemical, antibodies, fragments or peptide derivatives of antibodies, complement determining region (CDR), designed to attach specific cell surface proteins to the biosensor.

Methods for attaching viable cells to a microplate may include, for example, coating the sensor microplate surface with a reactive molecule having one end designed to interact with the surface of the biosensor, and another end that designed to react with functional groups on a peptide. For example, when using a gold-coated biosensor, the reactive molecule could include a sulfur atom or other chemical moiety designed to chemically interact with the biosensor surface. The other end of the molecule can specifically react with, for example, the amide or carboxy groups on a peptide.

In another example, the biosensor surface can be coated with molecules that adhere through van der waals forces, hydrogen bonding, electrostatic attraction, hydrophobic interaction, or any combination of these such as one practiced in the art might use to apply proteins. An extracellular matrix (ECM) molecule can also be added to the first surface molecular coating. Exemplary ECM molecules that can be used in this capacity include, but are not limited to, fibronectin, collagen, and vimentin. Humphries 2006 Integrin Ligands at a Glance. Journal of Cell Science 119 (19) p 3901-03. describes adhesion molecules useful in this invention. Additional ECM molecules that can be used to contact specific cell adhesion molecules include those described in Table 1 of Takada et al., Genome Biology 8:215 (2007). This example is for integrins involved in cell-ECM and cell-cell adhesion. Many other adhesion molecules have been described with properties related to physiologic control and response. (see below).

| Ligand-binding specificities of human integrins | |
|---|---|
| Integrins | ECM and cell-cell Ligands |
| α1β1 | Laminin, collagen |
| α2β1 | Laminin, collagen, thrombospondin, E-cadherin, tenascin |
| α3β1 | Laminin, thrombospondin, uPAR |
| α4β1 | Thrombospondin, MAdCAM-1, VCAM-1, fibronectin, osteopontin, ADAM, ICAM-4 |
| α5β1 | Fibronectin, osteopontin, fibrillin, thrombospondin, ADAM, COMP, L1 |
| α6β1 | Laminin, thrombospondin, ADAM, Cyr61 |
| α7β1 | Laminin |
| α8β1 | Tenascin, fibronectin, osteopontin, vitronectin, LAP-TGF-β, nephronectin, |
| α9β1 | Tenascin, VCAM-1, osteopontin, uPAR, plasmin, angiostatin, ADAM [25], VEGF-C, VEGF-D[26] |
| α10β1 | Laminin, collagen |
| α11β1 | Collagen |
| αVβ1 | LAP-TGF-β, fibronectin, osteopontin, L1 |
| αLβ2 | ICAM, ICAM-4 |
| αMβ2 | ICAM, iC3b, factor X, fibrinogen, ICAM-4, heparin |
| αXβ2 | ICAM, iC3b, fibrinogen, ICAM-4, heparin, collagen [27] |
| αDβ2 | ICAM, VCAM-1, fibrinogen, fibronectin, vitronectin, Cyr61, plasminogen |
| αIIbβ3 | Fibrinogen, thrombospondin, , fibronectin, vitronectin, vWF, Cyr61, ICAM-4, L1, CD40 ligand [28] |
| αVβ3 | Fibrinogen, vitronectin, vWF, thrombospondin, fibrillin, tenascin, PECAM-1, fibronectin, osteopontin, BSP, MFG-E8, ADAM-15, COMP, Cyr61, ICAM-4, MMP, FGF-2 [29], uPA [30], uPAR [31], L1, angiostatin [32], plasmin [33], cardiotoxin [34], LAP-TGF-β, Del-1 |
| α6β4 | Laminin |
| αVβ5 | Osteopontin, BSP, vitronectin, CCN3 [35], LAP-TGF-β |
| αVβ6 | LAP-TGF-β, fibronectin, osteopontin, ADAM |
| α4β7 | MAdCAM-1, VCAM-1, fibronectin, osteopontin |
| αEβ7 | E-cadherin |
| αVβ8 | LAP-TGF-β |

Additional coatings may include antibodies or other proteins known to have affinity for patient cell surface proteins so as to bring the patient cells into close proximity to the biosensor for the purpose of performing the methods described herein. It may also be beneficial to confirm that the patient cells are attached in the desired manner to the microplate. Specific biosensor coatings can additionally be used to enhance, improve, clarify, segregate, or detect specific cell signals from specific patient cell types and cell signaling responses to perturbation and therapeutics by linking the sensor coating to specific cellular pathways (see, e.g., Hynes, *Integrins*, Cell, 110:673-687 (2002)). A biosensor comprises an area to seed cells. For example, a biosensor can comprise a microtiter plate containing wells to seed cells. One or more cell samples can be seeded on a biosensor by physical adsorption to a surface in a distinct location. A biosensor can comprise 1, 10, 24, 48, 96, 384, or more distinct locations. A cell sample can comprise about 100 to about 100,000 individual cells or any cell number in between. An optimal cell sample depends on the size and nature of a distinct location on a biosensor. A cell sample can comprise about 5000 cells or less; about 10,000 cells or less; about 15,000 cells or less; about 20,000 cells or less; about 25,000 cells or less; or about 50,000 cells or less. A cell sample can comprise about 1000 to about 2500 cells; about 1000 to about 5000 cells; 5000 to about 10,000 cells; about 5000 to about 15,000 cells; about 5000 to about 25,000 cells; about 1000 to about 10,000 cells; about 1000 to about 50,000 cells; and about 5000 to about 50,000 cells.

In certain embodiments, a change in a cellular response or physiological parameter is measured over a defined period of time. In other embodiments, the defined period of time is the amount of time that it takes for the control cells to reach a steady state in which a change in the output of the physiological parameter varies by 20% or less. In other embodiments, the change is observed in cells in 1 hour or less. In other embodiments, the change is observed in cells for at least 1 min. to about 60 min. and every minute in between. In other embodiments, the change in cell response is measured from about 10 minutes to about one week or 200 hours. In other embodiments, when a therapeutic agent is targeted to a cellular pathway, the cellular response is measured from about 10 minutes to about 5 hours, about 10 minutes to about 4 hours, about 10 minutes to about 3 hours, about 10 minutes to about 2 hours, about 10 minutes to about 1 hour, or about 10 minutes to about 30 minutes or any time point in between. In other embodiments, when a therapeutic agent affects cell proliferation or cell killing or cellular resistance, the cellular response is measured from about 1 hour to about 200 hours. In yet other embodiments, a combination of responses (otherwise described as a full temporal pattern) between 1 minute and 200 hours is used to determine therapeutic effect of a compound on cells and the cells ability to develop resistance. This timeframe encompasses the important process of short-term pathway signaling, dynamic reprogramming and longer term cellular responses important in assessing a probable response and maintenance thereof in a patient.

Once cells of a particular subject have been seeded on a biosensor, baseline measurements can be determined. Baseline measurements can be taken on the same cell sample, or a control cell sample. The control sample can comprise healthy cells or diseased cells from the same patient and/or same tissue. A control sample can comprise disease cells known to respond to the agent. In other embodiments, the control sample comprises disease cells known not to respond to the agent. The control sample may include application of an activator agent to healthy or diseased cells of a particular patient, designed to elicit a standardized response relating to cell health, cell metabolism, or cell pathway activity.

The control would be determined for each disease and/or drug type. In one embodiment, this involves a comparison against a healthy cell control from the same patient. For example, with cell killing drugs, the method will show benefit of killing disease cells over healthy cells to achieve a significant therapeutic index. Other embodiments include the use of pathway tools to determine pathway function and control by the drug. For targeted therapeutics, the tools can be perturbing agents (e.g., activator agents), bioreagents or small molecules which are used as controls to perturb a pathway and determine a targeted drug's ability to disrupt the perturbation. In yet other embodiments, the physiologic effect of a drug on a cell is measured without exogenous perturbation by an activator agent noting, for example, the temporal pattern or rate of oxygen consumption, the rate or temporal pattern of acidification, ion flux, or metabolite turnover.

In a particular embodiment, the biosensor signal is measured over a continuous time course. There are distinctive patterns on the time vs. biosensor signal plot that are indicative of a patient cell response to drug treatment. Evaluation of these patterns is useful to identify the presence of an efficacious event. A time course or constantly changing measurement of live and fully functional cells is more beneficial than the current practice used in typical whole cell assays that only represent a point in time. The methods described herein measure dynamic systems as they would occur in a patient and represent the most accurate means of determining patient response. In the case of pathway responses, recording of a complete time course or temporal pattern is superior in ability to support more complex analysis and obviates selecting the optimum time point for a single measurement.

Comparison against controls could occur at a temporal maxima, minima, or as differences between maximal signal-minimal signal, or by comparing integrated areas under a curve (AUC) for a time course plot or other non-linear comparisons of the test well against positive or negative control wells. Additional analyses supported only by measuring with a biosensor are time to reach maxima/minima, and other derivatives of the temporal time course. In the case of longer term responses, the time of comparison may be of a specific time point after a few days or a week of treatment or multiple applications of drug. The longer time course may also compare changes in slope or compare second derivatives of the time versus biosensor signal plot at the beginning, middle or end of a week of drug treatment. Significant changes compared to control may include absolute drop in biosensor signal related to curtailment of cellular metabolism. Alternatively, the drop may be followed by an increase that could indicate development of resistance to the drug during the assay. Additionally, non-linear Euclidean analyses could be used to produce a measure of total differences between controls and patient samples over a complete time-course. This too would be significant with respect to predicting the outcome for a patient.

In certain embodiments, the output of a biosensor over a defined period of time is represented as a cell index. The cell index is the change in impedance from a test starting point. Cell Index is defined as a measurement of impedance and can be applied in one instance of the present invention by measuring at a fixed electrical frequency of, for example, 10 kHz and fixed voltage.

And calculated by the equation Cell Index$_i$=($R_{tn}$−$R_{t0}$)/F

Where:
i=1, 2, or 3 time point
F=15 ohm in one example when the instrument is operated at 10 kHz frequency
$R_{t0}$ is the background resistance measured at time point T0.
$R_{tn}$ is the resistance measured at a time point Tn following cell addition, cell physiologic change, or cell perturbation.

Cell index is a dimensionless parameter derived as a relative change in measured electrical impedance to represent cell status. When cells are not present or are not well-adhered on the electrodes, the CI is zero. Under the same physiological conditions, when more cells are attached on the electrodes, the CI values are larger. CI is therefore a quantitative measure of cell number present in a well. Additionally, change in a cell physiological status, including cell morphology, changes in basal, stable, or quiescent condition, cell adhesion, or cell viability will lead to a changes in CI.

The cell index is a quantitative measure of the presence, density, attachment or changes thereof based upon a starting point or baseline impedance measurement. The baseline starting point impedance is a physical observable characteristic and an indication of the health, viability, and physiologic status of a cell prior to any treatment with drug or other perturbant. The baseline starting point can be used as a qualitative control for the CELx test. Addition of drug or perturbant causes the impedance to change in temporal patterns reflective of the specificity of the cellular physiologic change experienced by the cell. Changes in a cell physiological status, for example cell morphology, cell number, cell density, cell adhesion, or cell viability will lead to a changes in the cell index.

Physiologic response parameters can additionally include cell cycle analysis and can be measured using any number of chemical biosensors such as fluorescent dyes conjugated or unconjugated or other colorimetric changes in patient cells associated with functional and dysfunctional pathways. For example changes in cell cycle for a population of cells using an unconjugated dye can be quantified with propidium iodide or similar dyes known to intercalate into DNA and correlate with cell cycling through G0, G1, S, G2, Gm phases of growth and replication by assessing changes in the amount of DNA. With one dye type, propidium iodide, the fluorescence of cells in the G2/M phase will be twice as high as that of cells in the G0/G1 phase. Propidium iodide can also intercalate into RNA and often ribonucleases are used to differentiate fluorescence signal from DNA compared to RNA. Examples also include dyes specific for particular proteins linked to cell cycle check points and provide additional cell cycle status measurement. Common instruments useful for performing these measurements but not limited to those listed here are fluorescence microscopy, confocal laser scanning microscopy, flow cytometry, fluorometry, fluorescence polarization, homogenous time resolved fluorescence, and fluorescence activated cell sorting (FACS).

Unconjugated dyes can be utilized with the present invention as a chemical biosensor of physiologic status of a cell or pathway while measuring metabolic parameters such as anabolism, catabolism, small molecule synthesis and generation, turnover, and respiration. A well-known cell physiologic response, named the Warburg Effect, describes the shift from oxidative phosphorylation to lactate production for energy generation in tumor and other diseased cells, and key signaling pathways, oncogenes and tumor suppressors (for example but not limited to Akt, mTor, c-myc, p53) can be measured by any of the chemical biosensor methods described here or by opto-electronic biosensors. Cellular oxygen consumption or respiration and glycolysis in cellular responses produces protons and causes rapid, easily measurable changes to the concentrations of dissolved oxygen and free protons or acidity.

An additional but not limiting example of a physiologic response parameter utilizing a chemical biosensor is the amount of ATP being utilized by cells in culture based on quantitation of the ATP present (Ex. CellTiterGlo and similar luciferase driven assays), an indicator of metabolically active and inactive cellular function.

Calcium, magnesium, and other charged ions that are important for biomolecular folding and function are in flux due to physiologic response. These too can be measured by chemical biosensors such as Cal-520, Oregon Green BAPTA-1, fura-2, indo-1, fluo-3, fluo-4, Calcium Green-1, and other EGTA or EDTA-like chemistries for specific ion complexation and measurement. These physiologic response parameters can be measured using many types of unconjugated reactive or binding dyes or other electronic or spectroscopic means. Many of these methods can be arranged so as to be non-destructive to the cells allowing the physiologic function of the same cell population to be continuously measured repeatedly over time.

Conjugated dyes such as those attached to natural cell protein binding ligands or attached to immunoparticles (antibodies or fragments of antibodies or high specificity high affinity synthetic molecules such as aptamers), or nucleic acid polymer hybridization probes can be used to measure physiologic response parameters related to proteins, specific pathway member molecules, DNA and or RNA in various cellular compartments, genomics, and proteomics, and are able to measure specific post-translational modifications and mechanisms. The post-translational modification and epigenetic means of cellular control can involve regulation by a multitude of enzymes performing pathway functions that include but are not limited to ribozymes, kinases, phosphatases, ubiquitinases, deubiquitinases, methylases, demethylases, and proteases. Examples of these molecules used for staining formalin fixed paraffin mounted samples of dead cells can be found in the DAKO Immunohistochemical Staining Methods Education Guide—Sixth Edition or at Cell Signaling Technology tutorials and application guides http://www.cellsignal.comicommon/content/content.jsp?id=tutorials-and-application-guides. These two examples may be even more useful with the present invention for measuring live cell response. Common instruments useful for performing this measurement but not limited to these methods are fluorescence microscopy, confocal laser scanning microscopy, flow cytometry, fluorometry, homogenous time resolved fluorescence, fluorescence polarization, and fluorescence activated cell sorting (FACS).

Combinations of conjugated and non-conjugated dyes can also be employed by the present invention to measure physiologic response of cells. Following activation, one type of receptor responsible for controlling physiologic response are GPCRs. They transmit information and control cells via two signaling pathways: changes in the level of secondary messenger cAMP, or changes in the level of intracellular Ca2+, which is liberated by secondary messenger inositol (1,4,5) triphosphate (IP3). cAMP detection for example can be based on a competitive immunoassay using cryptate-labeled anti-cAMP antibody (or other immunocapture molecule) and d2-labeled cAMP that competes with cellular cAMP for the GPCR reaction and subsequent antibody binding. The specific signal (i.e. energy transfer) is inversely proportional to the concentration of cAMP in the standard or sample.

Measurement of physiologic response by quantifying mRNA, RNAi, microRNAs and other RNA with physiologic function can be a very sensitive method employed with the practice of the present invention for determining perturbation of a cellular change at the transcription level. RNA can be quantified for example but not limited to these listed here by using rtPCR, qPCR, selective sequence probing, selective sequence capture, and sequence hybridization methods that all employ chemical sensors.

Immuno-capture and hybridization methods include those using bead based methods such as Luminex or fiber optic tip technologies such as Illumina or protein, DNA, RNA, or other hybridization microarray technologies where the specific capture reagent is immobilized onto a solid surface that is used to fish out, isolate, and accurately measure the physiologic response molecule(s) from the cells. These methods offer the benefit of measuring a multitude of response parameters in a single experiment.

A change in a cellular response or physiological parameter is determined by comparison to a baseline measurement. The change in cellular parameter or physiological response depends on the type of CReMS. For example, if the change in cellular response is determined optically, physically observable changes could be measured for example as a function of optical density at spectral wavelengths for chemical absorbance or transmittance, changes in a surface plasmon measurement device, or changes detected by photonic crystal devices. If the change in cellular parameter or physiological response is determined electrically, physically observable changes could be measured for example using milli or micro impedance changes of cells adhered to electrodes. Changes in pH, glucose, carbon dioxide, or ions, could be measured electronically using ion selective field effect transistors (ISFET).

In other embodiments, a rate of change is determined by a method measuring a CReMS response for a period of time required to determine a difference in cellular physiologic response to a therapeutic. The rate of change is described by various interpretation of the time course data and can be expressed as a rate or further derivative function of the rate including acceleration of the rate.

Tests that measure a physiological condition of a patient can derive one or more cutoff values above which and below which the patient is predicted to experience different clinical outcomes. In embodiments, one or more cutoff values for determining a change in cellular response is determined by a method comprising: determining a standard deviation, a signal to noise ratio, a standard error, analysis of variance, or other statistical test values known by those practiced in the art for determining appropriate confidence intervals for statistical significance of a set of samples from known responding cell samples and from a set of samples from known nonresponding patients; and determining the difference between the two and setting the cutoff value between the confidence intervals for both groups. Preferred embodiments include 80-90% confidence intervals, more preferred embodiments include >90% confidence intervals and most preferred embodiments include >95% or >99% confidence intervals. In embodiments, a cutoff value is validated by determining the status of blinded known samples as responders or nonresponders using a cutoff value and unblinding the sample and determining the accuracy of predicting the status of the sample. In the case of a single cutoff value, values that fall below the cutoff value or are closer to the values for the known responders indicate the patient sample is exhibiting responsiveness to the therapeutic agent and if the values are at or above the cutoff value or are closer to the values for the known non responders value, the cell sample is identified as a non responder to the therapeutic agent. In some embodiments an output of the biosensor at a defined period of time is classified as no response, weakly responsive or responsive. An output at a defined period of time is selected in order to classify the output into the categories. In other embodiments, the defined period of time is the end point of the time period for which the cells have been continuously monitored in the biosensor. In other embodiments, the time period is at least 60 minutes, 60 hours, or 120 hours. In embodiments, an output classified as no response, is indicated by an output value that differs from the output value of the baseline prior to administration of a therapeutic agent or a control cell not treated with the therapeutic agent no more than at least 20% or less, 15% or less, 10% or less, or 5% or less. In other embodiments, an output classified as weakly responsive is indicated by an output value that differs from the output value of the baseline prior to administration of a therapeutic agent or a control cell not treated with the therapeutic agent of at least 50% or less and greater than 5%. In other embodiments, an output classified as responsive is indicated by an output value that differs from the baseline prior to administration of a therapeutic agent or a control cell not treated with the therapeutic agent of at least greater than 50%. In embodiments, the control sample is a sample of the disease cells from the same subject and not treated with the therapeutic agent.

A further aspect of the methods described herein involves developing an algorithm that can be used to predict the efficacy of a therapeutic agent in an individual subject. The algorithm incorporates the values derived using the methods described herein, in combination with values assigned to one or more patient characteristics that define an aspect of an individual subject's health. The patient characteristics can include, but are not limited to, the presence of metastases, the location of metastases, nodal status, disease free interval from initial diagnosis of cancer to diagnosis of metastases, receipt of adjuvant chemotherapy, receipt of other drug therapies, receipt of radiation therapy, dominant site of disease, tumor mass size, body-mass index, number of tender joints, number of swollen joints, pain, disability index, physician global assessment, patient global assessment, Bath Ankylosing Spondylitis Functional Index, Bath Ankylosing Spondylitis Disease Activity Index, Bath Ankylosing Spondylitis Metrology Index, C-Reactive Protein, total back pain, inflammation, genetic status, history of other illnesses, other vital health statistics status, and any combinations thereof. The algorithm that incorporates these values would weight these values according to their correlation to disease progression in a population of patients with the disease that the therapeutic agent is intended to treat. Disease characteristics that did not demonstrate any correlation with differential response would not be included in the algorithm.

In one embodiment, the value placed on the patient characteristics can be derived from a regression analysis of the test results (i.e., values derived from the methods of determining responsiveness to a therapeutic agent, a perturbing agent, an activator agent, etc. as described herein), the patient characteristics, and the clinical outcome of a group of patients studied. From this analysis, an algorithm value can be derived. In one example, optimization of an algorithm using the tests in combination with variables based on patient characteristics data can be performed by dividing the test values into 10 intervals based on 9 equally spaced cut-points of width 0.10 beginning with 0.10. For each cut-point, a Cox regression can be run using an indicator variable which takes on the value "one" if a subject has an algorithm value less than or equal to the cut-point and "zero" otherwise. The hazard ratio, being the comparison of those at or below the cut-off, versus those above the cut-off, will be determined for each cut-point. The value of the cut-point that minimizes the estimated hazard ratio is then selected.

For example, it may be found that when a patient's total tumor mass is above a certain value, their responsiveness to a drug, as determined by the methods described herein, will not be sufficient to prolong the patient's potential progression free period beyond the median result found for those patients not responsive to the drug. In the case when a test result indicates that the drug is functional in the patient, and that they would otherwise be expected to benefit from it, the algorithm including the patient characteristics variables would report that the result is indeterminate since the tumor mass variable offsets the test result value.

Another aspect of the methods described herein provides a method for determining a cut-off value for a test that identifies patients likely or unlikely to respond to a targeted therapeutic agent. This method involves a) selecting a group of patients, each of whom has the same disease and is prescribed the same therapeutic, b) using the methods described herein to derive a test value for each subject within a group of patients, c) observing the health status of each member of the group of patients tested over a period of time sufficient for a significant percentage of the total patients tested to reach a predefined clinical endpoint and record the length of time required for each of the patients to reach, if they did, the predefined clinical endpoint, d) identifying two or more candidate cut-off values that are equidistant in value to the other, wherein each candidate cut-off value represents a value below which a patient is predicted to respond or not respond and above which a patient is predicted to respond in opposite manner of those whose scores fell below the cut-off value, e) using a statistical method to analyze the difference between the clinical endpoint periods for patients whose test value was at or below the cut-off and the clinical endpoint periods for those patients whose test value was above the cut-off, and f) selecting the cut-off value that results in the greatest percentage of patients who are predicted not to respond to the therapy amongst the group of candidate cut-off values that indicates there is a statistically significant difference between the group of patients above and below the cut-off value.

Using the methods described herein, it is possible to derive a numeric test result value for an individual subject that can be compared to the test value derived from other individuals with the same disease whose cells were tested with the same therapeutic. This makes it possible to predict the efficacy of a therapeutic on an individual subject by: a) recording the test result values for a group individual subjects who have the same disease and were tested with the same therapeutic, b) compiling those values into a list, c) ordering the list on the basis of test results values for the individual subjects tested on the basis of each individual subject's absolute numeric test value, and d) determining the percentile rank of an individual subject's test value, wherein the percentile rank of an individual subject's test value is predictive of the efficacy of the therapeutic agent for the disease in the individual subject.

Another embodiment includes analyzing the results obtained from a clinical trial testing the efficacy of the same therapy to estimate the percentile ranking of a particular result and then identifying the percentile rank for an individual subject's test value, and identifying the clinical trial end point result that corresponds to the same percentile ranking, wherein the clinical trial end point result at the same percentile ranking as the individual subject's test value is predictive of the clinical result an individual subject is likely to obtain from the therapeutic agent for the disease. The clinical trial end points can include, for example, time-to-progression period, progression-free survival period, overall survival period, objective response period, ACR response, change in Total Sharp Score, erosion score, and Joint Space Narrowing, clinical response, pain, disability index, clinical remission, body-surface area involvement, physicians global assessment, and psoriasis area and severity index.

Another embodiment includes a method to determine the statistical correlation between the test result values derived from the methods described herein and the clinical outcome for an individual who received the therapeutic that was tested. This method comprises: a) selecting a group of patients, each of whom has the same disease and is prescribed the same therapeutic, b) using the methods described herein to derive a test result value for an individual, c) compiling a list of test result values for each subject within a group of patients who have the same disease and were tested with the same therapeutic, d) observing the health status of each member of the group of patients tested over a period of time sufficient for a significant percentage of the total patients tested to reach a predefined clinical endpoint, e) recording the length of time required for each of the patients to reach, if they did, the predefined clinical end-point, analyzing the end-point data (e.g. time-to-progression period, progression-free survival, ACR response) in such a manner that the statistical relationship between the end point result and the test value is determined.

By way of example, once the results from a clinical trial are available, the determination of an estimate of the cut-off value—"C*"—proceeds as follows. Assuming that a Cox regression test indicates that the test value is predictive of a patient outcome, such as time-to-progression (TTP), the test values will be divided into 10 intervals based on 9 equally spaced cut-points of width 0.10 beginning with 0.10. For each cut-point, a Cox regression will be run using an indicator variable which takes on the value "one" if a subject has an assay value less than or equal to the cut-point, and "zero" otherwise. The hazard ratio, being the comparison of those at or below the cut-off versus those above the cut-off, will be determined for each cut-point. The value of the cut-point that maximizes the estimated hazard ratio will be selected for use in the subsequent pivotal phase of the study. For the final analysis, a Cox proportional hazard regression can be run with an indicator variable (below the cut-point versus above the cut-point). The final analysis can also include other putative predictive patient characteristic variables of TTP.

E. Therapeutic and Activator Agents

Often a when a patient is diagnosed with a particular disease or condition, there is a range of treatment options. In some cases, treatments may be very expensive or the side effects associated with the treatment may be severe so it would be useful to know whether the patient is likely to be a responder or a non-responder to a treatment. In addition, if a patient becomes resistant, it would be useful to know which other treatments might be efficacious now that the patient's diseased cells have become resistant.

In certain embodiments, any therapeutic agent or agents that are used in the treatment of a condition for which some patients respond and others do not respond can be analyzed in the methods described herein. For example, for cancer, a number of targeted immunotherapies are available including a number of different chimeric and humanized antibodies. For autoimmune conditions, molecules such as those targeted to inflammatory cytokines or their receptors may be analyzed. Examples of agents targeted to inflammatory cytokines are anti-TNF a agents, agents targeting interferon alpha, interleukins, and the like. Immunosuppressive agents such as corticosteroids, tacrolimus (FK-506 or TACR) (inhibits T-cell metabolism and proliferation), sirolimus (SIRO/ 81768), myocophenolic acids, mycophenolate mofetil (MMF), calcineurin inhibitors (CI), cyclosporin (CsA), and rapamycin (mTOR inhibitor).

In other embodiments, the methods involve testing of one or more therapeutic agents, perturbing agents (e.g., activator agents), or combinations thereof, for the ability to cause a change in a physiological parameter of the diseased cells from the individual subject. In embodiments, the therapeutic agents are also label free. In some embodiments, two or more therapeutic agents may be tested separately or in combination on separate samples of the diseased cells from the same patient. A therapeutic agent is selected that causes the greatest change in the cellular response or physiological characteristic at a lower dose than other therapeutic agents. Combinations of compounds may be determined that offer the greatest therapeutic effect. In embodiments, the determination may be as compared to healthy cells of the patient to determine therapeutic index and other individual safety and tolerance effects.

In some embodiments, when a therapeutic agent is a targeted therapeutic agent that affects a cellular pathway, the change in cellular responsiveness is measured in the absence or presence of an activator agent or perturbant of the pathway. A therapeutic agent is selected that inhibits the cellular responsiveness to the perturbant of the pathway as compared to baseline measurement and optionally, as compared to other therapeutic agents.

In other embodiments, when a therapeutic agent is a targeted therapeutic agent that binds to a cell surface receptor, the change in cellular responsiveness is measured in the absence or presence of an activator agent or perturbant that binds to the receptor. In embodiments, the therapeutic agent is administered to the cell sample before or after the activator or perturbant. In embodiments, the activator agent or perturbant is label free. A therapeutic agent is selected that inhibits the cellular responsiveness to the activator agent or perturbant as compared to baseline measurement and optionally, as compared to other therapeutic agents, regardless of the density of the cell surface receptors. In some embodiments, a therapeutic agent is selected that inhibits the action of the activator agent or perturbant independent of the density of cell receptors.

The change in the physiological parameter can be an increase or a decrease in the parameter as compared to baseline or healthy cell control. The changes could represent full agonism, superagonism, irreversible agonism, selective agonism, co-agonism, inverse agonism, or partial limiting agonism, reversible and irreversible antagonism, competitive antagonism, non-competitive antagonism, un-competitive antagonism. The changes can occur sooner, later or not at all as compared to an appropriate control. The changes could be selected to occur for a longer or shorter period of time. Changes could be selected that are reversible or irreversible.

For example, a therapeutic agent that results in a decrease in cell signaling would be selected for treatment of an autoimmune condition. Peripheral blood cells that respond to an agent that inhibits the action of a cytokine show a decrease in cell signaling. In another example, for disease cells responsive to an anticancer agent, such as a humanized antibody targeted to a receptor like Her2, the disease cells would show a significant reduction in EGF family pathway signaling. In other cases, for disease cells responsive to an anti-angiogenic agent, the disease cells would show a reduction in VEGF pathway signaling or reduction in proliferative ability. The CReMS response or physically observable characteristic measured for each type of agent is dependent upon the intended physiological response the drug was designed to illicit and can be as specific or general as needed. The key is the use of the CReMS for physiological measurement of a live cell for a period of time to test the response the drug was intended to alter.

A particular therapeutic agent or agents can be administered to the diseased cells, and optionally, healthy cells to determine the effectiveness of the particular therapeutic or therapeutics. Diseased cells and/or healthy cells can also be untreated so as to compare the effect of the therapeutic or therapeutics on treated and untreated diseased and/or healthy cells. A single therapeutic can be administered to determine how a subject will respond to the therapeutic treatment. In another embodiment, a panel of different therapeutics can be administered to cells of a particular subject.

In certain embodiments, a cutoff value for efficacy of a therapeutic agent to inhibit activation of a cellular pathway is determined in one embodiment by adding the drug and measuring the physiologic response. In another embodiment, the pathway is stimulated with and without drug pre-treatment. Changes to the physiologic baseline signal or reductions of the stimulation signal by the drug at the 85% confidence interval or ideally greater than the 90% confidence interval or more ideally greater than the 95% or 99% confidence interval are deemed efficacious. In embodiments, a cutoff value for efficacy of a therapeutic agent that inhibits cell proliferation or enhances cell killing is determined by recording the physiologic response over time. Reductions to the physiologic baseline signal or deviation from the temporal pattern as compared to non-treated or healthy cells or a combination thereof by the drug at the 85% confidence interval or ideally greater than the 90% confidence interval or more ideally greater than the 95% or 99% confidence interval are deemed efficacious.

The sensitivity and specificity of the therapeutic agent for treating the disease of an individual subject is determined by comparing the cellular physiologic pathway response as measured by the CReMS to determine that the drug is working as it was designed on a specific target and determining that a cutoff value for efficacy has been attained.

In some embodiments, the activator agent and/or the therapeutic agent are titrated in order to obtain the Hill Slope, $EC_{50}$ or $IC_{50}$ value for either agent. The data obtained from the activating agent titration and/or the therapeutic agent titration may be used to assess the potency (what concentration achieves one half maximal effect) and or efficacy (maximum achievable effect) of either agent. A further aspect includes a method of predicting efficacy of a therapeutic agent in an individual subject using diseased cells obtained from the subject, by titrating an activator agent or a therapeutic agent in order to develop an IC50 value, where the activating agent reduces cellular pathway activity and the therapeutic agent agonizes cellular pathway activity.

Therapeutic agents can include without limitations agents that are targeted to a particular cellular pathway and/or agents that inhibit cell proliferation or cause cell killing. Examples of pathways that therapeutic agents target include MAPK-PK, RAS/RAF, RHO, FAK1, MEK/MAPK, MAK, MKK, AKT, EGF receptor, Her2 receptor, Her 3 receptor, Her 4 receptor, PIK3/P1'EN, VEGF receptor pathway inhibitors, cell adhesion, TGFbeta/SMAD, WNT, Hedgehog/GLI, HIF1 alpha, JAK/STAT, Notch, control of G1/S transition, DNA damage control, and apoptosis. In some embodiments, the therapeutic agents target cellular pathways involved in cell cycle regulation. Exemplary targeted therapeutic agents that affect cell cycle regulation include those targeted to CDK4, CDK6, PD-1, and cyclins (e.g., cyclins A, B, C, D, E, or F, and G1/S cyclins). In some embodiments, the targeted therapeutic agents target aromatase enzyme.

In other embodiments, the therapeutic agents are selected from a number of small molecule and antibody drugs such as trastuzumab, pertuzumab, lapatinib, docetaxel, tamoxifen, cisplatin, abraxane, paclitaxel injection, brentuximab vedoton, everolimus, pemetrexed, exemestane, ofatumumab, bevacizumab, alemtuzumab, irinotecan, bicalutamide, oxaliplatin, cetuximab, visomedegib, toremifene citrate, fulvestrant, gemcitabine, imatinib, ixabepilone, topeotecan, axitinib, romidepsin, cabrazitaxel, sorafenib, infliximab, lenalidomide, rituximab, dasatinib, sunitinib, erlotinib, nilotinib, paclitaxel, temozolomide, trioxide, panitumumab, bortezomib, azacitidine, pazopanib, crizotinib, capecitabine, ipilimumab, vemurafenib, goserelin acetate, abiraterone, a BH3 mimetic, navitoclax, anastrozole, letrozole, an aromatase inhibitor, cyclophosphamide, doxorubicin, methotrexate, fluorouracil, ixabepilone, carboplatin, aflibercept, temsirolimus, irbritumomab, abiraterone, custirsen, neratinib, enzalutamide, nivolumab, palbociclib, regorafenib, entinostat, afatinib, ARN-509, ARN-810, BIND-014, dabrafenib, daratumumab, lambrolizumab, LDK378, MM-121, sym004, trastuzumab emtansine, tivozanib, trametinib, axitinib, LY2835219, MPDL320A, obinutuzumab, Sym004, Tositumomab, trametinib, necitumumab, ramucirumab, and combinations thereof. The targets of these therapeutic agents are known. Additional combinations of therapeutic agents can be selected using the Chou and Talalay method (Chou, Cancer Res., 70(2):440-446 (2010)).

In one embodiment, the method for determining therapeutic efficacy of an agent for a disease in an individual subject comprises: administering the agent to at least one isolated disease cell sample from the individual subject in a cellular response measurement system (CReMS); and determining whether a change in a cellular response parameter of the cell sample to the agent occurs as compared to a baseline measurement, wherein the change in cellular response indicates that the agent has therapeutic efficacy for the disease in the individual subject. In embodiments, a method further comprises administering to at least one isolated disease cell sample from the individual subject in a cellular response measurement system an activator agent or perturbant that perturbs the cellular response pathway before or after administering the therapeutic agent.

In some embodiments, the therapeutic agent is targeted to a cell surface receptor and/or a cellular pathway. In that case, the sample is contacted with a therapeutic agent before the sample is activated with an activator agent or perturbant of the pathway. In other embodiments, the activator agent or perturbant comprises a specific growth factor, vascular endothelial growth factors, phosphatidyl inositol, epidermal growth factors, hepatocyte growth factors, m-CSF, RANK ligand, Tumor Necrosis Factors (TNF-α), neuregulin, estrogen, progesterone, folate, adenosine triphosphate, and FAS Ligand, Platelet derived growth factors (PDGF), or other agents of cellular pathway or signaling stimulation such as the subject's plasma or serum, Na+, K+, Mg+, Cl—, Ca+2, glucose, glutamine, histidine, mannitol, and tryptophan, antibiotics (rapamycin), essential and non-essential amino acids, vitamins, other organic compounds, trace minerals and inorganic salts, serum, cell extracts, fractionated cell extracts or fractionated serum, extracellular signaling factors, intracellular signaling factors, insulin, transferrin, sodium selenite, hydrocortisone, ethanolamine, phosphophorylethanoloamine, triidothyronine, sodium pyruvate, L-glutamine. In other embodiments, therapeutic agents are those that affect diseased cells by inhibiting cell proliferation, enhancing cell killing, and rendering the cell unresponsive or less responsive to signals that lead to a diseased state. Examples of such therapeutic agents include cyclophosphamide, 5-FU, capecitabine, and other pyrimidine drugs, others SN-38 metabolite analogs (Ex. irinotecan), taxols, and platinum containing drugs (Ex. cisplatin).

In some embodiments, the response of a sample to one or more of these agents can also be measured in the presence or absence of a growth factor that stimulates cell proliferation or of an anti-apoptotic agent. Growth factors that stimulate cell proliferation include growth hormone, epidermal growth factor, vascular endothelial growth factor, platelet derived growth factor, hepatocyte growth factor, transforming growth factor, fibroblast growth factor, nerve growth factors, and others known to those practiced in the art. Anti-apoptotic agents include compounds that regulate anti-apoptotic proteins or pathways (Ex. taxols on Bcl-2 protein activity and Gefitinib for control of the anti-apoptotic Ras signaling cascade).

For example, for a particular subject diagnosed with breast cancer and determined to be Her2 positive, cells isolated from that subject can be tested for responsiveness to particular anti-cancer therapeutics, especially anti-Her2 therapeutics. For instance, cells from the Her2+ subject can be tested for responsiveness to trastuzumab or lapatinib in the presence or absence of epidermal growth factor (EGF) and/or homologous structured peptides, neuregulin, or heregulin. In an embodiment, cells from the subject can be seeded on a biosensor. In embodiments, cells are label free whole cells. Such cells can be both cells from the breast cancer tumor and healthy breast tissue. Trastuzumab or lapatinib can be administered to a sample of diseased cells and, optionally, a sample of healthy cells. In some embodiments, the cell samples treated with trastuzumab are then contacted with Her receptor activator such as neuregulin. A sample of both diseased and healthy cells can remain untreated. A cellular response is determined using a cellular response measurement system (CReMS). In embodiments, the cellular response is determined after 1 hour or less. The effectiveness of trastuzumab treating the cells of the particular subject can then be determined in the presence or absence of perturbation of the pathway.

In certain embodiments, an agent is selected that inhibits the cellular response of the individual subject's cell sample to an activator of the cellular pathway, activator of cell proliferation, or inhibitor of apoptosis. When a number of different therapeutic agents that activate the same or different pathways are evaluated in a method of the disclosure, an agent is preferably selected that can inhibit the activator or inhibitor response at a lower concentration than the others.

In similar embodiments, therapeutic agents are those that affect diseased cells by agonizing or partially agonizing cellular activity where reduced activity has led to the diseased state.

The test can measure the effectiveness of a drug in a range of concentrations from below 1 nM to greater than 100 uM generally with less than 20% standard deviation and optimally with less than 5% standard deviation. The compound test range will correspond to dosing levels as defined on a drug packaging label known as the maximum tolerated dose. Unlike most tests that cannot ascertain the number of live cells in the actual set of cells in the test, this test is only working with the live cells as determined in a quality control and baseline physiologic determination step at the beginning of the test. The result of this feature reduces the variance of the test result. The test can be conducted using a temperature, oxygen, humidity, and carbon dioxide range generally acceptable for cell viability commonly known to those practiced in the art. In some cases, a preferred temperature range is between 25° C.-40° C. In other cases the temperature may be optimized further to ±0.5° C. within this range for specific perturbations and maintained using standard temperature controlled incubator cabinets.

In another embodiment, samples of the diseased cells from an individual can be tested for responsiveness to a panel of anticancer therapeutics. For cancer, a number of small molecule and antibody drugs are available. Examples of such therapeutic agents include trastuzumab, pertuzumab, lapatinib, docetaxel, tamoxifen, cisplatin, abraxane, paclitaxel injection, brentuximab vedoton, everolimus, pemetrexed, exemestane, ofatumumab, bevacizumab, alemtuzumab, irinotecan, bicalutamide, oxaliplatin, cetuximab, visomedegib, toremifene citrate, fulvestrant, gemcitabine, imatinib, topeotecan, axitinib, romidepsin, cabrazitaxel, sorafenib, infliximab, lenalidomide, rituximab, dasatinib, sunitinib, erlotinib, nilotinib, paclitaxel, temozolomide, trioxide, panitumumab, bortezomib, azacitidine, pazopanib, crizotinib, capecitabine, ipilimumab, vemurafenib, goserelin acetate, abiraterone, a BH3 mimetic, navitoclax, anastrozole, letrozole, an aromatase inhibitor, cyclophosphamide, doxorubicin, methotrexate, fluorouracil, and combinations thereof.

For instance, samples of cells collected from a Her2+ subject can tested against a panel of anti-breast cancer therapeutics, including anti-Her2 therapeutics. In an embodiment, each sample of cells from the subject can be administered one of the anti-breast cancer therapeutics. A panel of anti-breast cancer therapeutics can include, but are not limited to, trastuzumab, pertuzumab, lapatinib, docetaxel, tamoxifen, cisplatin, a BH3 mimetic, an aromatase inhibitor, cyclophosphamide, doxorubicin, methotrexate, fluorouracil, NeuVax™ (E75 peptide administered with adjuvant sargramostim (rGM-CSF)), and combinations thereof. The aromatase inhibitor can be at least one of aromatase inhibitor is anastrozole, letrozole, or exemestane. The BH3 mimetic can be navitoclax.

In one embodiment, an anti-breast cancer therapeutic can be a Her/Neu receptor family activity modulators (e.g., pertuzumab), cellular growth factor receptor modulators (e.g., modulators of vascular endothelial growth factor (VEGF) receptors), mitogen activated protein kinase (MAPK) pathway modulators, (PI3K) pathway modulators, a BH3 mimetic, an aromatase inhibitor, or combinations thereof.

Methods of the invention include administering candidate therapeutics to a subject's cells to determine safety and to determine therapeutic effectiveness. Additionally, administration of a candidate therapeutic to a subject's diseased cells may be used as a method of selecting the proper patient population for a phase II or III clinical trial. Methods of the invention include testing diseased cells against known therapeutic combinations. Additionally, methods of the invention include testing known and candidate therapeutics.

Methods of the invention also include administering combinations of therapeutic agents to determine if a particular combination of agents produces a more effective result (i.e., amelioration or cure of disease symptoms). A combination of therapeutic agents is two or more therapeutic agents administered to the same cell sample. In an embodiment of the invention, the combination of therapeutic agents is administered to a cell sample concurrently. In an embodiment, at least one therapeutic agent is administered to the cell sample at a time different than the administration of the other at least one therapeutic agent of the combination.

After administration of therapeutic agents to a cell sample, real time data can be collected on multiple aspects of the cell sample. For instance, pH and temperature can be measured. Additionally, other factors, such as "cell death factors", can be determined. A cell death factor as determined by a CReMS can be a change in a physicochemical property as measured by the CReMS. For instance, cancer cells will attach to a surface and provide a baseline reading for a refractive index. Administration of a therapeutic agent that promotes cancer cell death would cause a change in the refractive index since the cancer cells in a sample would round up and detach from a surface. This could be measured by an optical biosensor utilizing surface plasmon resonance in a continuous real-time manner.

In one embodiment, the invention provides a method for determining therapeutic efficacy of an agent for a particular subject by administering the agent to a disease cell sample from the subject in a CReMS and determining the physiologic response of the cell sample to the agent compared to a baseline measurement, wherein the physiologic response indicates therapeutic efficacy of the agent. The agent administered to a disease cell sample can be a single agent or two or more agents. When the agent is two or more agents, the two or more agents can be administered concurrently or at different times. For instance, one agent can be administered to a cell sample and a second agent can be administered a later time (e.g., 10 minutes later). A method can also include administering a placebo to a diseased cell sample. A method can also include administering the agent(s) to be tested on a healthy cell sample.

In certain embodiments, the methods involve determining an optimal dose range for a particular therapeutic. Determination of a dose range allows for proper design of clinical trials and/or allows the physician to balance efficacy with detrimental side effects. In embodiments, a method comprises administering a range of doses of a therapeutic agent to separate samples of diseased cells from the same patient, and determining the dose range that results in a change in a physiological parameter of the cells as described herein as compared to baseline and/or healthy control cells.

Once any of the methods described herein are used to determine whether an individual subject's disease cells respond to one or more therapeutic agents, the results are communicated to a health care worker to allow for selection of a therapeutic agent for treatment of the subject. In embodiments, the methods further comprise administering the selected therapeutic agent to the subject.

F. Determining the Status of a Cellular Pathway in an Individual Subject

Many diseases are caused by dysfunctional cellular pathways, as described above. In many cases, particular genetic mutations are often associated with these dysfunctional pathways, leading, for example, to a protein receptor that is over- or under-expressed. A variety of therapeutics have been designed to specifically target biomarkers thought to be characteristic of a given disorder. Unfortunately, targeted therapeutic agents are often only effective in less than half of the patients that receive them, at least in part because the nature of a patient's disease is not simply a function of the presence of a specific genetic biomarker. Accordingly, identification of disease biomarkers or gene signatures is insufficient to accurately predict drug efficacy. The activity of cellular pathways involved in the disease process is too complex to be captured with a static quantification of a genetic condition. As described above, the efficacy of a therapeutic agent in an individual subject can be determined by exposing a diseased cell sample from the subject to the therapeutic agent, alone or in combination with a perturbing agent, and measuring the physiologic effect of the agents on treated cells.

It is also possible, in another embodiment, to determine responsiveness of an individual subject to a targeted therapeutic agent by determining the status of the cellular pathway targeted by the agent in a cell sample obtained from the subject. The activity of a disease-causing pathway can be measured using an agent known to perturb a specific cellular pathway when the cellular pathway is functioning normally. This embodiment reflects the observation that the functioning of a cellular pathway in the context of a viable diseased cell is at the root of disease activity, which is not simply due to the degree of over-expression of a protein residing within that pathway.

Accordingly, in one aspect, the invention provides a method of determining the functional status of a cellular pathway in diseased cells obtained from an individual subject, by contacting a diseased cellular sample obtained from the subject with a perturbing agent (e.g., an activating agent) known to perturb a specific cellular pathway when the pathway is functioning normally. One or more physiological response parameters can be measured in viable cells in the sample (e.g., in a cellular response measurement system (CReMS)), and mathematical analysis of the continuous measurements can be used to determine whether a change in the physiological response parameter occurs in the presence of the perturbing agent, relative to a suitable control. A change in one or more physiological response parameters in the presence of the perturbing agent, compared to a suitable control, indicates that the cellular pathway targeted by the perturbing agent is functional in the individual subject.

In another aspect, the invention provides a method of selecting a targeted therapeutic agent for an individual subject, by contacting a diseased cellular sample obtained from the subject with a perturbing agent known to perturb a specific cellular pathway when the pathway is functioning normally. One or more physiological response parameters can be measured in viable cells in the sample (e.g., in a cellular response measurement system (CReMS)), and mathematical analysis of the continuous measurements can be used to determine whether a change in the physiological response parameter occurs in the presence of the perturbing agent. A change in one or more physiological response parameters in the presence of the perturbing agent, compared to a suitable control, indicates that the cellular pathway targeted by the perturbing agent is functional in the individual subject, and, accordingly, that the subject will be responsive to targeted therapeutic agents that target the same cellular pathway. In some embodiments, the method further comprises administering the targeted therapeutic agent to the subject. This embodiment allows the responsiveness of an individual subject to a targeted therapeutic agent to be determined, by determining the functional status of the cellular pathway which the therapeutic agent affects.

In a particular embodiment, the functional status of the cellular pathway in the individual subject is previously unknown. In another particular embodiment, the cellular sample obtained from the subject contains diseased cells, and/or can be label-free.

The effect of the perturbing agent can be measured by monitoring at least one physiological response parameter of the cell sample for a defined period of time sufficient to detect a change in this parameter in viable cells in the sample, in the presence of the perturbing agent. In some embodiments, the sample consists essentially of viable cells.

The perturbing agent can include those perturbing agents (e.g., activating agents) described herein. For example, the perturbing agent can be a protein, a peptide, a nucleic acid, a metabolite, a ligand, an organic molecule, a signaling factor, a biochemical, or combinations thereof. Certain perturbing agents include but are not limited to agonists or antagonists, growth factors, cytokines, hormones, small molecules designed to agonize or antagonize specific cellular activities, enzymes, peptides and peptidic fractions of any of the above, antibodies or fragments of antibodies.

Examples of pathways targeted by the perturbing agent and the therapeutic agent include MAPK-PK, RAS/RAF, RHO, FAK1, MEK/MAPK, MAK, MKK, AKT, EGF receptor, Her2 receptor, Her 3 receptor, Her 4 receptor, estrogen receptors, progesterone receptors, androgen receptors, GPER30, PIK3/PTEN, VEGF receptor pathway inhibitors, cell adhesion, TGFbeta/SMAD, WNT, Hedgehog/GLI, HIF1 alpha, JAK/STAT, Notch, control of G1/S transition, DNA damage control, and apoptosis. In some embodiments, the agents target cellular pathways involved in cell cycle regulation. Exemplary agents that affect cell cycle regulation include those targeted to CDK4, CDK6, PD-1, and cyclins (e.g., cyclins A, B, C, D, E, or F, and G1/S cyclins). In some embodiments, the agents target aromatase enzyme.

In exemplary embodiments, the perturbing agent and the targeted therapeutic agent act on a cellular pathway involved in at least one of the following cellular processes: MAP kinase signaling, apoptosis, PI3K/Akt/mTOR signaling, chromatin/epigenetic regulation, cellular metabolism, cell cycle control, immunology and inflammation, development and differentiation, and/or cytoskeletal regulation and adhesion. Exemplary perturbing agents, and the pathways they target, are provided in Tables 1-9 below.

TABLE 1

Cell Process - MAP Kinase Signaling
Pathways
Mitogen-Activated Protein Kinase Cascades
MAPK/Erk in Growth and Differentiation
G-Protein-Coupled Receptors Signaling to MAPK/Erk
SAPK/JNK Signaling Cascades
Signaling Pathways Activating p38 MAPK

| Ligands/Perturbing Agents | Pathway & examples of members | References |
|---|---|---|
| Mitogens | Ras, Raf, Mos, MEK, Erk, MAPK | *Cell. Mol. Life Sci.* 64(21), 2771-89 (2007) Regulatory mechanisms of mitogen-activated kinase signaling. |
| Growth Factors - EGF, FGF, PDGF | MLK3, TAK, DLK, MKK, P38, MAPK, MEK, Erk | *FASEB J.* 22(4), 954-65 (2008) Phosphatase-mediated crosstalk between MAPK signaling pathways in the regulation of cell survival |
| Pro- & Anti-Inflammatory cytokines - IL-1, IL-6, IL-10, TNFalpha | MEKK, MLK, ASK, MKK, SAPK, JNK, MAPK | Expert Opin Ther Targets. 2008 February; 12(2): 171-83. doi: 10.1517/14728222.12.2.171 - Pro-inflammatory cytokine-induced SAPK/MAPK and JAK/STAT in rheumatoid arthritis and the new anti-depression drugs |
| Stress - temperature, heat shock, osmotic pressure, pressure, partial pressure of oxygen or CO2 | MEKK, MEK, Erk, BMK, SAPK, p38, MAPK | Biochem&Biophys Res Comm Volume 239, Issue 3, 29 Oct. 1997, Pages 840-844 Hypoxia and Hypoxia/Reoxygenation Activate p65PAK, p38Mitogen-Activated Protein Kinase (MAPK), and Stress-Activated Protein Kinase (SAPK) |
| GPCR ligands - dopamine, 5-HT, histamine acetylcholine, amino acids and ions (glutamate, calcium, GABA), nucleotides, prostaglandins, leukotrienes, chemokines, thrombin, angiotensin | Erk, JNK, p38, MAPK | *Oncogene* 26(22), 3122-42 (2007) G protein regulation of MAPK networks |

TABLE 2

Cell Process - Apoptosis Pathways
Apoptosis (Overview)
Inhibition of Apoptosis
Death Receptor Signaling
Mitochondrial Control of Apoptosis

| Ligands/Perturbing Agents | Pathway & examples of members | References |
|---|---|---|
| Trophic factors - Ex. NGF, neutrophins, BDNF | PKC & PI3K/AKT & Bad, Bcl, Bak, Bax, BID or Bim, Noxa, Puma, Caspase | Nature Reviews Molecular Cell Biology 9, 378-390 (May 2008) | doi: 10.1038/nrm2393 - Expansion and evolution of cell death programmes |

TABLE 2-continued

Cell Process - Apoptosis Pathways
Apoptosis (Overview)
Inhibition of Apoptosis
Death Receptor Signaling
Mitochondrial Control of Apoptosis

| Ligands/Perturbing Agents | Pathway & examples of members | References |
|---|---|---|
| TNF, TRAIL | ASK, JNK, P53 & NIK, NF-kB, Caspase, ROCK | *Biochim Biophys Acta.* 2011 June; 1807(6): 735-45. doi: 10.1016/j.bbabio.2011.03.010. Recent advances in apoptosis, mitochondria and drug resistance in cancer cells |
| FasL | Caspase, BH3, Bid, XIAP, Bcl-2-regulated apoptotic pathway, Bax/Bak, MOMP | *Cell Death Differ.* 2012 January; 19(1): 42-50. doi: 10.1038/cdd.2011.121. Fas death receptor signaling: roles of Bid and XIAP |

20

TABLE 3

Cell Process - PI3 Kinase/Akt/mTOR Signaling
Pathways
PI3K/Akt Signaling
PI3K/Akt Binding Partners Table
PI3K/Akt Substrates Table

| Ligands/Perturbing Agents | Pathway & examples of members | References |
|---|---|---|
| Integrins bind ECM/RGD peptides | PI3K, FAK, ILK, PDK, Akt | Integrin signalling during tumour progression Nature Reviews Molecular Cell Biology 5, 816-826 (October 2004) doi: 10.1038/nrm1490 |
| Insulin | IR, IGFr, PI3K, Akt, mTOR, Bcl | *Diabetes* February 2003 vol. 52 no. 2 227-231 doi: 10.2337/diabetes.52.2.227 Insulin Activation of Phosphatidylinositol 3-Kinase |
| NRG, HRG, IGF | PI3K, PDK, Akt, mTOR | *Curr Cancer Drug Targets* 8(3), 187-98 (2008) The PTEN/PI3K/AKT signalling pathway in cancer, therapeutic implications. |
| Cytokines - GM-CSF, IL-3 | Jak, Ras, PI3K, PDK, Akt | The EMBO Journal (2006) 25, 479-489 doi: 10.1038/sj.emboj.7600948, & *Protein Kinase Activity of Phosphoinositide 3-Kinase Regulates Cytokine-Dependent Cell Survival* PLOS Biology Published: Mar. 19, 2013 DOI: 10.1371/journal.pbio.1001515 |
| Rapamycin | PIKK, PI3K, Akt, 4E-BP1, Raptor, PDK | *The tor pathway: a target for cancer therapy.* Nature Reviews Cancer 4, 335-348 (1 May 2004) | doi: 10.1038/nrc1362 |
| Breakpoint cluster region protein (BCR) | PI3K, PDK, Akt, mTOR, PKC | *Leukemia.* 2004 February; 18(2): 189-218 JAK/STAT, Raf/MEK/ERK, PI3K/Akt and BCR-ABL in cell cycle progression and leukemogenesis |

The two TORCs and Akt. *Dev. Cell* 12(4), 487-502 (2007)

TABLE 4

Cell Process - Chromatin/Epigenetic Regulation

| Ligands/Perturbing Agents | Pathway & examples of members | References |
|---|---|---|
| See steroid/hormone ligands of nuclear receptors, see ligands of Wnt pathway, see MAPK pathway ligands, see PI3K pathway ligands | KMT, MLL, KDM, UTX, DOT1L, BRD, TET, SirT1, Hat, SNF, DNMT, EZH | *Epigenetics & Chromatin* 2013, 6:28 doi: 10.1186/1756-8935-6-28 Epigenetic coordination of signaling pathways during the epithelial-mesenchymal transition & Cancer Res. 2011 Mar. 1; 71(5): 1752-1762. doi: 10.1158/0008-5472.CAN-10-3573 Epigenetic Silencing Mediated Through Activated PI3K/AKT Signaling in Breast Cancer |

TABLE 5

Cell Process - Cellular Metabolism
Pathways
Insulin Receptor Signaling
AMPK Signaling
Warburg Effect

| Ligands/Perturbing Agents | Pathway & examples of members | References |
|---|---|---|
| Stress, low glucose, heat shock, thrombin, histamine, adrenergic receptor ligands | AMPK, PLC, CaMKK | (2011) AMP-activated protein kinase: nature's energy sensor. *Nat. Chem. Biol.* 7(8), 512-8. |
| Insulin | AMPK, PI3K, Akt, Ras, Raf, Erk, | (2010) AMP-activated protein kinase and its downstream transcriptional pathways. *Cell. Mol. Life Sci.* 67(20), 3407-23 |
| Glucose, lactate, citrate | Glucose transporter & metabolism, Ras, PFK, FAS, Krebs Cycle,, AKT. Bim/Bad/Bcl | (2010) The Warburg effect and mitochondrial stability in cancer cells. *Mol. Aspects Med.* 31(1), 60-74 & (2011) Aerobic glycolysis: meeting the metabolic requirements of cell proliferation. *Annu. Rev. Cell Dev. Biol.* 27, 441-64 |
| Insulin & growth factors | PI3K, Akt, mTOR, glycolysis | (2011) Regulation of cancer cell metabolism. *Nat. Rev. Cancer* 11(2), 85-95 |

TABLE 6

Cell Process - Immunology and Inflammation
Pathways
Jak/Stat Signaling: IL-6 Receptor Family
NF-κB Signaling
TLR Pathway
B Cell Receptor Signaling
T Cell Receptor Signaling

| Ligands/Perturbing Agents | Pathway & examples of members | References |
|---|---|---|
| TNF | TNFR, NFkB, TRAD, TRAF, TAK, TAB, NEMO, NIK, IKK, MEKK, RelA, RelB, kB, | (2011) Regulation of TNF-induced NF-κB activation by different cytoplasmic ubiquitination events. *Cytokine Growth Factor Rev.* 22(5-6), 277-86 |
| IL-1 | IL1R, IRAK, MydBB, TRAF, TAB, TAK, NEMO, NFkB, RelA, RelB | (2008) Shared principles in NF-kappaB signaling. *Cell* 132(3), 344-62 |

TABLE 6-continued

Cell Process - Immunology and Inflammation
Pathways
Jak/Stat Signaling: IL-6 Receptor Family
NF-κB Signaling
TLR Pathway
B Cell Receptor Signaling
T Cell Receptor Signaling

| Ligands/Perturbing Agents | Pathway & examples of members | References |
| --- | --- | --- |
| Fas/DR ligands | ASK, TRADD, FADD, MKK, JNK, Caspases, FLIPs, Bid, ICAD, CAD, PARP, Lamins | (2011) Non-canonical NF-κB signaling activation and regulation: principles and perspectives. *Immunol. Rev.* 244(1), 44-54 |
| Mitogens, Growth Factors and Hormones | | See individual references |
| Bone morphogenic protein 2 | NFkB | Mohan et al, 1998 |
| Bone morphogenic protein 4 | NFkB | Mohan et al, 1998 |
| Connective tissue growth factor CCN2 | NFkB | Gao et al, 2005 |
| Corticotropin-releasing Hormone | NFkB | Zbytek et al, 2004 |
| Endothelin-1 | NFkB | Gerstung et al, 2007 |
| Epidermal Growth Factor | NFkB | Biswas et al, 2000; Sethi et al, 2007 |
| Estrogen/beta-estradiol | NFkB | Hirano et al, 2006 |
| Folicle Stimulating Hormone | NFkB | Delfino & Walker, 1998 |
| Gastrin | NFkB | Ogasa et al, 2003 |
| GMCSF | NFkB | Ebner et al, 2003 |
| Hepatocyte Growth Factor | NFkB | Yao et al, 2004; Kaibori et al, 2004; Shen et al, 1997 |
| Insulin | NFkB | Bertrand et al, 1995; Madonna et al, 2007 |
| Insulin-like growth factor 1 | NFkB | Liu et al, 2001 |
| Lysophosphatidic acid | NFkB | Raj et al, 2004; Hwang et al, 2006; Chen et al, 2008 |
| M-CSF | NFkB | Brach et al, 1991 |
| Mullerian Inhibiting Substance | NFkB | Hoshiya et al, 2003 |
| Nerve Growth Factor | NFkB | Wood, 1995; Carter et al, 1996 |
| Neurokinin A | NFkB | Sun et al, 2008 |
| Pigment epithelium-derived factor (PEDF) | NFkB | Yabe et al, 2001 |
| Platelet Activating Factor (PAF) | NFkB | Fernandes et al, 2003; Seo et al, 2006 |
| Platelet-Derived Growth Factor | NFkB | Olashaw et al, 1992 |
| Plant steroids (diosgenin, hecogenin, tigogenin) | NFkB | Corbiere et al, 2003 |
| Progastrin | NFkB | Rengifo-Cam et al, 2007; Umar et al, 2008 |
| Prostratin | NFkB | Williams et al, 2004 |
| Relaxin | NFkB | Ho et al, 2007 |
| Resistan | NFkB | Silswal et al, 2005 |
| All-trans retinoic acid | NFkB | Farina et al, 2002; Mathieu et al, 2005 |
| RET/PTC3 Fusion oncoprotein | NFkB | Russell et al, 2003 |
| S100B | NFkB | Adami et al, 2004 |
| Serum | NFkB | Baldwin et al, 1991 |
| Sulphatide (L-selectin crosslinker) | NFkB | Turutin et al, 2003 |
| TGF-alpha | NFkB | Lee et al, 1995 |
| TGF-beta2 | NFkB | Lu et al, 2004 |
| Thromboxane | NFkB | Wei et al, 2007 |

TABLE 7

Cell Process - Development, and Differentiation
Pathways
Hippo Signaling
TGF-β Signaling
Hedgehog Signaling
Notch Signaling
Wnt/β-Catenin Signaling
Angiogenesis
Nuclear Receptor Signaling
ErbB/HER Signaling
Ras Signaling

| Ligands/Perturbing Agents | Pathway & examples of members | References |
|---|---|---|
| FGF, IGF, VEGF, SLIT, PDGF | PI3K/Akt | Angiogenesis - pathway map |
| estradiol, androgen, testosterone | hormone/steroid and non-steroid activated signaling | Nuclear Receptor Signaling - pathway map |
| epidermal growth factors, neuregulins, or heregulins. | PI3K & MAPK | ErbB/HER Signaling-pathway map |
| R-spondin, Wnt | ZNRF, Frizzled, WntR, PAR, GSK, Dsh, LGR, catenin, WTX, APC | (2009) Wnt/beta-catenin signaling: components, mechanisms, and diseases. *Dev. Cell* 17(1), 9-26. & (2009) PARsing the phrase "all in for Axin" - Wnt pathway targets in cancer. *Cancer Cell* 16(5), 366-8 |
| E-cadherin binds ECM peptide sequences, catenins | Src, catenin, CBP, GSK | Journal of Mammary Gland Biology and Neoplasia October 2003, Volume 8, Issue 4, pp 435-447 Wnt-Cadherin Connections in Normal and Neoplastic Mammary Epithelium |
| TACE, ADAM, Epsin, Neur, Mib, juxtacrin factors, DLL, JAG | NOTCH, Fringe, Furin, Delta Jagged, NIC, presenilin | (2011) Notch signaling in solid tumours: a little bit of everything but not all the time. *Nat. Rev. Cancer* 11(5), 338-51 & (2011) Notch signaling: simplicity in design, versatility in function. *Development* 138(17), 3593-612. & (2011) Notch signalling in T-cell lymphoblastic leukaemia/lymphoma and other haematological malignancies. *J. Pathol.* 223(2), 262-73 |
| Hh, Shh, Dhh | CDO, BOC, Ptch, Smo, Gli, KIF, myc, cyclins D, E | (2010) Interactions between Hedgehog proteins and their binding partners come into view. *Genes Dev.* 24(18), 2001-12 & (2009) Paracrine Hedgehog signaling in cancer. *Cancer Res.* 69(15), 6007-10 & (2011) The Hedgehog's tale: developing strategies for targeting cancer. *Nat. Rev. Cancer* 11(7), 493-501. |
| TGF | SARA, Smad, Smurf, Ras, ERK, TAK, TAB, NLK, MKK, p28, JNK, Myc, Max, Fos, Jun | (2010) TGFbeta signalling: a complex web in cancer progression. *Nat. Rev. Cancer* 10(6), 415-24. |
| BMP, Mis | Smad, Smurf, LIMK, MKK, Erk, p38, Cofilin | (2007) Cross-talk between the bone morphogenetic protein pathway and other major signaling pathways results in tightly regulated cell-specific outcomes. *FEBS J.* 274(12), 2977-85 |
| GPCR ligands | CD44, FAT, KIBRA, FRMD, Mst, YAP, LATS, MOB, SAV, TEAD, Smad | (2010) The hippo signaling pathway in development and cancer. *Dev. Cell* 19(4), 491-505. |
| Dachsous (Ds), Ex | Mer, KIBRA, Mst, SAB, LATS, MOB, YAP, TAZ, Smad, TEAD | (2011) SnapShot: The hippo signaling pathway. *Cell* 145(3), 484-484.e1 |
| GTP and See also MAPK, PI3K ligands | Rho, Rac, Raf, PAK, MEK, Erk, Myc/Max, JNK, HIF, CREB, PI3K | "The Ras superfamily at a glance". *J. Cell. Sci.* 118 (Pt 5): 843-6. doi: 10.1242/jcs.01660. |

TABLE 8

Cell Process - Cytoskeletal Regulation and Adhesion

Regulation of Actin Dynamics - related to many pathways, see for example integrin receptor binds ECM ligands, GPCR ligands, growth factors binding receptors (receptor tyrosine kinases)
Regulation of Microtubule Dynamics - related to many pathways above, see for example Wnt signaling, neutrophins/trophins
Adherens Junction Dynamics - related to many pathways above, see for example PI3K, MAPK Physiological response parameters include those described herein, e.g., cell adhesion, cell attachment, cell morphology, cell proliferation, cell signaling, cell density, cell size, cell shape, cell polarity, pH, $O_2$, $CO_2$, glucose, and combinations thereof. In exemplary embodiments, the physiological response parameter is a change in cell adhesion or attachment.

Methods of analyzing the continuous measurements to determine whether a change in a physiological response parameter occurs in the cellular sample are described herein (e.g., magnitude of response (positive or negative), time to max or min, slope of time vs. magnitude at any point of the response timeline, etc.). These and other methods of non-linear analysis can be used to determine whether a change in a physiological response parameter occurs in the presence of a perturbing agent.

Baselines and controls can be used to adjudge the status of the cellular pathway. Suitable baselines can include, but are not limited to, a sample without the perturbing agent, a sample of infinite dilution of the perturbing agent, the same sample prior to or following sufficiently lengthy time after the addition of the perturbing agent, and other such baselining activities known to those skilled in the art of cell based assays.

Suitable controls can include, but are not limited to, a sample of healthy material from the same patient, a sample of healthy material from a different patient, a sample with a similar but different activating agent, a cell line of known positive or negative response, a sample treated with the inverse activity of the activating agent, a sample of diseased material from one or more patients, and other such positive and negative controls known to those practiced in the art of cell based assays.

In some embodiments, data obtained from titrating the quantity of the perturbing agent can be used to determine the efficacy of a targeted therapeutic agent in an individual subject. For example, if diseased cell samples are exposed to increasing concentrations of the perturbing agent, an EC50 value of the perturbing agent on viable cells in the cell sample can be generated, wherein the EC50 value for that cell sample is predicative of the efficacy of targeted therapeutic agents known to disrupt the cellular pathway effected by the perturbing agent, when the cellular pathway is functioning normally. By determining the EC50 value, the sensitivity of the patient cell sample to the perturbing agent is acquired and can thus be used to assess the extent to which the associated cellular pathway is functional or dysfunctional in that patient.

In one example, the EC50 is a very small number, indicating that the patient is very sensitive to the smallest amount of perturbing agent. If the perturbing agent is a natural agent found in normal human fluids, treatment designed to reduce this agent level may be ineffective at attenuating this agent level below the low EC50. In another example, a member of a pathway is constitutive and may render the pathway unresponsive or very weakly responsive to the perturbing agent, indicating that the cellular pathway is dysfunctional. In this example, the EC50 is a very large number. In another example, a pathway member may be overexpressed, resulting in an inordinate physiologic response of the pathway upon addition of the perturbing agent, contributing to the dysfunctional pathway status. In yet another example, a pathway member may be hypoactive through, for example, mutation, under expression, locked in an inactive state, or sequestration, contributing to the dysfunctional status. In another embodiment, a pathway member may be inappropriately linked to other cellular functions, generating a physiologic response uncharacteristic of a normal pathway response, contributing to the dysfunctional status.

Data obtained from titrating the perturbing agent may also be used to assess the potency (i.e., what concentration achieves one half maximal effect) and/or efficacy (i.e., maximum achievable effect) of the perturbing agent.

The EC50 result for the isolated label-free disease cell sample from one individual subject can be compared to the EC50 results for isolated label-free cell samples from other individual subjects containing essentially the same cell type and tested with the same perturbing agent. A statistical analysis can be performed, where the statistical analysis is predictive of the functional status of the cellular pathway. The functional status of the cellular pathway in an individual subject is indicative of the responsiveness of the subject to therapeutic agents targeted to that pathway.

G. Methods of Analyzing Cell Cycle Status to Measure Drug Efficacy

Cyclin-dependent kinases (CDKs) act as major regulators of the cell cycle. A number of targeted therapeutic agents developed to treat various types of cancer target CDKs. In one embodiment of the methods described herein, the activity of the CDK pathway is isolated in order to measure the status of the cell cycle, and this measurement can be correlated with drug efficacy.

Accordingly, in some embodiments, the methods described herein can make use of perturbing agents and/or targeted therapeutic agents that perturb cellular pathways involved in moving a cell to a particular cell cycle status. For example, when the drug trastuzumab is working as intended, it clearly causes the cell cycle to become static in G1/S phase, leaving the cell unable to propagate further and disrupting the cancerous state. The methods described herein would ascertain the efficacy of trastuzumab in a patient sample by measuring the functional status of the cell in G1/S phase, e.g., by testing the status of pathways associated with G1/S status. Such pathways are well known in the art. In other examples, a perturbing agent can be selected that pauses the cell in G0 phase, and the methods described herein can be used to test pathway function associated with this resting or quiescent cell phase. In yet other examples, an agent can be selected which causes the cell to enter or begin to enter apoptosis, and the methods described herein can test pathway function associated with the entrance into the cell death cycle.

H. Analysis and Interpretation of Test Results

The test results obtained using the methods described herein can be analyzed and interpreted in a variety of ways to provide information to a clinician and/or a patient. Certain embodiments are set forth as follows.

(i) Diseased Pathway Analysis. This analysis identifies abnormal pathway activity found in a patient ex vivo that is likely to confound a drug's ability to function as intended. The analysis will provide physicians, for the first time, with a dynamic evaluation of how a patient's disease process is functioning. In this embodiment, tested pathways can be classified into one of four groups, three of which are abnormal. Pathways exhibiting abnormal activity are classified as either constitutively active, hyperactive, or not active at all (hypo-active). Pathway activity falling into these categories would be difficult to regulate, and thus a therapeutic agent targeting such pathways would not be efficacious. Pathways that demonstrate activity typically expected would be classified as normal. A drug targeting pathways exhibiting normal activity is expected to disrupt that activity, thereby producing the intended effect in a patient.

(ii) Drug Functionality Analysis. This analysis provides two measures of the functionality of a drug ex vivo.

1) Response Score (RS): The response score characterizes the functional effect that a tested drug had on the targeted pathway. It can be reported on a 0-1 scale, where a higher score indicates greater drug functionality.

2) Response Score Percentile Ranking (RSPR): RSPR characterizes how a patient's Response Score ranks relative to the scores received by other patients tested with the same agent. For each patient, the percentile of their Response Score within the total group is determined. Once a percentile ranking has been assigned, patients can then be classified into one of three groups: a) below median, b) near median, or c) above median. For certain drugs, a wide variation in patient drug response as measured by a clinical endpoint such as time to progression (TTP) will be mirrored in the variation in Response Scores. Since it is often the case that the TTP period of the 75th percentile patient in a clinical trial is 5-10 times greater than the TTP period of the 25th percentile patient, providing physicians with the relative rank of their patient's response score gives them important interpretive context. For instance, they could estimate the TTP period for an individual patient based on the TTP period of patients in a clinical trial at the percentile range that corresponds to the Response Score percentile of the individual patient.

(iii) Prediction of Likely Clinical Outcome. This analysis reflects the correlation found in a clinical trial between the Response Score and the clinical endpoint for patients tested and observed after receiving the agent in question. With this correlation, it is possible to identify the clinical outcome that is consistent with patients who received a certain Response Score in a clinical trial. For example, if TTP was the clinical outcome measured, a patient's results could be classified into one of three categories.

1) Likely TTP Period—Lowest: Patients falling into this sub-population are likely to experience a TTP period that is well below the median TTP period the entire population of patients would experience.

2) Likely TTP Period—Indeterminate: No assessment is provided for patients who receive a Response Score that falls in this category.

3) Likely TTP Period—Highest: Patients falling into this sub-population are likely to experience a TTP period that is well above the median TTP period the entire group of patients would experience.

Clinicians would use the results of the CELx Profile test as guidance as they determine which drug therapy to select. When a patient's cells are tested with multiple drugs, the likely clinical outcome of each drug can be compared so that the physician can select the drug with a test result that correlates to the greatest likely clinical outcome.

I. Kits

In another aspect of the invention, kits are provided. In certain embodiments, the kit comprises a container for a disease cell sample from an individual subject containing a transport medium; a container for a control cell sample from the individual subject containing a transport medium; a biosensor; a non transitory computer readable medium having computer executable instructions for converting data from the biosensor into an output, wherein the output shows a change in a cellular physiological response parameter over a defined period of time, wherein the cellular physiological response parameter is selected from the group consisting of pH, cell adhesion, cell attachment pattern, cell proliferation, cell signaling, cell survival, cell density, cell size, cell shape, cell polarity, $O_2$, $CO_2$, glucose, cell cycle, anabolism, catabolism, small molecule synthesis and generation, turnover, and respiration, ATP, calcium, magnesium, and other charged ions, proteins, specific pathway member molecules, DNA and or RNA in various cellular compartments, genomics, and proteomics, post-translational modifications and mechanisms, levels of secondary messenger, cAMP, mRNA, RNAi, microRNAs and other RNA with physiologic function, and combinations thereof; classifying the output as above or below a cutoff value indicating status as a responder or nonresponder and/or classifying the sample as having no response, weakly responsive, and responsive; and generating a report with the classification.

Types and amount of a disease cell samples are described herein. In certain embodiments, the disease cell sample is a whole cell label free viable cell sample having at least 5,000 cells. In embodiments, a control cell sample is selected from the group consisting of a disease cell sample from the same subject, a healthy cell sample from the same subject, a cell sample known to respond to the therapeutic agent, a cell sample known not to respond to the therapeutic agent, and combinations thereof.

The containers and the transport medium are designed to maintain cell viability and to minimize cell activation. In embodiments, the media and containers are endotoxin free, nonpyrogenic and DNase- and RNase-free. Once obtained the cell samples are maintained in a transport medium that retains the cell viability. Depending on the length of time for transportation to the site of analysis, different media may be employed. In embodiments, when transportation of the tissue sample may require up to 10 hours, the media has an osmolality of less than 400 mosm/L and comprises Na+, K+, Mg+, Cl—, Ca+2, glucose, glutamine, histidine, mannitol, and tryptophan, penicillin, streptomycin, contains essential amino acids and may additionally contain non-essential amino acids, vitamins, other organic compounds, trace minerals and inorganic salts, serum, cell extracts, or growth factors, insulin, transferrin, sodium selenite, hydrocortisone, ethanolamine, phosphophorylethanoloamine, tridothyronine, sodium pyruvate, L-glutamine, to support the proliferation and plating efficiency of human primary cells. Examples of such a media include Celsior media, Roswell Park Memorial Institute medium (RPMI), Hanks Buffered Saline, and McCoy's 5A, Eagle's Essential Minimal Media (EMEM), Dulbecco's modified Eagle's medium (DMEM), Leibovitz L-15, or modifications thereof for the practice of primary cell care.

Biosensors are described herein. In certain embodiments a biosensor is selected from the group consisting of a biosensor that detects a cellular parameter selected from the group consisting of, cell adhesion, cell attachment, cell morphology, cell phenotype, cell proliferation, cell signaling, cell density, cell polarity, pH, $O_2$, $CO_2$, glucose, and combinations thereof. In embodiments, the device is an impedance or an optical device. Biosensors may be optionally coated as described herein. In embodiments, a biosensor is selected that measures a change in a physiological parameter associated with the type of therapeutic and/or activator agent as described herein.

In other embodiments, the kit comprises a non-transitory computer readable medium having computer executable instructions for converting data from the biosensor into an output, wherein the output shows a change in a cellular physiological response parameter over a defined period of time, wherein the cellular physiological response parameter is selected from the group consisting of pH, cell adhesion, cell attachment pattern, cell proliferation, cell signaling, cell survival, cell density, cell size, cell shape, cell polarity, $O_2$, $CO_2$, glucose, and combinations thereof; classifying the output as a responder or nonresponder and/or no response, weakly responsive, and responsive; and generating a report with the classification.

In other embodiments, the invention provides a computing device or computer readable medium with instructions to implement the methods of the disclosure. The computer readable medium includes non-transitory CD, DVD, flash drive, external hard drive, and mobile device.

The kits and methods described herein can employ the use of a processor/computer system. For example, a general purpose computer system comprising a processor coupled to program memory storing computer program code to implement the method, to working memory, and to interfaces such as a conventional computer screen, keyboard, mouse, and printer, as well as other interfaces, such as a network interface, and software interfaces including a database interface find use one embodiment described herein.

The computer system accepts user input from a data input device, such as a keyboard, input data file, or network interface, or another system, such as the system interpreting, for example, the data generated by the biosensor over a defined period of time, and provides an output to an output device such as a printer, display, network interface, or data storage device.

Input device, for example a network interface, receives an input comprising a change in a cellular physiological parameter as described herein and/or quantification of these changes. The output device provides an output such as a display, including one or more numbers and/or a graph depicting the detection and/or quantification of the change in a cellular parameter.

The computer system can be coupled to a data store which stores data generated by the methods described herein. This data is stored for each measurement and/or each subject; optionally a plurality of sets of each of these data types is stored corresponding to each subject. One or more computers/processors may be used, for example, as a separate machine, for example, coupled to computer system over a network, or may comprise a separate or integrated program running on computer system. Whichever method is employed these systems receive data and provide data regarding detection/diagnosis in return.

In some embodiments, the computing device can include a single computing device, such as a server computer. In other embodiments, the computing device can include multiple computing devices configured to communicate with one another over a network (not shown). The computing device can store multiple databases within memory. The databases stored on the computing device can be organized by clinic, practicing clinician, programmer identification code, or any other desired category.

Data from the biosensor can be sent to the remote computing system or another data storage device. The communication process initializes and begins at a start module and proceeds to a connect operation. The connect operation communicatively couples the stored information of the health care provider to the remote computing system, for example, via a cabled connection, a wireless local area network (WLAN or Wi-Fi) connection, a cellular network, a wireless personal area network (WPAN) connection, e.g., BLUETOOTH®, or any desired communication link.

A transfer operation transmits data from the biosensor to the computing device. In an embodiment, the transfer operation encrypts the data before transmitting the data between the devices. The communication process can complete and end at a stop module. Once the biosensor data is transferred to a remote computing device, the data is converted to an output, such as a cell index measurement over time. In certain embodiments, a defined endpoint is selected and is used to classify the cell sample as no response, weakly responsive or responsive as described herein. In embodiments, the status of the analysis of the sample as a responder or non responder is communicated back to the health care provider using a similar process over cabled connection, a wireless local area network (WLAN or Wi-Fi) connection, a cellular network, a wireless personal area network (WPAN) connection, e.g., BLUETOOTH®, or any desired communication link.

In certain embodiments, the computer readable storage medium has computer-executable instructions that, when executed by a computing device, cause the computing device to perform steps comprising: converting data from the biosensor into an output, wherein the output shows a change in a cellular physiological response parameter over a defined period of time, wherein the cellular physiological response parameter is selected from the group consisting of pH, cell adhesion, cell attachment pattern, cell proliferation, cell signaling, cell survival, cell density, cell size, cell shape, cell polarity, $O_2$, $CO_2$, glucose, and combinations thereof in the presence and/or absence of a therapeutic agent; classifying the output as no response, and responsive at a defined endpoint by comparing the output from biosensor from the cell sample in the presence of the therapeutic agent to the output from biosensor from the cell sample in the absence of the therapeutic agent; and generating a report with the classification. In embodiments, the computer executable instructions comprise instructions for communicating the classification to a health care provider.

In other embodiments, the computer readable storage medium may include instructions for identifying which pathways are operative in the disease cell sample of the subject. The instructions that when executed by a computing device comprise determining whether there is a difference between the output of the biosensor data from a disease cell sample from a subject treated with a first activating or perturbing agent to the output of the biosensor data from a second disease cell sample from the same subject not treated with the first activating or perturbing agent to one another to determine whether the pathway responsive to the first activator or perturbant agent is active in the disease cell sample; identifying the presence of the difference in output as an indication of activity of the pathway, and communicating the activity of the pathway to a health care provider. Activator or perturbant agents and their pathways are described herein.

EXAMPLES

Discussion of Experimental Design

The methods utilize a CReMS to measure the physiologic change of a cell or cell pathway after protein binding within a cell or cell pathway has occurred. It is commonly understood that a drug cannot work unless it is bound, and that nearly all disease genes fall into core signaling pathways. In light of this and the fact biochemical principles of protein binding are universal across cell types, the methods described herein are thus broadly applicable to all cells and cell pathways where protein and other biomolecule binding can occur.

The current state-of-the-art genetic tests cannot indicate directly whether a drug or the pathway is bound, and hence they cannot reliably predict drug response. By identifying the physiologic change that occurs within a cell after a drug is introduced, the CELx test can reliably predict the response of the subject's cells to the drug, At least five types of CELx tests are envisioned using the methods described herein.

1) A Pathway Shutdown test that determines the efficacy of targeted pathway drugs. In this test, the physiologic change of the test cells caused by the binding of a targeted pathway drug to its cellular target is measured and compared to a baseline measurement.

2) An Anti-Proliferation test that determines the efficacy of anti-proliferation drugs. In this test, the physiologic change of the test cells caused by the inhibition of their proliferative capacity is measured and compared to a baseline measurement.

3) A Combination Test that determines the efficacy of two or more drugs utilized in combination. In this test, the physiologic change of the test cells caused by the drugs is measured and compared to a baseline measurement. A Combination Test can include two or more targeted pathway drugs, two or more anti-proliferation drugs, or one or more of each type of drug.

4) A Functional Pathway Test that demonstrates function of the pathway in a specific patient. In this test, the physiologic change of the test cells caused by addition of a perturbant is indicative of a functional pathway in a patient.

5) A Ligand/Target Test to determine if the ligand and or target are present by measuring the presence of the ligand and or target combined.

To demonstrate the embodiments of these tests, 65 experiments on cells from 11 different patients with three different types of cancer were performed. Sixteen different drugs affecting 11 different cell pathways were tested and two different CReMS types were utilized. A list of the tests whose results are reported in the examples of this application is provided in Table 9 below:

TABLE 9

List of Tests Performed

| Example | Drug | Target | Pathway | Patient Cells |
|---|---|---|---|---|
| Ex. 1 | Lapatinib | Her2 receptor | MAPK, RHO, AKT, FAK1, RAS/RAF, PIK3/PTEN, cellular adhesion | B1, B4 |
| Ex. 1 | Trastuzumab | Her2 receptor | MAPK, RHO, AKT, FAK1, RAS/RAF, PIK3/PTEN, Cellular adhesion | B1, B4 |
| Ex. 2 | Paclitaxel | TUBB1, BCL2 | Apoptotic pathways, cellular adhesion | B1, B2 |
| Ex. 3 | Cetuximab and Irinotecan | EGFR Topoisomerase I | MAPK, RHO, AKT, FAK1, RAS/RAF, PIK3/PTEN, Apoptotic pathways, cellular adhesion | C1, C3 |
| Ex. 4 | Capecitabine | Thymidylate synthase | Apoptotic pathways, cellular adhesion | B2 |
| Ex. 4 | Cetuximab | EGFR | MAPK, RHO, AKT, FAK1, RAS/RAF, PIK3/PTEN, cellular adhesion | B3, B5, C1, C2, C1, C2 |
| Ex. 4 | Cisplatin | DNA | Apoptotic pathways, cellular adhesion | L1, L2 |
| Ex. 4 | Docetaxel | TUBB1, BCL2 | Apoptotic pathways, cellular adhesion | B1, B2, B3, B4 |
| Ex. 4 | Erlotinib | EGFR | MAPK, RHO, AKT, FAK1, RAS/RAF, PIK3/PTEN, cellular adhesions | L1, L2 |
| Ex. 4 | Fluorouracil | Thymidylate synthase | Apoptotic pathways, cellular adhesion | B1, B3 |
| Ex. 4 | Gefitinib | EGFR-TK | MAPK, RHO, AKT, FAK1, RAS/RAF, PIK3/PTEN, cellular adhesion | B1, B2, B3 |
| Ex. 4 | GSK1059615 | PI3K | PI3K/PTEN, cellular adhesion | B1, B2, B3, B4, B5, B7 |
| Ex. 4 | GSK1120212 | MEK1 and MEK 2 | MEK, cellular adhesion | B1, B2, B3, B5, B7, B8 |
| Ex. 4 | Irinotecan | Topoisomerase I | Apoptotic pathways, cellular adhesion | C1, C2 |

TABLE 9-continued

List of Tests Performed

| Example | Drug | Target | Pathway | Patient Cells |
|---|---|---|---|---|
| Ex. 4 | Lapatinib | Her2 receptor | MAPK, RHO, AKT, FAK1, RAS/RAF, PIK3/PTEN, cellular adhesion | B2, B3, B5, B6, B7 |
| Ex. 4 | Oxiliplatin | GG, AG, GNG | Apoptotic pathways, cellular adhesion | C1, C2 |
| Ex. 4 | Paclitaxel | TUBB1, BCL3 | Apoptotic pathways, cellular adhesion | B3, B4 |
| Ex. 4 | Paclitaxel and Cisplatin | TUBB1, BCL2, DNA | Apoptotic pathways, cellular adhesion | L1, L2 |
| Ex. 4 | Pazopanib | VEGF receptor | PI3K/PTEN, RAS/RAF, MAK, MKK, cellular adhesion | B1, B2, B3, B5, B7, B8 |
| Ex. 4 | Trastuzumab and Lapatinib | Her2 receptor | MAPK, RHO, AKT, FAK1, RAS/RAF, PIK3/PTEN, cellular adhesion | B1, B2, B3, B4 |
| Ex. 4 | Topotecan | Topoisomerase I | Apoptotic pathways, cellular adhesion | B3 |
| Ex. 4 | Trastuzumab | Her2 receptor | MAPK, RHO, AKT, FAK1, RAS/RAF, PIK3/PTEN, cellular adhesion | B2, B3 |
| Ex. 5 | Cetuximab (optical, impedance) | EGFR | MAPK, RHO, AKT, FAK1, RAS/RAF, PIK3/PTEN, cellular adhesion | B1, B2, B3, B4 |

Rationale for Experimental Design

Tissue:

Tissues from three of the cancers with the highest occurrence rates were chosen.

Breast Cancer. Breast cancer cells were utilized for 64% of tests since the breast cancer model is representative of many other cancers in terms of progression, varieties of cellular morphologies, variable metabolic rates, and survival and has aberrant molecules and pathways common to cancers found in many other tissues.

Colon and Lung Cancer. Colon and lung cancer cells were utilized to demonstrate applicability of the systems and methods of the disclosure in other significant cancer types.

Cells:

Cells from eight patients with common clinical presentations of epithelial cell types for breast cancer were selected for testing. Cells from the patients were obtained using cell sample collection techniques used regularly by those practiced in the art of tissue collection.

Patient B1: Cells are derived of a TNM stage IIA, grade 3 primary invasive ductal carcinoma of the breast in a 61-year-old woman. The cells have a doubling time of approximately 31 hours, appear as enlarged with occasional amorphous-shaped epithelial cell morphology, and have a very high expression level of ERB B1 and ERB B2 receptors. The Estrogen Receptor (ER), Progesterone Receptor (PR) and Oncogene TP53 status are all three negative.

Patient B2: Cells are derived of pleural effusion of adenocarcinoma of the breast of a 51-year old Caucasian woman. The cells have a doubling time of approximately 28 hours, appear with invasive, eel-like morphology and have high expression levels of ERB B1 and slightly elevated above normal ERB B2 receptor level, are Estrogen Receptor (ER) negative, Progesterone Receptor (PR) negative and have a high Oncogene TP53 status.

Patient B3: Cells are derived of pleural effusion of adenocarcinoma of the breast in a 43-year-old white woman; approximately 20 hours doubling time, cobblestone epithelial morphology, very high expression levels of ERB B1 and ERB B2 receptors, and Estrogen Receptor (ER) negative, Progesterone Receptor (PR) negative, and Oncogene TP53 positive status.

Patient B4: Cells are derived of ascites fluid of invasive ductal carcinoma of the breast in a 47-year-old black woman; has a doubling time of 110 hours, a round, grape-like cluster morphology, has very high expression levels of ERB B1 and ERB B2 receptors, and Estrogen Receptor (ER) positive, Progesterone Receptor (PR) negative, and Oncogene TP53 wild type-low status.

Patient B5: Cells are derived of primary breast invasive ductal carcinoma in a 60-year-old white woman; 28 hours doubling time, mixture of amorphous spreading and invasive morphology, very high expression levels of ERB B1 and ERB B2 receptors, and Estrogen Receptor (ER) positive, Progesterone Receptor (PR) positive, and Oncogene TP53 positive status.

Patient B6: Cells are derived of primary breast metaplastic carcinoma TNM stage IV grade 3 in a 70-year-old black woman; approximately 30 hours doubling time, roughened spreading morphology, very high expression levels of ERB B1 and ERB B2 receptors, and Estrogen Receptor (ER) negative, Progesterone Receptor (PR) negative, and Oncogene TP53 mutated low status.

Patient B7: Cells are derived of pleural effusion of invasive ductal carcinoma of the breast in a 69-year-old white woman; 30 hours doubling time, small mosaic epithelial morphology, low expression levels of ERB B1 and ERB B2 receptors, and Estrogen Receptor (ER) positive, Progesterone Receptor (PR) positive, and Oncogene TP53 wild type status.

Patient B8: Cells are derived of pleural effusion of adenocarcinoma of the breast in a 48-year-old white woman; 24 hours doubling time, very small grape-like cluster morphology, low expression level of ERB B1 receptors, high expression level of ERB B2 receptors, and Estrogen Receptor (ER)

negative, Progesterone Receptor (PR) negative, and Oncogene TP53 wild-type low status.

Cells from two patients with common clinical presentations of epithelial cell types for colon cancer were selected for testing:

Patient C1: Cells are derived of a male colorectal carcinoma. The cells have a spheroid volume doubling time of 14 hours, high levels of ERB B1, mutant K-Ras, mutant PIK3CA and oncogeneTP53 positive status.

Patient C2: Cells are derived of a primary colon adenocarcinoma, grade 2, in a 44 year-old Caucasian female. The cells have a spheroid volume doubling time of 46 hours, high levels of ERB B1, mutant BRAF, and oncogene TP53 negative status.

Cells from two patients with common clinical presentations of epithelial cell types for non-small cell lung cancer were selected for testing:

Patient L1: Cells are derived of pleural effusion of non-small cell lung carcinoma of a 25-year-old male; 48 hours doubling time, epithelial morphology, elevated expression levels of ERB B1 and ERB B2 receptors, PIK3CA positive, and KRAS, BRAF both negative status.

Patient L2: Cells are derived of a bronchioloalveolar adenocarcinoma of a 52-year-old white male; approximately 30 hours doubling time, epithelial morphology, normal expression levels of ERB B1 and ERB B2 receptors, and BRAF, HRAS, PIK3CA, and KRAS all negative status.

Cell Pathway Targets:

The drugs chosen for these experiments affect eleven cellular pathways which are representative of most cellular regulatory pathways in how they are extensively interconnected, regulated through binding, involve enzymatic activities such as phosphorylation and de-phosphorylation, and control critical cellular functions.

MAPK. (EGFR, EGFR-TK, HER1, HER 2). Mitogen-activated protein (MAP) kinases are found in all cell types and are essential serine/threonine-specific protein kinases that respond to extracellular stimuli (mitogens, osmotic stress, heat shock and pro-inflammatory cytokines) and regulate various cellular activities, such as gene expression, mitosis, differentiation, proliferation, and cell survival/apoptosis. Their tight regulation is important to maintaining cellular viability. The epidermal growth factor receptor (EGFR; ErbB-1; HER1 in humans) is the cell-surface receptor for members of the epidermal growth factor family (EGF-family) of extracellular protein ligands. Mutations that lead to EGFR overexpression (known as up-regulation) or over-activity have been associated with a number of cancers, including lung cancer, anal cancers and glioblastoma multiforme. Mutations, amplifications or mis-regulations of EGFR or family members are implicated in about 30% of all epithelial cancers, and it is the target of an expanding class of anticancer therapies.

PI3K/PTEN (Her2, 3, 4, VEGF). The phosphatidylinositol 3-kinase (PI3K) pathway found in nearly all cell types is critical for cell survival and cell growth, and can be activated by growth factors binding to cell surface receptors. It is an intricate signaling cascade that is among the most frequently activated pathways in cancer. It is targeted by genomic aberrations including mutation, amplification and rearrangement more frequently than any other pathway in human cancer. VEGF Receptor is expressed across a wide range of human tumors and cell lines. Expression of VEGF has been shown to lead to the development and maintenance of a vascular network that promotes tumor growth and metastasis. VEGF is expressed in a majority of non-small cell lung cancer (NSCLC), colorectal, and other tumors. VEGF is expressed at higher levels as lung cancer progresses. Moreover, a large and growing body of evidence indicates that VEGF gene expression is associated closely with poor prognosis.

Cell Adhesion. Cell adhesion pathways intersect nearly all major physiological functions. The pathways involve the binding of a cell to a surface, extracellular matrix or another cell using cell adhesion molecules such as selectins, integrins, and cadherins. Correct cellular adhesion is essential in maintaining multicellular structure. Cellular adhesion can link the cytoplasm of cells and can be involved in signal transduction. All adhesion is mediated by the cell surface, either directly involving integral components of the plasma membrane, or indirectly through material excreted and deposited on the outside of the cell.

MEK. MEK is a key protein kinase in the RAS/RAF/MEK/ERK pathway, which signals for cancer cell proliferation and survival. MEK is frequently activated in cancer, in particular in tumors that have mutations in the RAS and RAF oncogenes. MEK also regulates the biosynthesis of the inflammatory cytokines TNF, IL-6 and IL-1, which can act as growth and survival factors in cancer. The MEK pathway acts as a central axis in the proliferation of different tumors including melanoma, non-small cell lung, head/neck and pancreatic cancers. And MEK inhibition, either alone or in combination with other agents, is an important therapeutic strategy in treating cancer.

RHO. Rho proteins are involved in a wide variety of cellular functions such as cell polarity, vesicular trafficking, the cell cycle and transcriptomal dynamics. Rho activation can have a number of different effects in cancerous cells. In the initiation of the tumor, modification of Rho activity can suppress apoptosis and therefore contribute to artificial cell longevity. After natural apoptosis is suppressed, abnormal tumor growth can be observed through the loss of polarity in which Rho proteins play an integral role. Next, the growing mass can invade across its normal boundaries through the alteration of adhesion proteins potentially caused by Rho proteins.

AKT. AKT is serine/threonine kinase and functions intracellularly as a cardinal nodal point for a constellation of converging upstream signaling pathways, which involve stimulation of receptor tyrosine kinases such as IGF-1R, HER2/Neu, VEGF-R, PDGF-R, and an assembly of membrane-localized complexes of receptor-PI-3K and activation of Akt through the second messenger PIP. Because AKT and its upstream regulators are deregulated in a wide range of solid tumors and hematologic malignancies, and in view of the aforementioned biologic sequelae of this pathway, the AKT pathway is considered a key determinant of biologic aggressiveness of these tumors, and a major potential target for novel anti-cancer therapies.

FAK1. The biological importance of Focal adhesion kinase 1 (FAK1)-mediated signal transduction is underscored by the fact that this tyrosine kinase plays a fundamental role in embryonic development, in control of cell migration, cell cycle progression, and in apoptosis. It plays a central role in the survival of anchorage-dependent cells and is essential for integrin-linked cell migration—the processes that play important roles in the development of malignancies. FAK is upregulated in a wide variety of human epithelial cancers, with expression being closely correlated to invasive potential. Recently, FAK expression has been implicated in either the progression of tumor cells to malignancy or the pathogenesis of cancer. FAK1 plays a major role in regulating Breast cancer anti-estrogen resistance.

RAS/RAF. The RAS pathway is one of the most frequently deregulated pathways in cancer. RAS signals through multiple effector pathways, including the RAF/mitogen-activated protein kinase (MAPK)/extracellular signal-regulated kinase (ERK) kinase (MEK)/ERK MAPK and phosphatidylinositol 3-kinase (PI3K)-AKT signaling cascades. The oncogenic potential of these effector pathways is illustrated by the frequent occurrence of activating mutations in BRAF and PIK3CA as well as loss-of-function mutations in the tumor suppressor PTEN, a negative regulator of PI3K. Owing to this important role of Ras in tumorigenesis, the Ras-signalling pathway has attracted considerable attention as a target for anticancer therapy.

MAK pathway. Metastasis-associated kinase (MAK) is a novel regulator of the transcription factors required for cell growth. Inhibition of this pathway leads to cell cycle arrest activity.

MKK. Mitogen-activated protein kinase kinases (MKK) signaling pathways have been to both the transcriptional and the post-translational regulation of vital cellular processes including cell differentiation, proliferation, motility and survival. Since MKK signaling pathways play essential roles in modulating the release of, and the response to VEGF, it is believed that MKK plays an important role in promoting tumor vascularization.

Apoptotic pathways. Activation of apoptosis pathways is a key mechanism by which cytotoxic drugs kill tumor cells. Apoptosis occurs through two main pathways. The first, referred to as the extrinsic or cytoplasmic pathway, is triggered through the Fas death receptor, a member of the tumor necrosis factor (TNF) receptor superfamily. The second pathway is the intrinsic or mitochondrial pathway that when stimulated leads to the release of cytochrome-c from the mitochondria and activation of the death signal. Both pathways converge to a final common pathway involving the activation of a cascade of proteases called caspases that cleave regulatory and structural molecules, culminating in the death of the cell. Defects in apoptosis signaling contribute to resistance of tumors.

Therapeutic Agent:

The therapeutic agents chosen include ones representative of small molecule drugs and those derived from antibodies. The therapeutic agents tested include some with mechanisms of action designed to shut down a specific pathway functional within a cell and others designed to cause cell apoptosis.

Cetuximab. Cetuximab (Erbitux) is a chimeric (mouse/human) monoclonal antibody, an epidermal growth factor receptor (EGFR) inhibitor, given by intravenous infusion for treatment of metastatic colorectal cancer and head and neck cancer. When growth factors bind to their receptors on the surface of the cell, the receptors give a signal that causes cells to divide. Some cancers are caused by mutated receptors that give a signal to divide even without growth factor. That causes the cells to divide uncontrollably. Cetuximab binds to receptors like that and turns off that signal.

Erlotinib. Erlotinib hydrochloride (Tarceva) is a drug used to treat non-small cell lung cancer, pancreatic cancer and several other types of cancer. It is a reversible tyrosine kinase inhibitor, which acts on the epidermal growth factor receptor (EGFR). Erlotinib specifically targets the epidermal growth factor receptor (EGFR) tyrosine kinase, which is highly expressed and occasionally mutated in various forms of cancer. It binds in a reversible fashion to the adenosine triphosphate (ATP) binding site of the receptor.

Lapatinib. Lapatinib (Tykerb/Tyverb) is an orally active drug for breast cancer and other solid tumours. It is a dual tyrosine kinase inhibitor which interrupts the HER2 growth receptor pathway. It is used in combination therapy for HER2-positive breast cancer. Lapatinib inhibits the tyrosine kinase activity associated with two oncogenes, EGFR (epidermal growth factor receptor) and HER2/neu (Human EGFR type 2). Over expression of HER2/neu can be responsible for certain types of high-risk breast cancers in women.

Trastuzumab. Trastuzumab (Herceptin) is a monoclonal antibody that interferes with the HER2/neu receptor. Its main use is to treat certain breast cancers. When it binds to defective HER2 proteins, the HER2 protein no longer causes cells in the breast to reproduce uncontrollably.

Docetaxel. Docetaxel (Taxotere) is a clinically well-established anti-mitotic chemotherapy medication (that is, it interferes with cell division). It is used mainly for the treatment of breast, ovarian, prostate, and non-small cell lung cancer. Docetaxel is of the chemotherapy drug class; taxane, and is a semi-synthetic analogue of paclitaxel (Taxol).

GSK1059615. A phosphoinositide 3-kinase inhibitor (PI3K inhibitor) is a potential medical drug that functions by inhibiting a phosphoinositide 3-kinase enzyme which is part of the PI3K/AKT/mTOR pathway, which plays a key role in cancer. Inhibiting this pathway often suppresses tumor growth.

GSK1120212. GSK1120212 is a potent and selective allosteric inhibitor of the MEK1 and MEK2 (MEK1/2) enzymes with promising antitumor activity.

Pazopanib. Pazopanib (Votrient) is a potent and selective multi-targeted receptor tyrosine kinase inhibitor of VEGFR-1, VEGFR-2, VEGFR-3, PDGFR-a/β, and c-kit that blocks tumor growth and inhibits angiogenesis.

Paclitaxel. Paclitaxel is a mitotic inhibitor used to treat patients with lung, ovarian, breast, head and neck cancer, and advanced forms of Kaposi's sarcoma. Paclitaxel stabilizes microtubules and as a result, interferes with the normal breakdown of microtubules during cell division. Together with docetaxel, it forms the drug category of the taxanes.

Fluorouracil. Fluorouracil (5-FU or f5U) (Adrucil, Carac, Efudix, Efudex and Fluoroplex) is a drug that is a pyrimidine analog which is used in the treatment of cancer. It is a suicide inhibitor and works through irreversible inhibition of thymidylate synthase. It belongs to the family of drugs called antimetabolites.

Capecitabine. Capecitabine (Xeloda) is an orally-administered chemotherapeutic agent used in the treatment of metastatic breast and colorectal cancers. Capecitabine is a prodrug, that is enzymatically converted to 5-fluorouracil in the tumor, where it inhibits DNA synthesis and slows growth of tumor tissue.

Topotecan. Topotecan (Hycamtin) is a chemotherapeutic agent that is a topoisomerase inhibitor. It is used to treat ovarian cancer and lung cancer, as well as other cancer types. Topoisomerase-I is a nuclear enzyme that prevents DNA replication, and ultimately leads to cell death. This process leads to breaks in the DNA strand resulting in apoptosis.

Irinotecan. Irinotecan (Camptosar) is a drug used for the treatment of colon cancer. Irinotecan is activated by hydrolysis to SN-38, an inhibitor of topoisomerase I. The inhibition of topoisomerase I by the active metabolite SN-38 eventually leads to inhibition of both DNA replication and transcription.

Oxaliplatin. Oxaliplatin is a coordination complex that is used in cancer chemotherapy. These platinum-based drugs are usually classified as alkylating agents. Oxaliplatin is an alkylating agent which functions by forming both inter- and intra-strand cross links in DNA. Cross links in DNA prevent DNA replication and transcription, resulting in cell death.

Cisplatin. Cisplatin (Platin) is used to treat various types of cancers, including sarcomas, some carcinomas (e.g. small cell lung cancer, and ovarian cancer), lymphomas, and germ cell tumors. It was the first member of a class of platinum-containing anti-cancer drugs, which now also includes carboplatin and oxaliplatin. These platinum complexes react in vivo, binding to and causing crosslinking of DNA, which ultimately triggers apoptosis.

CReMS Types

Two types of CReMS, an optical biosensor and an impedance biosensor, were utilized to measure the physiologic response of cells during the tests and to demonstrate how the amount of physiologic change that occurs can be measured on different types of CReMS.

Prediction Criteria

The amount of physiologic change caused during a CELx test by inhibition of a targeted pathway or an apoptotic pathway was recorded into one of three categories:
1) Non-responder: <5% reduction of the cell index by the highest physiologically relevant concentration of the two drugs as compared to the untreated control cells. This result would indicate that the patient will not respond to the tested drug combination;
2) Responder (weak): Between 5-50% reduction of the cell index by the drugs at any level of concentration. This would indicate that the patient will respond to the combination of test drugs to some degree.
3) Responder (strong): >50% reduction of the cell index by the drugs at any level of concentration. This would indicate that the patient will respond to the test drug.

Cell index using an impedance or optical biosensor is calculated using a baseline starting point of impedance measurement or refractive index measurement. The baseline starting point impedance or refractive index is a physical observable and an indication of the health, viability, and physiologic status of a cell prior to any treatment with drug or other perturbant. Addition of drug or perturbant causes the baseline reading of impedance or refractive index to change in temporal patterns reflective of the specificity of the cellular physiologic change experienced by the cell.

Example 1

Pathway Shutdown Tests Showing Differentiated Response of Two Patients to Two Drugs A CELx Pathway Shutdown test was performed using cells from two HER2 overexpressing breast cancer patients (Patient B1 and B4), two drugs (Lapatinib and Trastuzumab) that are indicated for HER2 positive breast cancers, and human epidermal growth factor (EGF). The physiologic change of the B1 and B4 cells during the test was measured with an impedance biosensor CReMS and the output from the CReMS is recorded in FIGS. 1A and 1B. The comparison of the CELx test results and the third party clinical reference is recorded in FIG. 1C. This example illustrates how the CELx test is able to predict the responsiveness that a patient will have to different targeted pathway drugs by using a CReMS to measure the physiological change in a patient's cells continuously over a period of several hours. This example also illustrates how the presence of a genetic biomarker, in this case an overexpressing HER2 gene, is not a sufficient condition to predict efficacy of the drug.

Materials and Methods

CReM and microplate: A 4"×6", 96-well impedance microplate was placed into a Roche Applied Science (Indianapolis, Ind.) xCELLigence SP impedance biosensor designed to maintain constant voltage while measuring simultaneously the impedance of every well. The change in impedance for a particular well is proportional to the number of cells and type of attachment the cells have with the impedance microplate. Changes in impedance indicate a response to perturbation of these small cell populations.

Cells: Cells from Patient B1 and B4 were utilized. The cells were received at −80° C., thawed and cultured according to standard human epithelial cell handling procedure, typically in T75 culture flasks containing buffered media with serum at 37° C., 5% $CO_2$. Prior to addition to the impedance microplate, the cells were removed from their growth container with versene, counted, and re-suspended in media without serum or other growth factors.

Buffers and reagents: Standard media, serum, antibiotics (e.g. penicillin, streptomycin), and other buffers were purchased and used as delivered from ATCC (Manassas, Va., USA) or Life Technologies (Grand Island, N.Y.). Additional growth factor (mature human EGF ca6KDa) was purchased from R&D Systems (Minneapolis, Minn.) and prepared in buffered cell media without growth factors or serum. The therapeutic agent Lapatinib, a small molecule drug, was purchased from Selleck Chemicals (TX, USA); trastuzumab, an antibody drug, was obtained from a clinical dispensary.

Procedure: Between 6,000-12,000 cells in each well were seeded onto the impedance microplate containing 120 uL standard media with serum. The solution was replaced with media containing no serum to synchronize the cells with respect to physiologic state and pathway stimulation. Twenty microliters of drugs were added to the no-serum media two hours in advance of pathway stimulation. Pathway stimulation was initiated using EC80 doses of receptor ligand (typically 6 nM in 20 uL). The CReMS recording of physiologic change was maintained continuously for several hours from buffer exchange through complete cellular response to the pathway stimulation. The pathway test was performed at 37° C., 5% $CO_2$ and at a relative humidity 75%.

The CReMS recorded data on a continuous basis throughout the test, where the data represented the effects of the two therapeutic agents on the B1 and B4 cells.

Results: FIGS. 1A and 1B present the data collected during the CELx test on the B1 and B4 cells respectively with the antibody drug trastuzumab and the small molecule drug lapatinib. The data collected by the impedance CReMS is represented in each figure with time in minutes on the X-axis and the cell index on the Y-axis. The cell index represents the physiologic change of the B1 and B4 cells during the test.

Results indicate that stimulation of the full pathway with a ligand receptor and no drug added generated the highest cell index. After the drug trastuzumab was added to the stimulated B1 cells, the cell index of the test cells changed less than 5%, indicating the B1 test cells were unaffected by the addition of the trastuzumab. Conversely, after the drug lapatinib was added to the B1 cells, the cell index for the test cells decreased by over 50%, indicating that the activity within the targeted pathway is diminished significantly. After the drugs, lapatinib and trastuzumab were each added to separate samples of B4 cells, the cell index of each test cell sample decreased by over 50%. This indicated that the activity within the targeted pathway of each test cell sample was diminished significantly.

Based on these results, the CELx Pathway Shutdown test shown in FIG. 1A predicts that Patient B1 will not respond to trastuzumab but will respond to Lapatinib. The results shown in FIG. 1B also predict that Patient B4 would respond to both trastuzumab and lapatinib. The comparison of the CELx test prediction and the result recorded by third party clinical reference is shown in FIG. 1C; it shows that the CELx test accurately predicted the results recorded by the clinical reference standard, where Patient B1 was found unresponsive to trastuzumab and responsive to lapatinib and Patient B4 was found responsive to both.

Discussion: In the present example of this invention, the CELx test accurately predicted the efficacy of two drugs, trastuzumab and lapatinib, using cells Patients B1 and B4. The B1 and B4 cells responded to stimulation of the HER2 pathway with a receptor ligand, indicating that the patient could respond to a drug able to shut down activity within that pathway. In this example, the B1 cells demonstrate a differentiated response to the two drugs, despite the drugs having similar mechanisms of action. Patient B1 was found to be responsive to lapatinib and non-responsive to trastuzumab.

This example illustrates how the CELx test can be applied to different types of therapeutic agents, including ones that work at the cell surface, as in the case of trastuzumab, an antibody drug, or ones that work in the cytoplasm, as in the case of the kinase inhibitor drug, lapatinib. It also illustrates how the systems and methods of the disclosure are effective to detect changes in response to drugs that target the MAPK, RHO, AKT, FAK1, RAS/RAF, PIK3 and cell adhesion pathways. This example also illustrates the principle that knowledge of the presence of a relevant genetic biomarker, in this case an overexpressing HER2 gene, is not a sufficient condition to predict whether the drug will function according to its intended mechanism of action. In this example, the drug trastuzumab does not always shut down the HER2 growth factor signaling pathway in every Her2 positive cancer cell type, as it is intended to. Despite similar genetic profiles, Patients B1 and B4 respond differently to trastuzumab as confirmed by the CELx test. Conversely, an embodiment of the method of the invention accurately predicts that another drug, Lapatinib, working at the HER2 site, is able to shut down the pathway as designed for both patients. The results of this example correlate with the response reported by a third party, confirming the ability to use the measurement of physiological change in a patient's diseased cells to predict whether a therapeutic will provide the intended efficacy. With the present invention, a physician selects a treatment for a breast cancer patient based on the actual responsiveness of the tumor cells to the drugs.

Example 2

Anti-Proliferative Tests Showing Differentiated Response of Two Patients to One Drug A CELx Anti-Proliferative test was performed using cells from two breast cancer patients (Patients B1 and B2) and the drug Paclitaxel. The physiologic change of the B1 and B2 cells during the test was measured with an impedance biosensor CReMS and the output from the CReMS is recorded in FIGS. 2A and 2B. The comparison of the CELx test results and the third party clinical reference is recorded in FIG. 2C. This example demonstrates the ability of the CELx test to predicting the efficacy of a therapeutic agent by measuring the physiologic change over the course of several days in a patient's cancer cells after an anti-proliferative drug is introduced. This example also demonstrates the role of a baseline, in this case, untreated patient cells, in measuring the results. In addition, the results recorded for patient B2 demonstrate the importance of monitoring the cells' physiological response on a continuous basis over several days because of changes that can occur over time in a cell's responsiveness to a drug.

Materials and Methods

CReMS, microplate, reagents, and buffers: The CReMS, microplate, reagents, and buffers used in Example 1 are the same as those employed in Example 2, except for the therapeutic agent tested. In Example 2, the therapeutic agent, paclitaxel, was tested. Paclitaxel was purchased from Selleck Chemicals (TX, USA).

Cells: Breast Cancer cells from Patients B1 and B2 were utilized and handled in the same manner as described in Example 1.

Procedure: Between 6,000-12,000 cells in each well were seeded onto the impedance microplate containing 120 uL settling media with serum. Forty microliters of the drug paclitaxel were added to one set each of the B1 and B2 cells; another control set of B1 and B2 cells received no drug. The CReMS recording of physiologic change was maintained continuously from when the cells were first seeded on the microplate through complete cellular response, which was between 48-72 hours. The test was performed at 37° C., 5% $CO_2$ and at 75% relative humidity.

Results: FIGS. 2A and 2B present the data collected during the CELx test on the B1 and B2 cells with the drug Paclitaxel. The data collected by the impedance CReMS is represented in the figure with time in hours on the X-axis and the cell index on the Y-axis. The cell index represents the physiologic change of the B1 and B2 cells during the test. An increase in the cell index is generally an indication of increase in cell proliferation. Whereas a decrease in long term cell index is generally indicative of loss of cell viability or live cell number decrease. The B2 test cells showed initial responsiveness to Paclitaxel, as reflected in the significant decrease in CReM output compared to the B2 control cells, but after roughly 24 hours, the CReM output reverses, indicating that the test cells begin proliferating and are no longer responsive to the drug. The B1 test cells show immediate and continuous responsiveness to Paclitaxel, as reflected in the decrease in CReM output compared to the B1 control cells throughout the test period. The CELx test results presented in FIGS. 2A and 2B predict that both patients B1 and B2 will respond to paclitaxel. The comparison of the CELx test prediction and the result recorded by third party clinical reference is shown in FIG. 2C; it shows that the CELx test accurately predicted the results recorded by the clinical reference standard, where Patients B1 and B2 were both found responsive to paclitaxel.

Discussion: In the present example, the CELx test accurately predicted the efficacy of an anti-proliferative drug, paclitaxel, with two breast cancer patients, B1 and B2. Additionally, the CELx test result for Patient B2 indicated that resistance to paclitaxel develops in the short-term, illustrating the importance of monitoring the cells' physiological response on a continuous basis over an extended period of time. This result is important because one of the major issues with drug therapy is the rapid development of resistance to a drug. Time is lost when a patient is prescribed an ineffective therapy. Besides increasing the risk of chemotoxicity and incurring the common side effects of chemotherapy, in many cases, treatment with one drug eliminates the possibility of treatment with another drug that may have been more effective.

Example 3

Combination Tests Showing Response of Two Patients to Two Drugs Taken Together A CELx Combination test was performed using cells from two colon cancer patients (Patients C1 and C2), EGF, and a combination of two drugs indicated for colon cancer, Cetuximab and Irinotecan. The physiologic change of the C1 and C2 cells during the test was measured with an impedance biosensor CReMS and the output from the CReMS is recorded in FIGS. 3A and 3B. The comparison of the CELx test result and the third party clinical reference is recorded in FIG. 3C. This example demonstrates how the CELx test is able to predict the responsiveness that individual patients will have to a combination of two or more drugs in a way that cannot be done using genetic testing or expression profiling. The test also illustrates how the CELx test operates with colon cancer cells, in addition to breast cancer cells.

Materials and Methods

CReMS, microplate, reagents, and buffers: The CReMS, microplate, reagents, and buffers used in Examples 1 and 2 are the same as those employed in Example 3, except for the therapeutic agent used. In Example 3, two therapeutic agents, cetuximab and irinotecan, were tested. Irinotecan was purchased from Selleck Chemicals (TX, USA) and cetuximab was obtained from a clinical dispensary.

Cells: Colon cancer cells from Patients C1 and C2 were utilized and handled in the same manner as described in Example 1.

Procedure: Between 6,000-12,000 cells in each well were seeded into the impedance microplate containing 120 uL settling media with serum. The solution was replaced with media containing no serum to synchronize the cells with respect to physiologic state. Twenty microliters each of irinotecan and cetuximab was added to one set each of the C1 and C2 cells; another control set of C1 and C2 cells received no drugs. The CReMS recording of physiologic change was maintained continuously from when the cells were first seeded on the microplate through complete cellular response, which was between 48-72 hours. The test was performed at 37° C., 5% $CO_2$ and at 75% relative humidity.

Results: FIGS. 3A and 3B present the data collected during the CELx test on the C1 and C2 cells and the combination of the antibody drug cetuximab and the small molecule drug irinotecan. The data collected by the impedance CReMS is represented in the figures with time in hours on the X-axis and the cell index on the Y-axis. The cell index represents the physiologic change of the C1 and C2 cells during the test. Results show that the untreated control C1 and C2 cells generated the highest cell index. Results after the two drugs are added to the C1 and C2 test cells show a reduction of the cell index for each cell sample of greater than 50%. These results predict that both patients C1 and C2 will respond to the combination of cetuximab and irinotecan. The comparison of the CELx test prediction and the result recorded by third party clinical reference is shown in FIG. 3C; it shows that the CELx test accurately predicted the results recorded by the clinical reference standard, where Patients C1 and C2 were both found responsive to the cetuximab and irinotecan combination.

Discussion: In the present example, the CELx test accurately predicted the efficacy of two drugs, cetuximab and irinotecan, with two colon cancer patients, C1 and C2.

However, even though the overall results for Patient C1 with the two drugs showed a greater than 50% reduction in the cell index, the CELx test result indicated that one of the drugs, cetuximab, did not cause a physiologic change in Patient C1's cells. This would suggest that the entire therapeutic benefit of the drug combination in Patient C1 was likely due to the irinotecan. If a physician knew that only one drug within a combination therapy was effective, in this case irinotecan, they would then only prescribe the efficacious drug. The CELx test result indicated that Patient 2 was responsive to each individual drug, suggesting the combination of drugs would be more efficacious than a use of only a single drug.

The results illustrate how the CELx test is able to predict the responsiveness of individual patients to a combination of two or more therapeutic agents. The test illustrates how the CELx test operates with colon cancer cells. It further illustrates the physiological responsiveness of cancer cells to different types of drugs, in this case, the antibody drug cetuximab, that works by binding to the cell surface, and an apoptotic pathway inhibitor, in this case irinotecan, which works by binding to the cell nucleus. And it also illustrates the physiological responsiveness of cancer cells to drugs that target the MAPK, RHO, AKT, FAK1, RAS/RAF, PIK3, and cell adhesion pathways and an apoptotic pathway. The result would allow a physician to select a more efficacious treatment for a colon cancer patient

Example 4

Additional CELx Tests Using Different Drugs

Fifty-one CELx Pathway Shutdown and Anti-Proliferative single drug tests were performed using some of the cell and drug combinations possible from a selection of 11 different patient cells (breast cancer cells from Patients B1, B2, B3, B4, B5, B6, B7), colon cancer cells from Patients C1 and C2, and lung cancer cells from Patients L1 and L2) and 15 different drugs (capecitabine, cetuximab, docetaxel, fluorouracil, gefitinib, GSK1059615, GSK1120212, lapatinib, paclitaxel, pazopanib, trastuzumab, topotecan, cisplatin, erlotinib, and oxiliplatin). Six CELx Combination tests were performed, two with the drug combination of paclitaxel and cisplatin and Patient L1 and L2 cells, and four with the drug combination of trastuzumab and lapatinib and Patient B1, B2, B3, and B4 cells. The physiologic change of the cells and drugs tested was measured with an impedance biosensor CReMS and the summary output from the CReMS is recorded in FIG. 4. The correlation between these CELx test results and the third party clinical reference is recorded in FIG. 7.

Materials and Methods

CReMS, microplate, reagents, and buffers: Each of the 57 tests listed in FIG. 4 relied upon the same CReMS, microplate, reagents, and buffers as those described in the Examples 1-3.

Cells: Cells from Patients B1, B2, B3, B4, B5, B6, B7, C1, C2, L1, and L2 were utilized and handled in the same manner as described in Example 1.

Procedures: In those experiments involving targeted pathway drugs (cetuximab, gefitinib, GSK1059615, GSK1120212, lapatinib, pazopanib, trastuzumab, and erlotinib) the procedures described in Example 1 were utilized. In those experiments involving anti-proliferative drugs (capecitabine, docetaxel, fluorouracil, paclitaxel, topotecan, cisplatin, and oxiliplatin), the procedures described in Example 2 were utilized. In those experiments involving a combination of drugs, the procedures described in Example 3 were utilized. The list of patient cells and the drug tested with the cells is characterized in FIG. 4.

Results: The summary results of the 57 CELx tests performed on the various combinations of cells and drugs listed is shown in FIG. 4. For each experiment, the change of the test cells' physiologic response compared to its control cells was calculated. Each box in FIG. 4 classifies the change in physiologic response measured in each experiment as either being greater than 50%, between 5%-50%, or less than 5%. The series of tests represented in FIG. 4 illustrate the CELx test's ability to measure the physiologic change that occurs in a variety of common cancer cell types after they are exposed to wide range of drugs that target a wide range of cellular pathways. The comparison of the CELx test prediction and the result recorded by third party clinical reference is shown in FIG. 7; it shows the CELx test result correlated with the third party clinical reference reported for the patient and drug combination.

Discussion: In the 57 tests described in this example, the invention described herein demonstrated efficacy with:

Colon, breast, and lung cancer cells;

Targeted pathway drugs that inhibit the MAPK, RHO, AKT, FAK1, RAS/RAF, PI3K, MAK, MKK, MEK and cell adhesion pathways through targets that include EGFR, EGFR-TK, PI3K, MEK1, MEK2, HER2 receptor, and VEGFR; and Anti-proliferative drugs that target apoptotic pathways through targets that include Topoisomerase I, TUBB1, BCL2, DNA, purine crosslinking (GG, AG, GNG), and thymidylate synthase.

Each of the CELx test results except one correlated with the results for this Patient cell and drug combination.

Example 5

Concordance Tests Between the Results Produced from Different CReMS

A CELx Pathway Shutdown test was performed using cells from four breast cancer patients (Patient B1, B2, B3, B4) with overexpressing epidermal growth factor (EGF) receptors, one drug cetuximab, and human epidermal growth factor (EGF). The physiologic change of the four patients' cells during the test was measured with an impedance biosensor CReMS and an optical biosensor CReMs to demonstrate the correlation of the results produced from the two different CReMS. The output from the CReMS is recorded in FIG. 5. This example illustrates how the CELx test is able to use two different CReMS to obtain the same measurement of physiological change in a patient's cells.

Materials and Methods

CReMS and microplate: Two different CReMS were used in this example. In one series of tests, a 4"×6", 96-well impedance microplate was placed into a Roche Applied Science (Indianapolis, Ind.) xCELLigence SP impedance biosensor designed to maintain constant voltage while measuring simultaneously the impedance of every well. The change in impedance for a particular well is proportional to the number of cells and type of attachment the cells have with the impedance microplate. Changes in impedance indicate a response to perturbation of these small cell populations. In the other series of tests, a 4"×6", 384-well optical microplate was placed into a PerkinElmer Instruments (Waltham, Mass.) EnSpire Multimode optical biosensor designed to scan 850 nanometer near infrared reflected light in each well. The change in reflected wavelength for a particular well is proportional to the number of cells and type of attachment the cells have with the optical microplate. Changes in reflected wavelength indicate a response to the perturbation of the small cell populations in the well.

Reagents and buffers: The reagents and buffers used in Example 1 are the same as those employed in Example 5, except for the therapeutic agent employed. In Example 5, the therapeutic agent cetuximab was tested. Cetuximab was acquired from a medical dispensary.

Cells: Breast cancer cells from Patients B1, B2, B3 and B4 were utilized in both set of tests and handled in the same manner as described in Example 1.

Procedure: In the set of tests performed with the impedance biosensor CReMS, between 6,000-12,000 cells in each well were seeded onto the impedance microplates containing 120 uL settling media with serum. Forty microliters of the drug cetuximab was added to the no-serum media containing one set each of the B1, B2, B3, and B4 patient cells two hours in advance of pathway stimulation; another control set of B1, B2, B3 and B4 cells received no drug. Pathway stimulation was initiated using EC80 doses of receptor ligand (6 nM in 20 uL). The impedance CReMS recording of physiologic change was maintained continuously from when the cells were first seeded on the microplates through complete cellular response, which ranged between 20-48 hours. The test was performed at 37° C., 5% $CO_2$ and at 75% relative humidity.

In the set of tests performed with the optical biosensor CReMS, between 6,000-12,000 cells in each well were seeded onto the optical microplates containing 60 uL settling media with serum. Twenty microliters of the drug cetuximab was added to the no-serum media containing one set each of the B1, B2, B3, and B4 patient cells two hours in advance of pathway stimulation; another control set of B1, B2, B3 and B4 cells received no drug. Pathway stimulation was initiated using EC80 doses of receptor ligand (6 nM in 20 uL). The optical CReMS recording of physiologic change was maintained continuously from when the cells were first seeded on the microplates through complete cellular response, which ranged between 20-48 hours. The tests was performed at 25° C.-30° C., <5% $CO_2$ and at 30% relative humidity.

Results: FIG. 5 shows the summary results of the eight CELx tests performed separately on cells from four breast cancer patients (B1, B2, B3, and B4) with the drug cetuximab and EGF. One set of tests on cells B1, B2, B3, and B4 was performed using an optical biosensor CReMS and another set of tests on the same cells was performed using an impedance biosensor CReMS. The results are presented in a summary fashion showing the range of percentage change in output recorded by the CReMS. For each patient cell tested, the amount of physiologic change recorded by each CReMS was identical. These results illustrate that the CELx test method can utilize different types of CReMSs that measure different physiologic changes in cells.

Discussion: In the present example, a CELx Test was performed on two different CReMS that have different transducer interfaces to measure cellular physiologic change. Despite the significant differences in the devices employed for acquiring the physiological response to treatment, the optical biosensor CReMS and the impedance biosensor CReMS provided identical results for each of the patient samples. This result is important for the extension of the present invention to many CReMS types and illustration of the universality of the present invention of using an individual patient's cellular physiologic change to predict therapeutic response to drugs.

Summary of Examples

Summary of CELx Test Results and Clinical Predictions

The summary results of all 65 total CELx tests described in Examples 1-4 is presented in FIG. 6. The correlation (either 0% or 100%) between the CELx test results described in FIG. 6 and results from third party clinical references that recorded the patient's responsiveness to a single drug or drug combination is shown in FIG. 7. In all 65 tests except one, the CELx test prediction and the third party measurement generated the same result, illustrating the power of the CELx test to predict breast, lung, and colon patient response to 16 different drugs that target a wide range of cellular pathways.

The CELx test predictions for the various patient cancer cells tested in Examples 1-4 versus the third party record is provided in FIGS. 8A, 8B, 8C and 8D. A CELx test result that accurately predicts that a patient would respond to a drug or drug combination is denoted as a True Positive (TP) result. An accurate prediction that a patient would not respond to a drug or drug combination is denoted as a True Negative (TN) result. An inaccurate prediction that a patient would respond to a drug or drug combination is denoted as a False positive (FP) and an inaccurate prediction that a patient would not respond to a drug is denoted as a False Negative (FN).

FIG. 8A records the comparison of results for all tests performed in Examples 1-4 with the 12 cancer patient cells that were tested singly or in combination with 16 different drugs versus the third party record. FIG. 8B records the comparison of results for the eight breast cancer patient cells that were tested singly and in combination with thirteen different drugs versus the third party record. FIG. 8C records the comparison of results for the two different colon cancer patient cells that were tested singly and in combination with three different drugs. FIG. 8D records the comparison of results for the two different lung cancer patient cells that were tested singly and in combination with three different drugs. In each Figure, the CELx tests are shown to predict accurately whether a patient will or will not respond to a particular drug or combination of drugs except in one case In FIG. 8B, it can be seen that one patient breast cancer cell sample that was expected to be a responder to gefitinib did not show a response in the CReMS testing.

The sensitivity and specificity of the CELx test for the patient cells and drug tested in Examples 1-4 as well as for the sub-groups of patients, drugs, pathways, and CReMS types tested is provided in FIG. 9. Overall and within each of the sub-groups studied, the CELx test generated high sensitivity (98%+) and specificity (99.9%+). These results illustrate the predictive power of the test across the different cancer cell types, drug types, CReMS types, and pathways targeted in the tests described in Examples 1-4.

What is claimed:

1. A method of treating a subject, the method comprising:
administering to the subject a targeted therapeutic agent that targets a cellular signaling pathway, wherein the cellular signaling pathway has been selected by a method comprising:
contacting a diseased cell sample comprising live whole cells obtained from the subject with a receptor ligand known to agonize the cellular signaling pathway when the pathway is functioning normally;
measuring cell adhesion or attachment in the live whole cells in the sample; and
determining by analysis of the measurements whether a change in cell adhesion or attachment occurs in the diseased cell sample in the presence of the receptor ligand, relative to a control comprising a sample of the diseased cells in the absence of the receptor ligand;
wherein a change in cell adhesion or attachment in the presence of the receptor ligand, relative to the control, indicates that the cellular signaling pathway is active in the cells obtained from the subject and that the subject is suitable to receive a targeted therapeutic agent that targets the cellular signaling pathway,
wherein the targeted therapeutic agent is selected from the group consisting of: lapatinib, afatinib, erlotinib, neratinib, crizotinib, trametinib, GSK-1120212, GSK-1059615, dasatinib, imatinib, nilotinib, tivozanib, axitinib, sunitinib, pazopanib, sorafenib, regorafenib, vemurafenib, dabrafenib, palbociclib, LDK378, trastuzumab, pertuzumab, cetuximab, panitumumab, necitumumab, sym004, rituximab, ofatumumab, ibritumomab, obinutuzumab, tositumomab, brentuximab vedoton, daratumumab, alemtuzumab, bevacizumab, ramucirumab, and combinations thereof.

2. The method of claim 1, wherein the measurements of cell adhesion or attachment in the live whole cells in the sample is done on a continuous basis and the subsequent analysis is done on the continuous measurements.

3. The method of claim 1, wherein the diseased cell sample is a cancer cell sample.

4. The method of claim 3, wherein the cancer is selected from the group consisting of breast cancer, lung cancer, and colon cancer.

5. The method of claim 1, wherein the change in cell adhesion or attachment is assessed using non-linear Euclidean analysis.

6. The method of claim 5, wherein the Euclidean analysis is selected from the group consisting of arithmetic summation of the difference at multiple time points, temporal maxima, temporal minima, time to reach maxima or minima, changes in slope, absolute drop in biosensor signal, a total of all measurements, and combinations thereof.

7. The method of claim 5, wherein the change in cell adhesion or attachment is measured by a change in temporal maxima or minima.

* * * * *